US010513738B2

(12) United States Patent
Breen

(10) Patent No.: US 10,513,738 B2
(45) Date of Patent: Dec. 24, 2019

(54) METHOD TO DIAGNOSE MALIGNANT MELANOMA IN THE DOMESTIC DOG

(71) Applicant: North Carolina State University, Raleigh, NC (US)

(72) Inventor: Matthew Breen, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 94 days.

(21) Appl. No.: 15/328,733

(22) PCT Filed: Jul. 24, 2015

(86) PCT No.: PCT/US2015/041988
§ 371 (c)(1),
(2) Date: Jan. 24, 2017

(87) PCT Pub. No.: WO2016/014941
PCT Pub. Date: Jan. 28, 2016

(65) Prior Publication Data
US 2017/0211150 A1 Jul. 27, 2017

Related U.S. Application Data

(60) Provisional application No. 62/028,644, filed on Jul. 24, 2014.

(51) Int. Cl.
C12Q 1/68      (2018.01)
C07H 21/04     (2006.01)
C12Q 1/6886    (2018.01)
G01N 33/574    (2006.01)

(52) U.S. Cl.
CPC ....... *C12Q 1/6886* (2013.01); *G01N 33/5743* (2013.01); *C12Q 2600/124* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,251,601 B1 | 6/2001 | Bao et al. |
| 6,905,823 B2 | 6/2005 | Kallioniemi et al. |
| 7,930,104 B2 | 4/2011 | Baker et al. |
| 7,960,110 B2 | 6/2011 | Bastian et al. |
| 9,090,945 B2 | 7/2015 | Breen |
| 9,290,814 B2 | 3/2016 | Giafis et al. |
| 2007/0275403 A1 | 11/2007 | Morrison et al. |
| 2009/0155805 A1 | 6/2009 | Zhang et al. |
| 2009/0299640 A1 | 12/2009 | Ellis et al. |
| 2009/0324596 A1 | 12/2009 | Kang et al. |
| 2013/0210014 A1 | 8/2013 | Sharman |
| 2016/0289767 A1 | 10/2016 | Breen |

FOREIGN PATENT DOCUMENTS

| | | |
|---|---|---|
| EP | 2 513 340 B1 | 6/2016 |
| WO | 2002/077197 A2 | 10/2002 |
| WO | WO 2002/100246 | 12/2002 |
| WO | WO 2009/051842 | 4/2009 |
| WO | WO2012/078053 | 6/2012 |
| WO | WO 2012/135125 | 10/2012 |
| WO | WO 2017/210115 | 12/2017 |

OTHER PUBLICATIONS

Thomas et al. (J. of Heredity, Am. Genetic Association, vol. 98, No. 5, pp. 474-484, 2007). (Year: 2007).*
Hedan et al. (BMC Cancer, vol. 11, pp. 1-14, May 26, 2011). (Year: 2011).*
Muller et al. (Tierarztliche Praxis, vol. 40, No. 1, pp. 55-58, 2012) (Year: 2012).*
International Search Report and Written Opinion dated Oct. 30, 2015 from related International Application No. PCT/US2015/41988.
Koenig, A.; "Expression and Significance of p53, Rb, p21/waf-1, p16/ink-4a, and PTEN Tumor Suppressors in Canine Melanoma," Vet. Pathol. 39: 458-472 (2002).
Thomas, Rachael et al.; " Construction of a 2-Mb resolution BAC microarray for CGH analysis of canine tumors," Genome Research, pp. 1832-1837, Dated Feb. 13, 2005, Revised May 4, 2005.
Thomas, Rachael et al.; "Refining tumor-associated aneuploidy through 'genomic recoding' of recurrent DNA copy number aberrations in 150 canine non-Hodgkin's lymphomas," Leuk Lymphoma, 52(7): 1321-1335, dated Jul. 2011.
International Preliminary Report dated Feb. 2, 2017 from related International Application No. PCT/US2015/41988.
Al Mulla et al., "Genetic profiling of stage I and II colorectal cancer may predict metastatic relapse", Modern Pathology. vol. 19, No. 5 pp. 648-658 (2006).
Angstadt, Andrea Y. et al.; "A genome-wide approach to comparative oncology: high-resolution oligonucleotide aCGH of canine and human osteosarcoma pinpoints shared microaberrations," Cancer Genetics, 2012.
Bowman et al. (Molecular Evaluation of Canine Urothelial Carcinoma and the Cell line Model, NCSU CVM Annual Research Forum Award of Excellence for Poster presentation, Feb. 2013). (Year: 2013).
Breen et al. "An integrated 4249 marker FISH/RH map of the canine genome." BMC Genomics 5(1):65 (2004).
Breen et al. "Chromosome-Specific Single-Locus FISH Probes Allow Anchorage of an 1800-Marker Integrated Radiation-Hybrid/Linkage Map of the Domestic Dog Genome to All Chromosomes", Genome Research, 11:784-1795 (2001).
Breen, M., "Evolutionarily conserved cytogenetic changes in hematological malignancies of dogs and humans—man and his best friend share more than companionship," vol. 16, No. 1, pp. 145-154 (Feb. 25, 2008).
Decision to grant a European patent pursuant to Article 97(1) EPC for European Patent Application No. 10861217.7 dated Jun. 2, 2016.
European Search Report corresponding to European Patent Application No. 10861217.7-1403/2513340 dated Jun. 3, 2013.
Extended European Search Report issued in counterpart European Application No. 14861374.8 dated May 29, 2017 eleven (11) pages).

(Continued)

*Primary Examiner* — Jeanine A Goldberg
(74) *Attorney, Agent, or Firm* — Jenkins, Wilson, Taylor & Hunt, P.A.

(57) ABSTRACT

This disclosure is directed to the discovery of an improved method to diagnose malignant melanoma of the oral cavity in the dog.

13 Claims, 20 Drawing Sheets

(56) References Cited

OTHER PUBLICATIONS

Figure 1:
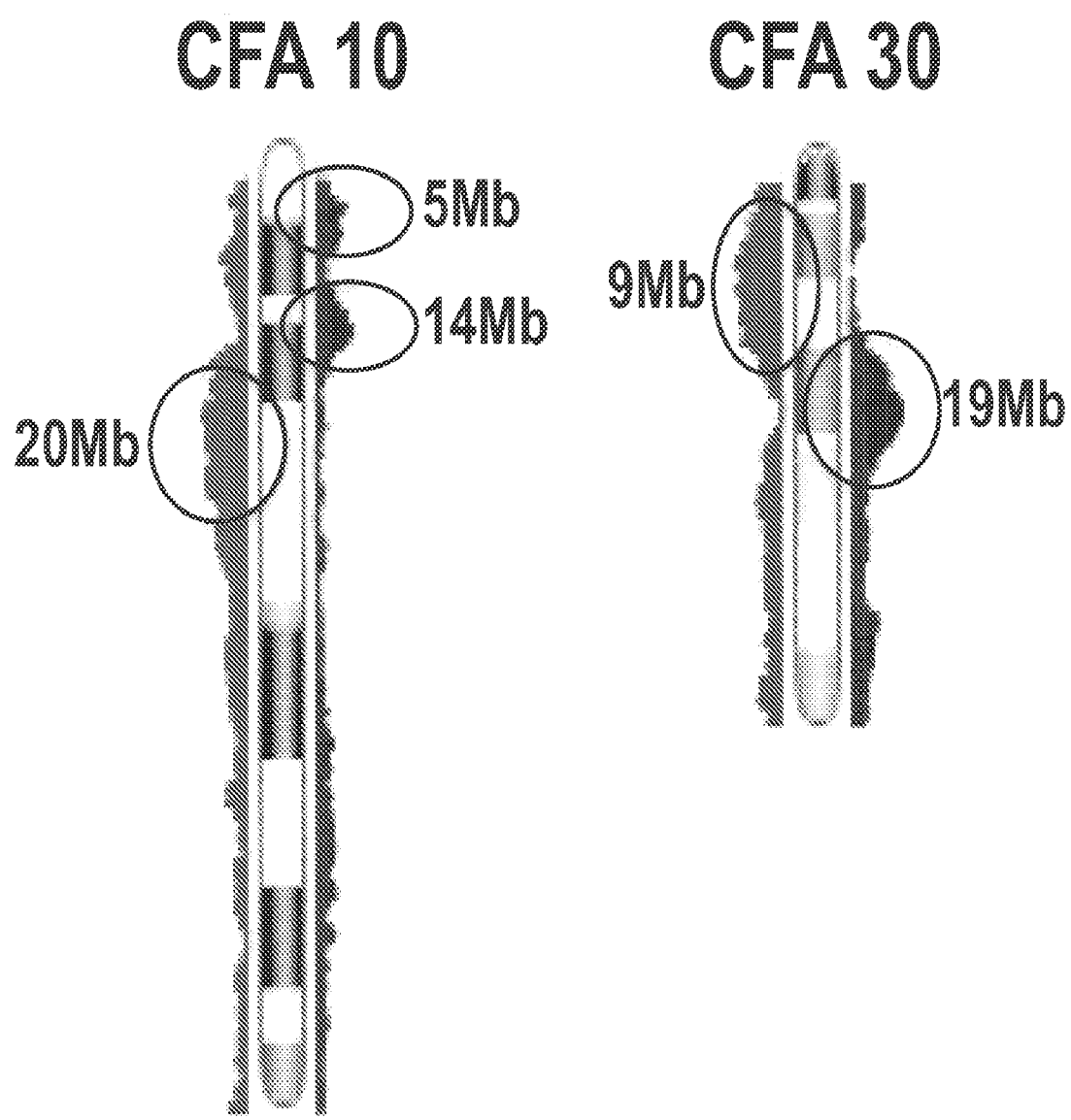

Hahn et al., "Diagnostic and Prognostic Importance of Chromosomal Aberrations Identified in 61 Dogs with Lymphosarcoma," Veterinary Pathology, vol. 31, No. 5, pp. 528-540 (Sep. 1, 1994).
International Preliminary Report on Patentability for related PCT Application No. PCT/US2014/065773 dated May 17, 2016.
International search report and the written opinion of the international searching authority for a related PCT Application No. PCT/US2014/065773 dated May 21, 2015.
International Search Report and Written Opinion dated Jul. 2, 2015 from related International Application No. PCT/US2015/025916.
International Search Report and Written Opinion issued in PCT Application No. PCT/US2017/034711 dated Sep. 14, 2017 (six (6) pages).
Karlin-Neumann al. (2012). Probing copy number variations using Bio-Rad's QX100™ Droplet Digital™ PCR system. Bio-Rad Bulletin 6277.
Letard S. et al. "Gain-of-Function Mutations in the Extracellular Domain of KIT Are Common in Canine Mast Cell Tumors" Molecular Cancer Research. 2008 pp. 1137-1145 {ten (10) pages).
Lin et al. (Veterinary Immunology and Immunopathology, vol. 127, pp. 114-124, 2009) (Year: 2009).
Lin Tzu-Yin et al., "Targeting canine bladder transitional cell carcinoma with a human bladder cancer-specific ligand", Molecular Cancer, Biomed Central, London, GB, vol. 10, No. 1, Jan. 27, 2011 (Jan. 27, 2011), age 9, XP02108845 9, ISSN: 1476-4598, DOI: 10.1186/1476-4598-10-9.
Magdy Saved Aly et al: "Chromosomal aberrations in early-stage bilharzia! bladder cancer", Cancer Genetics and Cytogenetics., vol. 132, No. 1, Jan. 1, 2002 (Jan. 1, 2002), pp. 41-45, XP055372968, us SSN: 0165-4608, DOI: 10. 1016/S0165-4608(01)00527-1.
Maria I. Stamouli et al: "Detection of genetic alterations in primary bladder carcinoma with dual-color and multiplex fluorescence in situ hybridization", Cancer Genetics and Cytogenetics., vol. 149, No. 2, Mar. 1, 004 (Mar. 1, 2004), pp. 107-113, XP055372972, us ISSN: 0165-4608, DOI: 10. 1016/S0165-4608(03)00303-0.
Marin-Aguilera Mercedes et al: "Utility of Fluorescence in Situ Hybridization as a Non-invasive Technique in he Diagnosis of Upper Urinary Tract Urothelial Carcinoma", European Urology, vol. 51, No. 2, Aug. 22, 2006Aug. 22, 2006), pp. 409-415, XP029850986, ISSN: 0302-2838, DOI: 10.1016/J.EURUR0.2006. 08.045.
Mochizuki, A. et al. "Detection of Copy Number Imbalance in Canine Urothelial Carcinoma With Droplet Digital Polymerase Chain Reaction" Oncology-Original Article. Veterinary Pathology_ 2016, vol. 53(4) pp. 764-772 (nine (9) pages).
Modiano et al., "Predictive value of p16 or Rb inactivation in a model of naturally occurring canine non-Hodgkin's lymphoma," Leukemia, vol. 21, No. 1 pp. 184-187 (2007).
Mullins et al. "Agreement in Breast Cancer Classification between Microarray and Quantitative Reverse Transcription PCR from Fresh-Frozen and Formalin-Fixed, Paraffin-Embedded Tissues" Clin Chem. 53(7): 1273-1279 (2007).
Mutsaers, A.J., W.R. Widmer, and D.W. Knapp, Canine transitional cell carcinoma. J Vet Intern Med, 2003. 17(2): p. 136-44.
Notice of Allowance corresponding to Japanese Patent Application No. 2016-554527 dated Feb. 5, 2019.
Notice of Allowance corresponding to U.S. Appl. No. 15/037,438 dated Jun. 7, 2019.
Notification Concerning Transmittal of International Preliminary Report on Patentability (Chapter I of the Patent Cooperation Treaty) corresponding to International Patent Application No. PCT/US2010/060292 dated Aug. 30, 2012.
Notification of Transmittal of the International Search Report and the Written Opinion of the International Searching Authority, or the Declaration corresponding to International Patent Application No. PCT/US2010/060292 dated Apr. 10, 2012.

Office Action correponding to Canadian Patent Application No. 2,785,999 dated Aug. 16, 2016.
Office Action corresponding to Japanese Patent Application No. 2016-554527 dated Sep. 25, 2018. (Translation).
Office Action corresponding to U.S. Appl. No. 13/515,614 dated Jul. 30, 2014.
Office Action corresponding to U.S. Appl. No. 15/037,438 dated Aug. 15, 2017.
Office Action corresponding to U.S. Appl. No. 15/037,438 dated Jan. 8, 2019.
Office Action corresponding to U.S. Appl. No. 15/037,438 dated May 23, 2018.
Office Action corresponding to U.S. Appl. No. 15/037,438 dated Nov. 24, 2017.
Office Action corresponding with European Patent Application No. 10861217.7-1403 dated Apr. 25, 2014.
Office Action corresponding with European Patent Application No. 14861374.8-1118 dated Apr. 4, 2019.
Oral Summons corresponding with European Patent Application No. 10861217.7-1403 dated Jun. 12, 2015.
Ratcliffe et al., "Proteomic identification and profiling of canine lymphoma patients," Veterinary and Comparative Oncology. vol. 7, No. 2 pp. 92-105 (2009).
Roode, Sarah Culvar.; "Molecular Characterization of Canine Leukemia—Comparative Value and Clinical Applications," A dissertation submitted to the Graduate Faculty of North Carolina State University in partial fulfillment of the requirements for the degree of Doctor of Philosophy; Raleigh, North Carolina, 2014.
Sailasuta, A. et al. "The Relevance of CD117-Immunocythochemistry Staining Patterns to Mutational Exon-11 in c-kit Detected by PCR from Fine-Needle Aspirated Canine Mast Cell Tumor Cells" Veterinary Medicine International, vol. 2014. pp. 1-8 (eight (8)pages).
Seiser et al. "Reading between the lines: molecular characterization of five widely used canine lymphoid tumour cell lines." Veterinary and comparative oncology 11(1): 30-50 (2013).
Sotirakopolous et al.: "Evaluation of Microsatellite Instability in Urine for the Diagnosis of Transitional Cell Carcinoma of the Lower Urinary Tract in Dogs", J Vet Med, 24: 1445-1451 (2010).
Supplementary material for Thomas R, et al.; "Refining tumor-associated aneuploidy through 'genomic recoding' of recurrent DNA copy number aberrations in 150 canine non-Hodgkin lymphomas," Leukemia & Lymphoma, 2011.
Thomas et al., (Chromosome Research, vol. 10, Apr. 1, 2009 (Year: 2009).
Thomas et al., "A canine cancer-gene microarray for CGH analysis of tumors," Cytogenetic and Genome Research, vol. 102, No. 1-4, pp. 254-260 (2003).
Thomas et al., "A Cytogenetically Characterized, Genome-Anchored 10-M b BAC Set and CGH Array for the Domestic Dog", Journal of Heredity., vol. 98, No. 5, Jul. 23, 2007 (Jul. 23, 2007), pp. 474-484, XP055343142,3B ISSN: 0022-1503, DOI: 10.1093/jhered/esm053.
Thomas et al., "Chromosome aberrations in canine multicentric lymphomas detected with comparative genomic hybridisation and a panel of single locus probes," British Journal of Cancer. vol. 89, No. 8, pp. 1530-1537 (2003).
Thomas, Chromosome Res, vol. 22, No. 3, pp. 305-319, 2017 (Year: 2014).
Thomas, R., et al. "A genome assembly-integrated dog 1 Mb BAC microarray: a cytogenetic resource for canine cancer studies and comparative genomic analysis." Cytogenetic and genome research 122(2): 110-121 (2008).
Urovysion Bladder Cancer Kit; <http://www.abbottmolecular.com> Accessed Nov. 11, 2013.
Urovysion Bladder Cancer Kit; Package Insert; Abbott Laboratories, 2006.
Winkler et al. (2006) Polysomy 13 in a canine prostate carcinoma underlining its significance in the development of prostate cancer. Cancer Genet. Cytogenet. 169:154-158.

* cited by examiner

METHOD TO DIAGNOSE MALIGNANT MELANOMA IN THE DOMESTIC DOG

CROSS REFERENCE TO RELATED APPLICATIONS

This application is a § 371 U.S. National Stage of International Application PCT/US2015/041988, filed Jul. 24, 2015, which claims the benefit of U.S. Provisional No. 62/028,644 filed Jul. 24, 2014, Breen, METHOD TO DIAGNOSE MALIGNANT MELANOMA IN THE DOMESTIC DOG, which is hereby incorporated by reference in their entireties.

1. FIELD

The present disclosure provides an improved method to diagnose malignant melanoma of the oral cavity in the dog and differentiate from other lesions.

2. BACKGROUND

2.1. Introduction

Melanocytes are melanin-producing cells, usually found in the basal layer of the epidermis. The primary function of these cells is to protect the nuclei of neighboring epithelial cells from UV-damage, but they also can give rise to both benign melanocytomas and malignant melanomas. The American Veterinary Medical Association estimates that 4.2 million dogs are diagnosed with cancer each year in the US. Key opinion leaders estimate that malignant oral melanomas account for up to half of the ~200,000 cases all oral cancers diagnosed in the domestic dog each year in the USA. It has been estimated that as many as 90% of oral melanoma are malignant, and have a high metastatic propensity to spread to regional bone, lymph nodes, tonsils, and lungs (Bergman et al. 2007; Koenig et al. 2002; Ramos-Vara et al. 2000; Spangler & Kass 2006). Almost two thirds of oral melanomas contain melanin, a feature that aids the differential diagnosis of a biopsy specimen when evaluated by a veterinary pathologist. For the cases that lack pigmentation (~⅓ lack melanin) diagnosis is more challenging. In general melanomas respond poorly to standard chemotherapeutic treatments (Bergman et al. 2007) and with the high metastatic potential, prognosis is guarded.

Melanomas of the cutaneous epithelium are the third most common skin lesion in dogs (Villamil et al. 2011) representing 5-11% of all malignant melanomas (Smith et al. 2002). In general most cutaneous melanomas in the dog are considered benign.

There is ongoing debate among veterinary pathologists regarding the accuracy of prognostic criteria for canine malignant melanomas (Withrow 2013). In veterinary medicine, several retrospective studies investigated the possible correlation(s) between prognosis and physical characteristics of the tumor; including gender, anatomical site, volume of tumor, and histological parameters such as pigmentation and mitotic index (Kudnig et al 2003; Overly et al. 2001; Ramos-Vara et al. 2000; Spangler & Kass 2006). In a study of 122 canine melanocytic tumors, mitotic index and anatomical site, regarded as markers of malignancy, were not significantly correlated with survival time (Ramos-Vara et al. 2000). A later study of 384 cases of melanocytic tumors identified significant correlation of metastasis, mitotic index, nuclear atypia, WHO clinical stage, and volume with decreased patient survival (Spangler & Kass 2006). However, the same study also reported that only 59% of cases determined to be histologically malignant also exhibited features of biological malignancy (metastases or recurrence). It was determined that 74% of tumors of "ambiguous location" (feet or lips) were reported as malignant by histologic evaluation, but only 38% of these cases actually demonstrated malignant behavior. Finally, of 227 melanocytic skin lesions, predominantly thought to be benign, 39% were reported as histologically malignant, with only 12% exhibiting characteristics of malignant behavior (Spangler & Kass 2006).

In summary previous studies of canine melanocytic lesions all indicate that that there is a need for more accurate diagnostic and prognostic markers in canine melanoma.

3. SUMMARY OF THE DISCLOSURE

The inventors discovered methods for diagnosis of a malignant mucosal melanoma in the domestic dog and for distinguishing malignant mucosal melanoma of the canine mucosa from other masses located in the oral cavity of the domestic dog. Dogs with a confirmed diagnosis of a malignant oral melanoma frequently present with a characteristic DNA copy number profile including events located on dog chromosome (CFA) 10 and 30. Detection of the specific copy number profiles of CFA 10 and/or 30 provides a means to confirm a diagnosis of a malignant oral melanoma.

In particular non-limiting embodiments, the present invention provides a method detecting a canine malignant oral melanoma in a biological sample from a dog which comprises: measuring copy numbers of regions of canfam2 CFA10:5, CFA 10:14, CFA 10:20, CFA 30:9 and CFA 30:19 in the biological sample; comparing the measured copy numbers to those of appropriate controls; and if the copy numbers of regions of CFA 10:5, CFA 10:14, CFA 30:19 are increased and the copy numbers of regions of CFA 10:20 and CFA 30:9 are reduced from that of the appropriate controls, determining that the biological specimen from which the cells/DNA were derived represents a canine malignant oral melanoma.

In one embodiment, for diploid cells the copy number increases may be >2.0, >3.0, >4.0. Alternatively, the copy number reductions may <2.0, e.g., 1.0 or 0. Both the copy number increases may be >2.0 and the copy number reductions are <2.0. Copy number increases are those where, in individual cells the number of copies of the targeted region is >2 and losses where the number of copies of the targeted region are less than 2, i.e., 0 or 1).

In tumor cell populations there is usually some degree of heterogeneity and so when assessing DNA copy number in a population of cells, e.g. by PCR, the copy number determined is actually the mean copy number of the cells in the population. There are several algorithms used to determine a cut-off/threshold of what would be considered indicative of a change in copy number—selection of these should be determined by the method used to detect the changes. For example, array CGH the ADM2 or FASST2 algorithms are used to identify copy number changes, both of which tend to set a threshold based on log 2 ratios of the test:reference signal intensity where >+0.201 is consider a gain and <−0.234 is considered a loss. For analyses of individual cells the copy number must be an integer, where a copy number of 0, 1 are considered a loss and a copy number of 3, 4, 5 etc. are considered gains. In cell population a mean copy number is determined and the presence of loss or gain determined as mentioned above. See also, U.S. Pat. No.

7,960,110 (Bastian and Pinkel, particularly col. 9, lines 20-35), the contents of which are hereby incorporated by reference in its entirety.

The copy numbers may be measured in individual cells by, for example, fluorescence in situ hybridization (FISH), or in cell populations by for example, polymerase chain reaction (PCR), comparative genomic hybridization (CGH) or next generation sequencing.

The biological sample may be a tissue sample, such as a biopsy from an oral lesion. The sample may be a fresh sample, a fresh-frozen sample, a fixed, sample or a fixed paraffin-embedded sample. If a fixed sample, the fixative used could one of several chemical used to preserve the tissue.

The invention also provides a method of identifying dogs for melanoma treatment wherein the dog is suspected of having a melanoma which comprises: measuring a copy number of regions of canfam2 CFA10:5, CFA 10:14, CFA 10:20, CFA 30:9 and CFA 30:19 in the biological sample; comparing the measured copy numbers to those of appropriate canine malignant oral melanoma controls; and if the copy numbers of regions of CFA 10:5, CFA 10:14, CFA 30:19 are increased and the copy numbers of regions of CFA 10:20 and CFA 30:9 are simultaneously reduced from that of the appropriate controls, ruling in the dog for melanoma treatment.

Furthermore, the invention provides a kit for detecting a canine malignant oral melanoma in a biological sample in a dog comprising: at least a plurality of reagents selected from the group consisting of: a nucleic acid probe capable of specifically detecting canfam2 CFA10:5, CFA 10:14, CFA 10:20, CFA 30:9 and CFA 30:19; and instructions for use in measuring a copy number of regions of CFA10:5, CFA 10:14, CFA 10:20, CFA 30:9 and CFA 30:19 in a biological sample from a dog; wherein if the copy numbers of regions of CFA 10:5, CFA 30:19 are increased and the copy numbers of regions of CFA 10:20 and CFA 30:9 are reduced from that of measured copy numbers for appropriate melanoma controls; and determining that the dog has increased likelihood of a canine malignant oral melanoma.

In particular, non-limiting embodiments, the methods and kits of the invention include the use of any pairwise combination, e.g., CFA10:5 & CFA10:14; CFA10:5 & CFA10:20; CFA10:5 & CFA30:9; CFA10:5 & CFA30:19; CFA10:14 & CFA10:20; CFA10:14 & CFA30:9; CFA10:14 & CFA30:19; CFA10:20 & CFA30:9; CFA10:20 & CFA30:19; or CFA30:9 & CFA30:19. Alternatively, the invention includes any ternary combinations of the five regions, e.g. CFA10:5, CFA10:14 & CFA10:20; CFA10:5, CFA10:14 & CFA30:9; CFA10:5, CFA10:14 & CFA30:19; CFA10:5, CFA10:20 & CFA30:9; CFA10:5, CFA10:20 & CFA30:19; CFA10:5, CFA30:9 & CFA30:19; CFA10:14, CFA10:20 & CFA30:9; CFA10:14, CFA10:20 & CFA30:19; CFA10:14, CFA30:9 & CFA30:19; or CFA 10:20, CFA30:9 & CFA30:19. Furthermore, the invention includes and four way combinations, e.g., CFA10:5, CFA10:14, CFA10:20, & CFA 30:9; CFA10:5, CFA10:14, CFA10:20 & CFA 30:19; CFA10:5, CFA10:14, CFA 30:9 & CFA 30:19; CFA10:5, CFA10:20, CFA 30:9 & CFA 30:19; or CFA10:14, CFA10:20, CFA 30:9, & CFA 30:19.

The present invention provides methods for detecting a canine malignant oral melanoma in a biological sample from a dog, which comprises: measuring the copy number status of three genomic intervals, including, but not limited to, regions on CFA 10 surrounding either ~5 Mb (CFA10:5) and/or ~14 Mb (CFA10:14), and also at the region surrounding ~20 Mb (CFA10:20), and/or two regions on CFA 30, including regions surrounding ~9 Mb (CFA30:9) and ~19 Mb (CFA30:19 Mb), provide data that identify if the specimen being evaluated is from a canine malignant melanoma, using either of the following example algorithms; (cMEL1) if the copy number status of CFA10:5 and/or CFA10:14 are considered a gain (n>2.0) and if the copy number status of CFA10:20 is considered a loss (n<2.0).

The specimen from which the DNA was isolated is a malignant melanoma.

(cMEL2) if the copy number status of CFA30:9 is consider a loss (n<2.0) and if the copy number of CFA30:19 is consider a gain (n>2.0).

The specimen from which the DNA was isolated is a malignant melanoma.

The regions referred to represent base pair coordinates in the canfam2 build of the canine genome assembly (as of April 2014). As the assembly is refined it is possible that the precise coordinates will move. Genes located with the defined regions of canfam2 as of April 2014 are shown in the examples section of this disclosure.

Sensitivity:

When applied to the cohort of 39 confirmed cases of canine malignant melanoma used in the present invention, 14 cases (36%) were scored as melanoma with cMEL1 and 24 case (62%) were scored as melanoma with cMEL2.

Specificity:

The algorithm cMEL2 was applied to genome wide DNA copy data for 100 non-neoplastic control specimens from the dog and the proportion of cases falsely reported as melanoma was 0%. Assessment of over 250 lymphoid malignancies also indicated that 0% of such cases met the criteria to be classified as a melanoma. Analysis of almost 400 other common canine solid tumors (Table 1) revealed only 0.5% would be falsely scored as malignant melanoma using cMEL2. [NOTE: this small percentage in canine solid tumors is due the high complexity of genomic changes in both osteosarcoma and histiocytic sarcoma, neither of which would be likely to be confused with melanoma if located in the oral cavity of a dog].

These data indicate that the assessment for copy number loss of CFA 30:9 and simultaneous copy number gain of CFA30:19, using cMEL2, is highly specific for diagnosis of a canine malignant oral melanoma.

TABLE 1

Use of the algorithm cMEL2 in oral melanomas, bening melanocytomas and other solid tumors in the dog located in either the oral cavity or elsewhere on the body. The non-melanoma oral lesions include canine squamous cell carcinomas, ameloblastomas, calcifying epithelial odontogenic tumors, (CEOT) and epulides.

| Canine cancer/mass | Number evaluated | Number scored positive with cMEL2 | % scored positive with cMEL2 |
|---|---|---|---|
| Malignant oral melanoma | 39 | 24 | 61.54 |
| Benign melanomas | 18 | 0 | 0 |
| Non-melanomas (oral) | 21 | 0 | 0 |
| TOTAL oral lesions | 78 | | |
| Non-melanoma/ non oral lesions (n = 357) | | | |
| Hemangiosarcoma | 108 | 0 | 0 |
| Histiocytic sarcoma | 72 | 1 | 1.39 |
| Osteosarcoma | 44 | 1 | 2.27 |
| Mast cell tumors | 133 | 0 | 0 |
| TOTAL (non malignant melanoma) | 396 | | 0.5% |

With regard to the most likely candidates for a suspected diagnosis of malignant melanoma (melanoma, benign melanoma and amelanotic lesions of the oral cavity), the algorithm cMEL2 has a sensitivity of 61.54% and a specificity of 100%.

Inclusion of the 357 cases representing four additional types of common solid tumor, bring the total number of non-melanoma cases to 396, of which just two were scored as melanoma with the cMEL2 algorithm. These data indicate that with a canine mass of unknown origin, DNA copy number analysis of CFA 30, scored with cMEL2 has a sensitivity of 61.54%, a specificity of 99.49%, a positive likelihood ratio of 121.85 and a negative likelihood ratio of 0.39.

The disclosure also provides a method of evaluating a melanoma prognosis in a sample from a dog comprising: (a) detecting copy number status of two or more regions of CFA 10 and/or CFA 30 in cell nuclei or a nucleic acid sample obtained from tumor specimen of the dog, by a nucleic acid hybridization assay with nucleic acids specific for CFA 10 and CFA 30; (b) comparing the detected levels of copy numbers to at least one sample from a training set(s), wherein a sample training set(s) comprises data of the copy numbers from a reference sample, and the comparing step comprises applying a statistical algorithm which comprises determining a correlation between the copy number from the sample from the dog and the copy number from at least one training set(s); and (c) evaluating the melanoma prognosis of the dog based on the detected copy number status and the results of the statistical algorithm.

4. BRIEF DESCRIPTION OF THE FIGURES

FIG. 1. Ideograms dog chromosome (CFA) 10 (left) and 30 (right) showing whole chromosome penetrance plots of the distribution of copy number losses (profiles to left) and gains (profiles to right) in DNA samples prepared from tissue biopsy specimens of confirmed cases (n=39) of canine malignant oral melanomas.

Figures 1, 2:
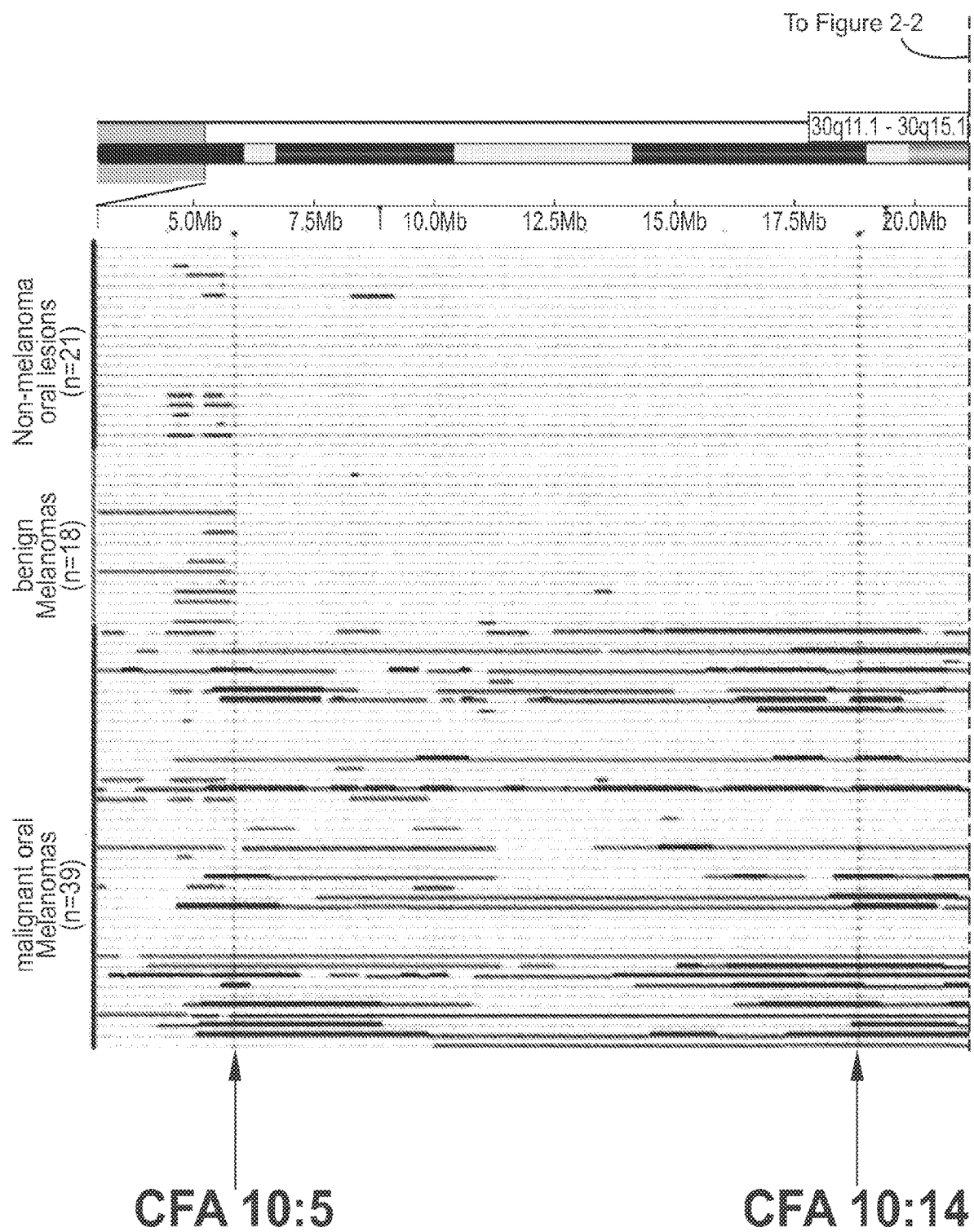
Figure 2:
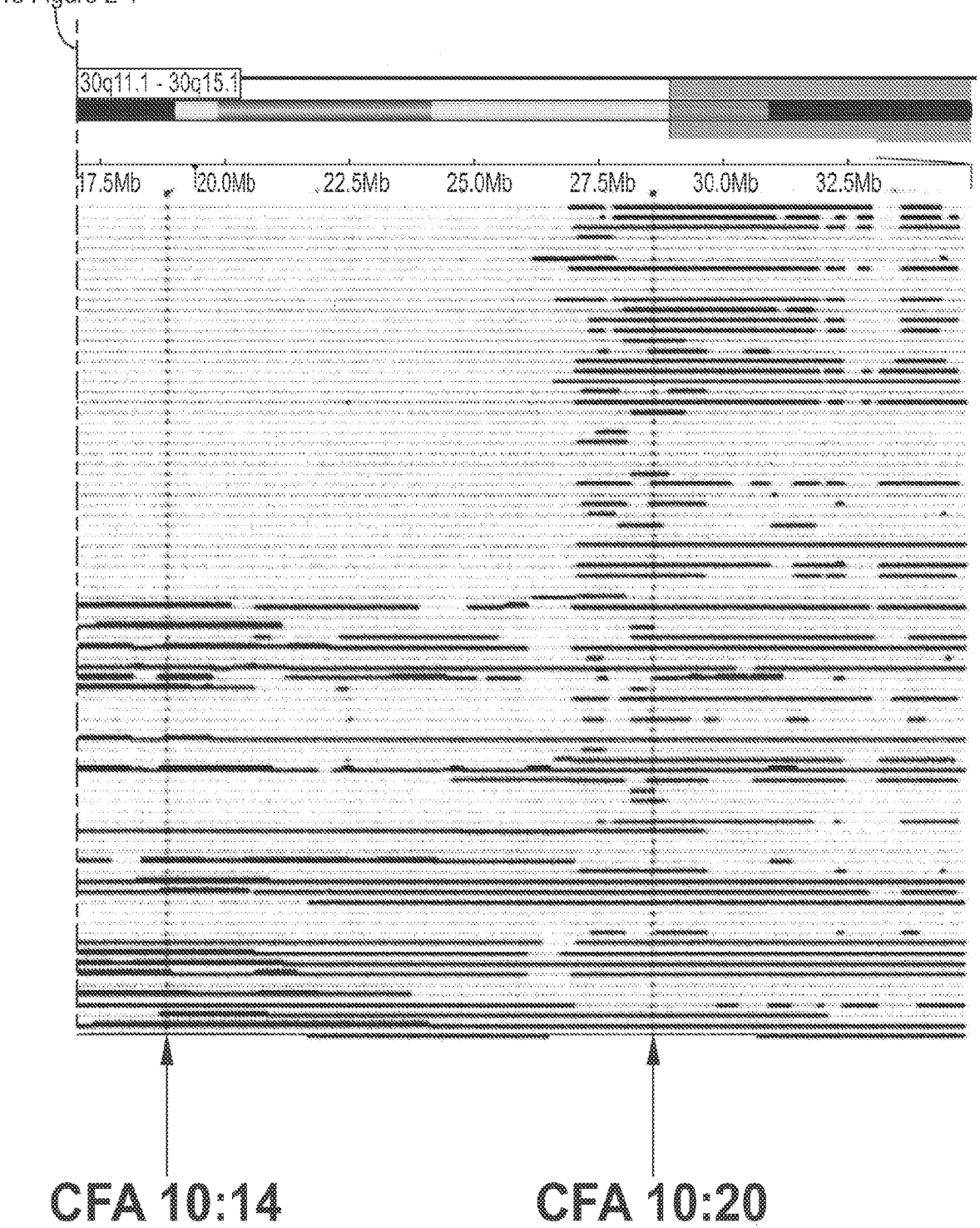

FIG. 2. DNA copy number status of dog chromosome 10 spanning the region denoted in canfam2 as 4 Mb-25 Mb.

Figures 1, 3:
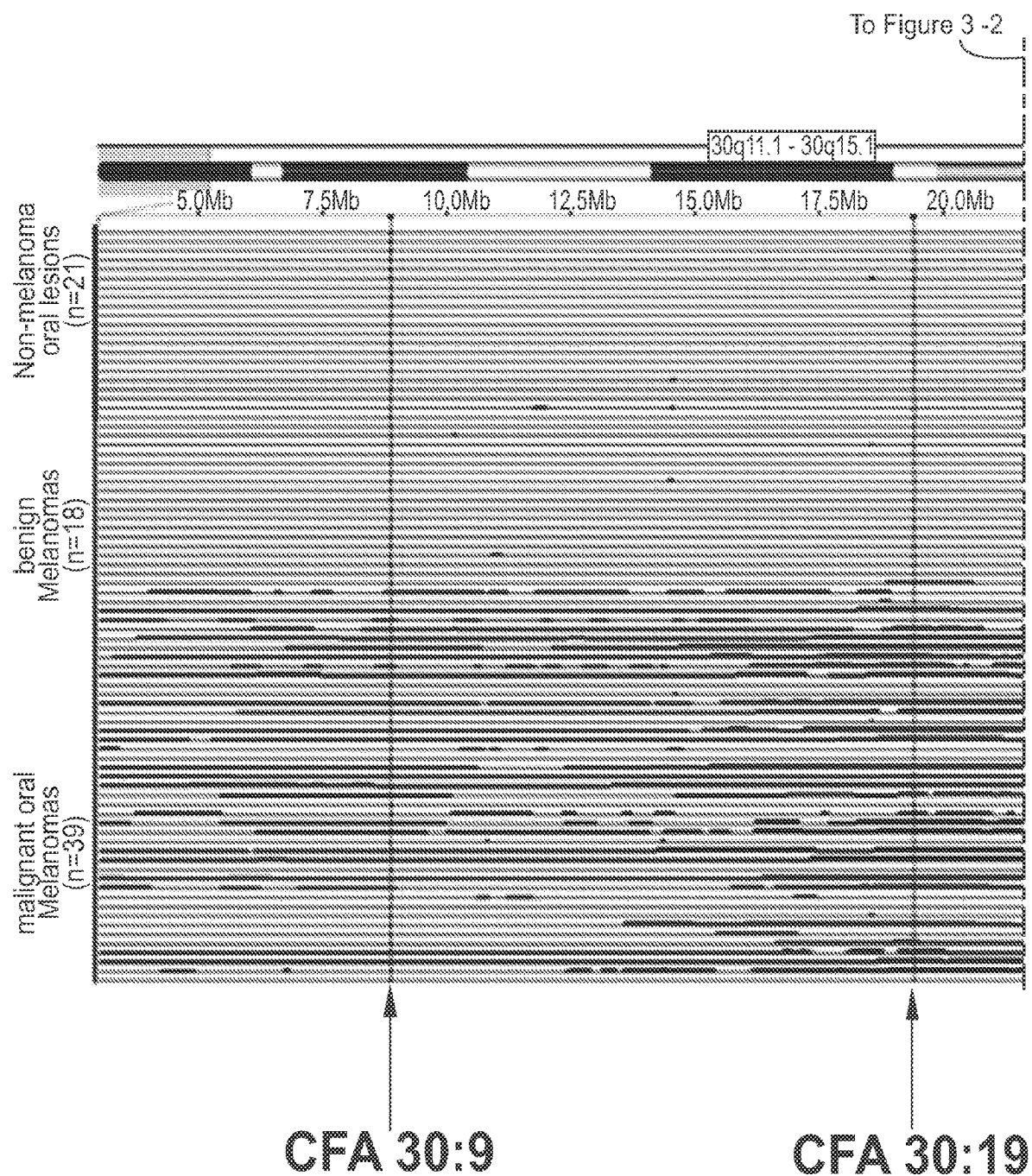
Figures 2, 3:
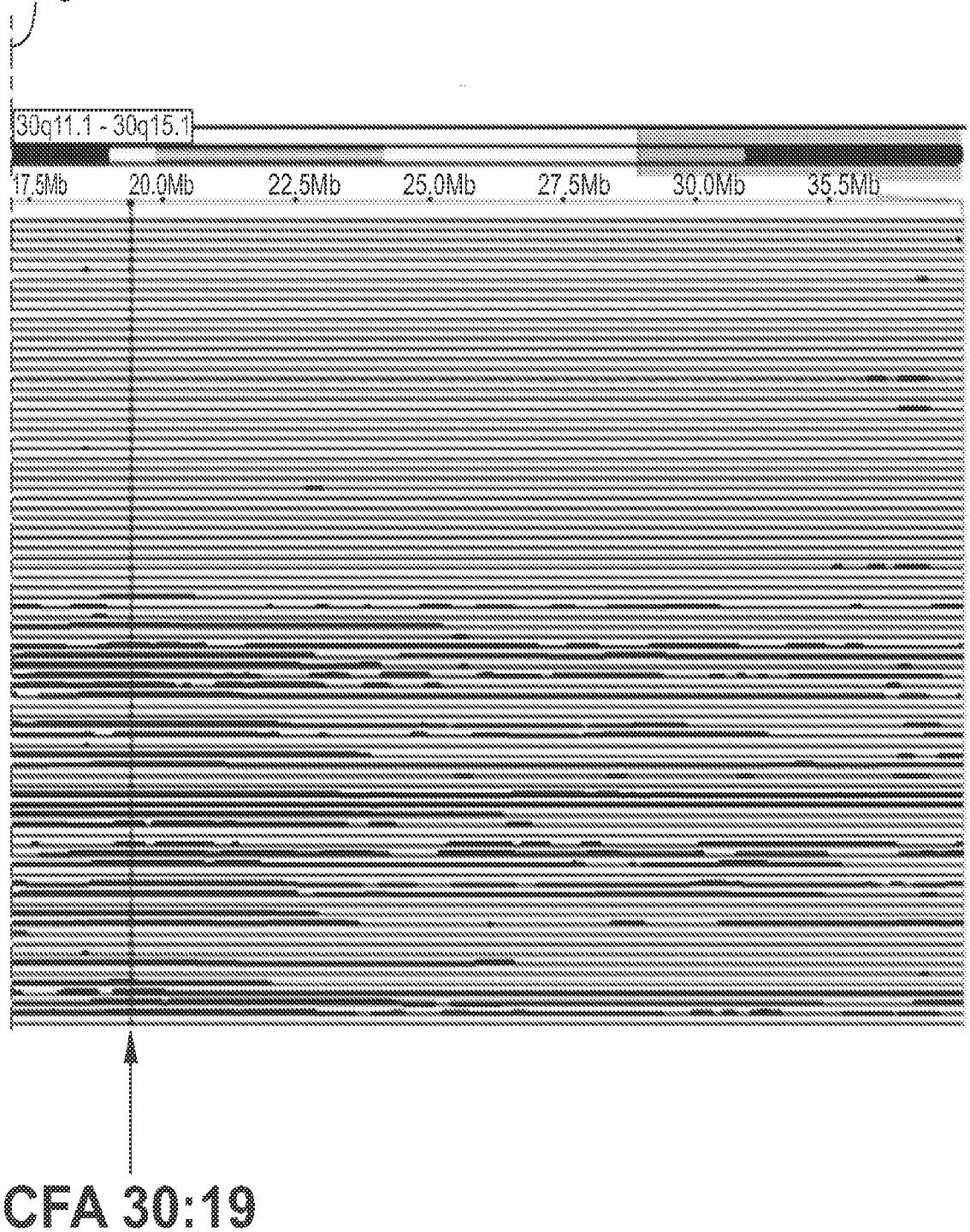

FIG. 3. DNA copy number status of dog chromosome 30 spanning the region denoted in canfam2 as 5 Mb to almost 30 Mb.

Figures 1, 4:
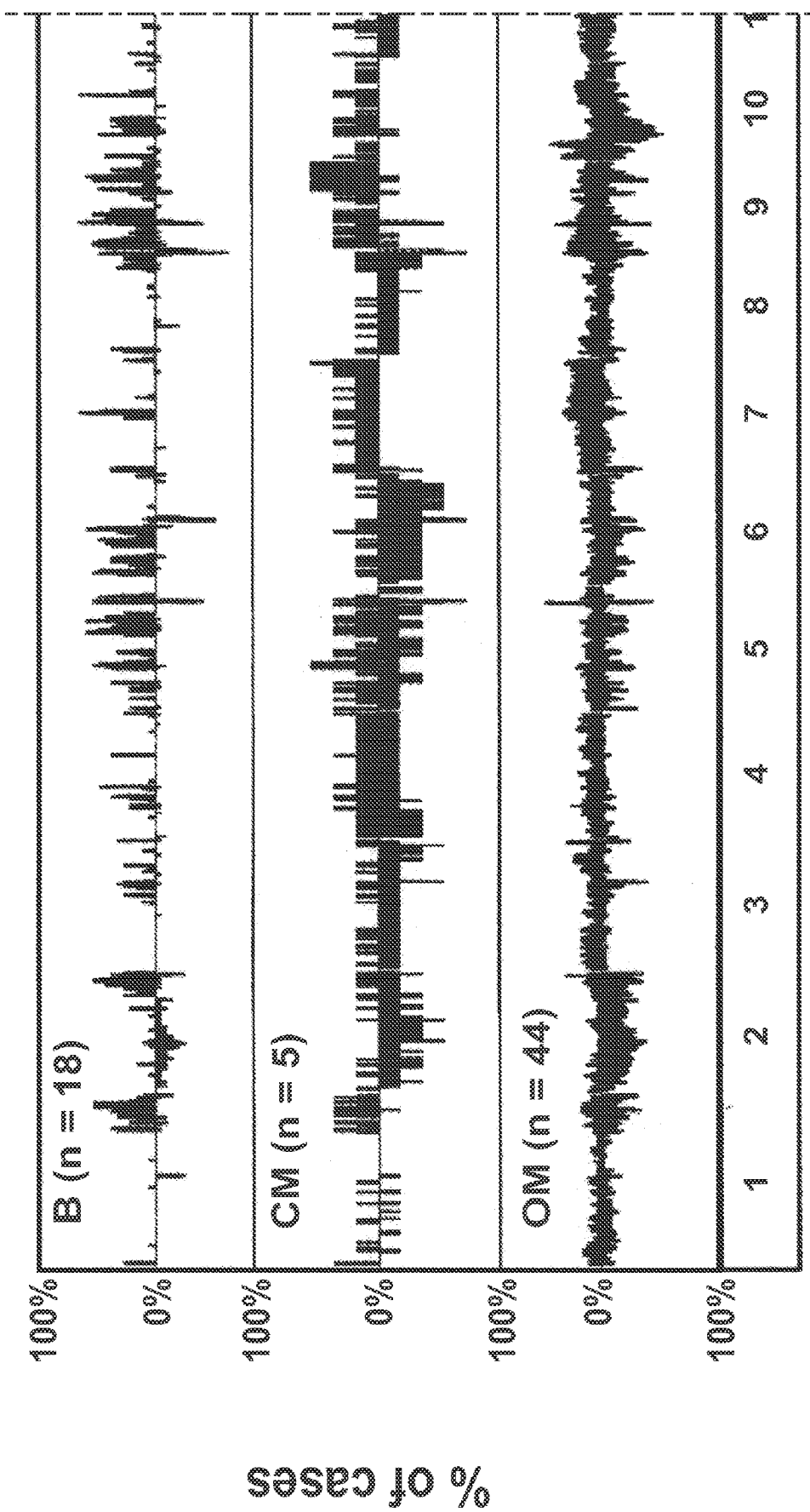
Figures 2, 4:
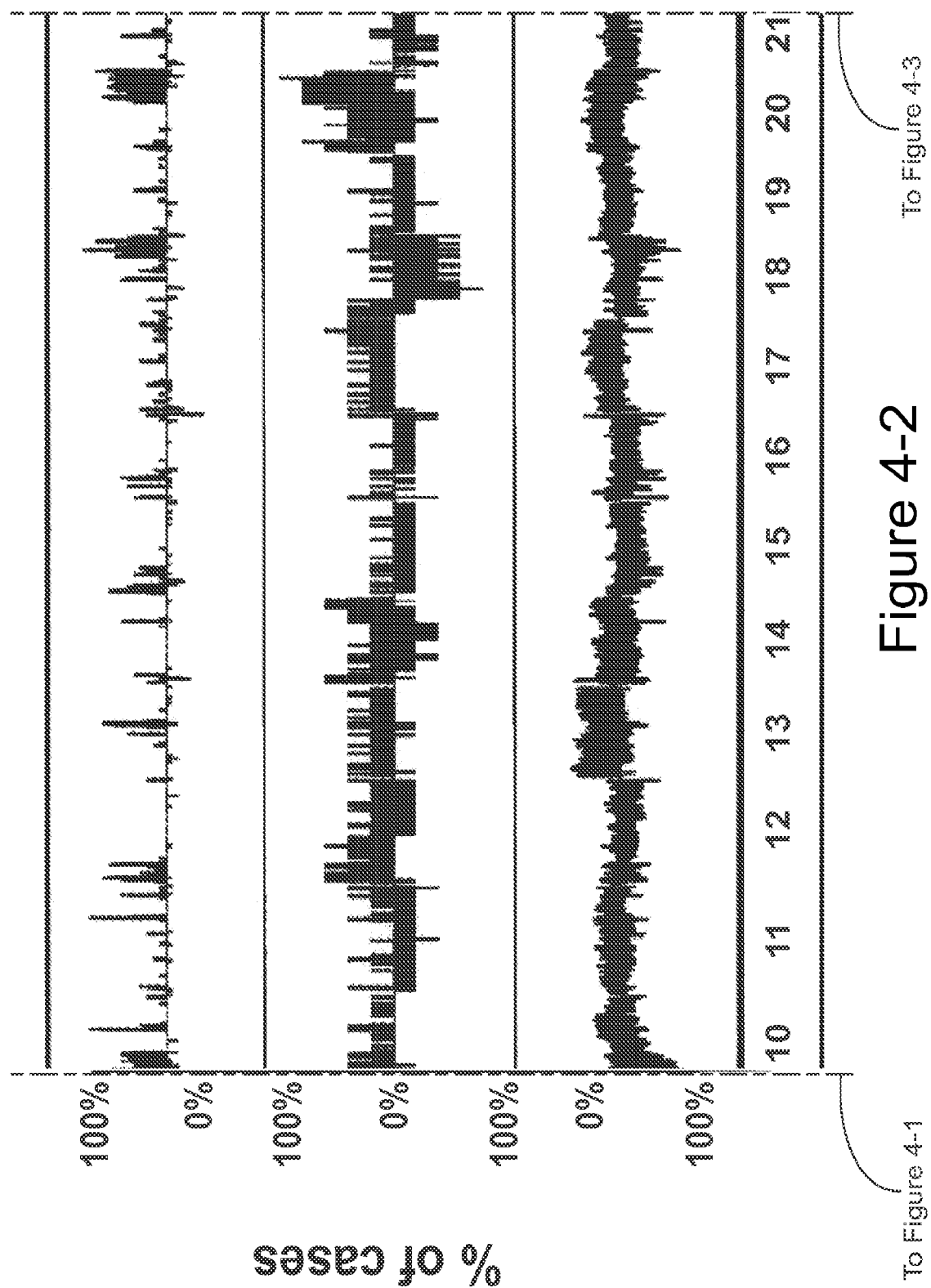
Figures 3, 4:
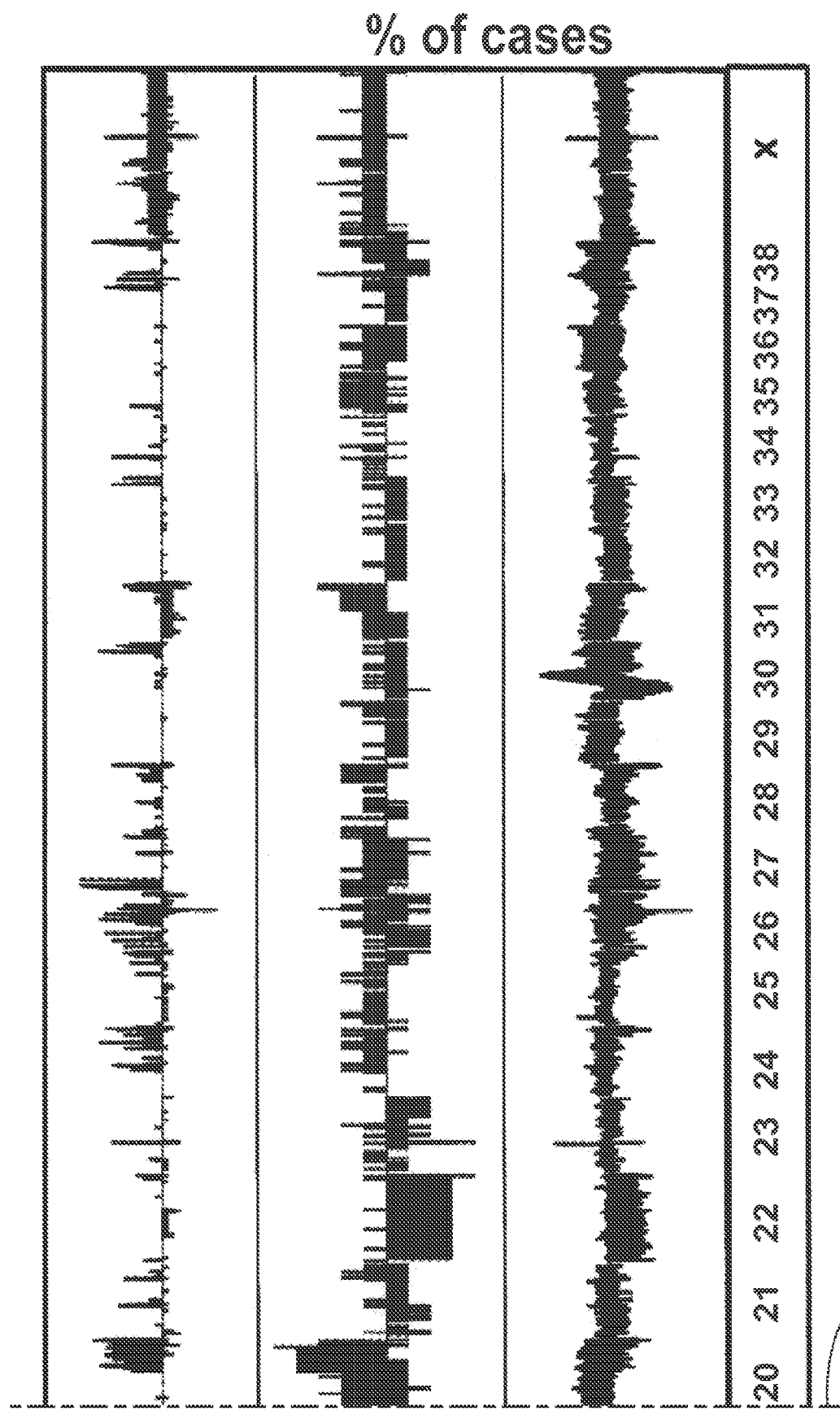

FIG. 4. aCGH analysis of primary canine oral melanoma (OM), primary canine cutaneous melanoma (CM) and canine cutaneous melanocytoma (B).

Figures 1, 5:
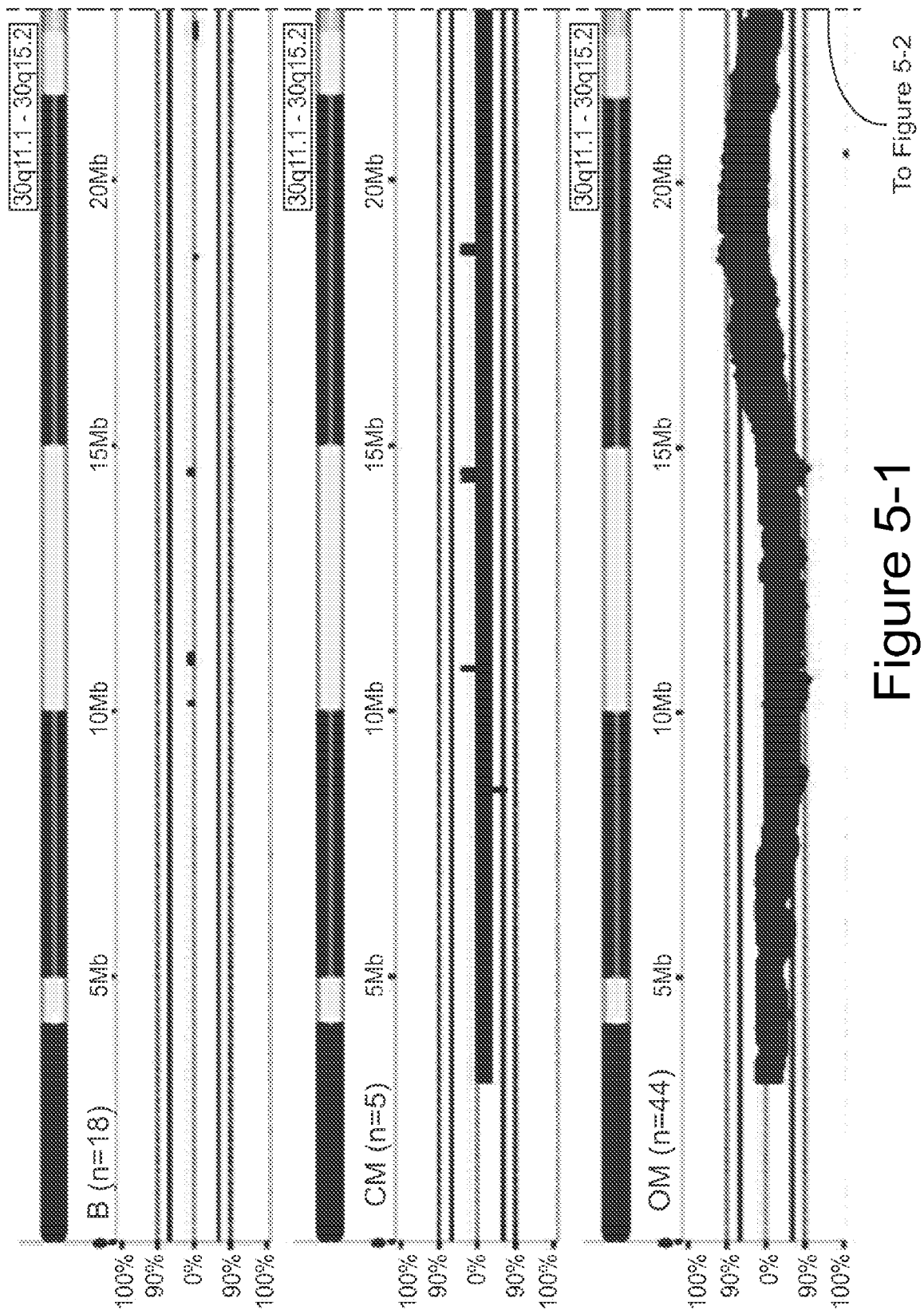
Figures 2, 5:
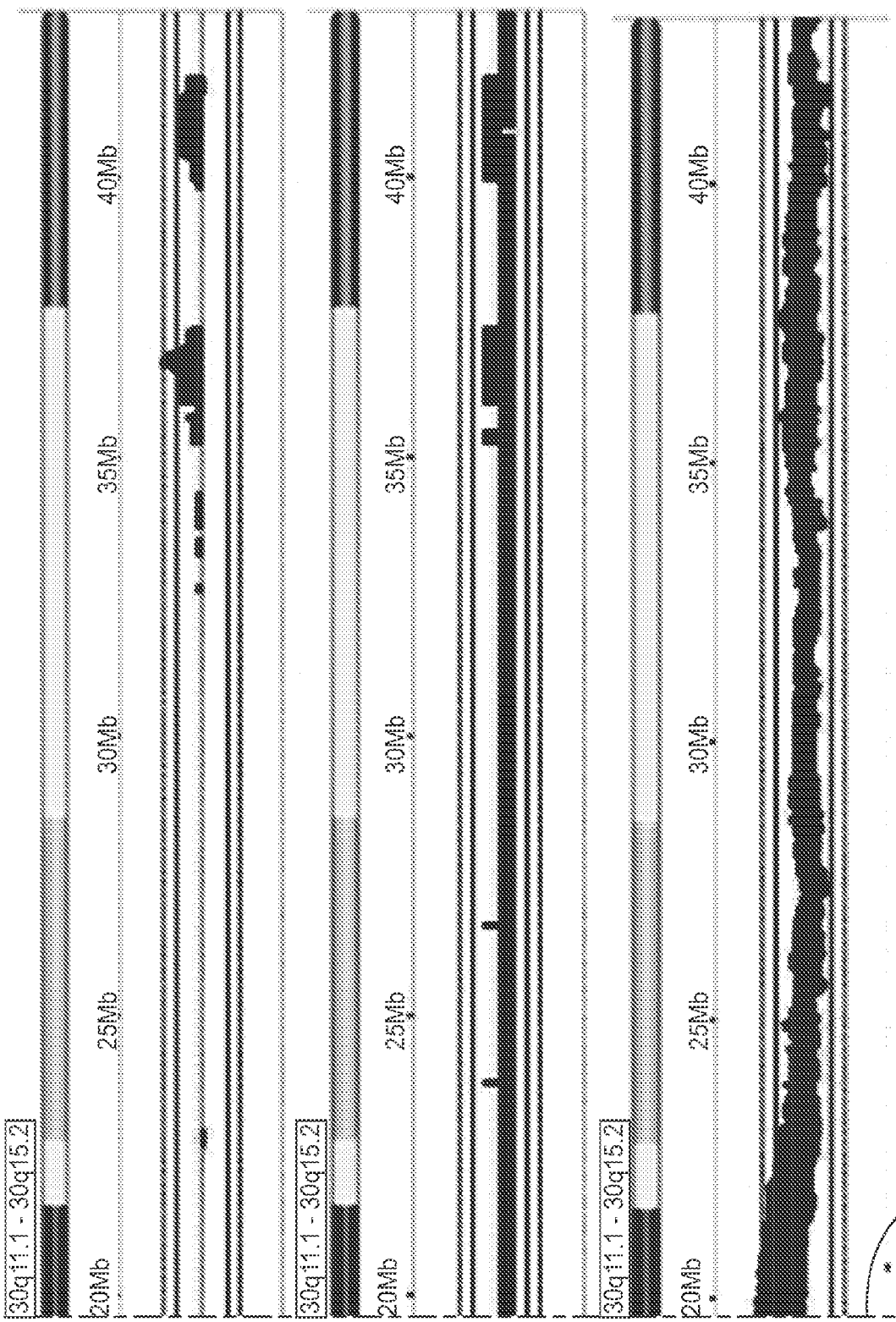

FIG. 5. Penetrance plots of DNA copy number aberrations along the length of CFA chromosome 30 in oral melanomas (OM), cutaneous melanomas (CM) and melanocytomas (B).

Figures 1, 6:
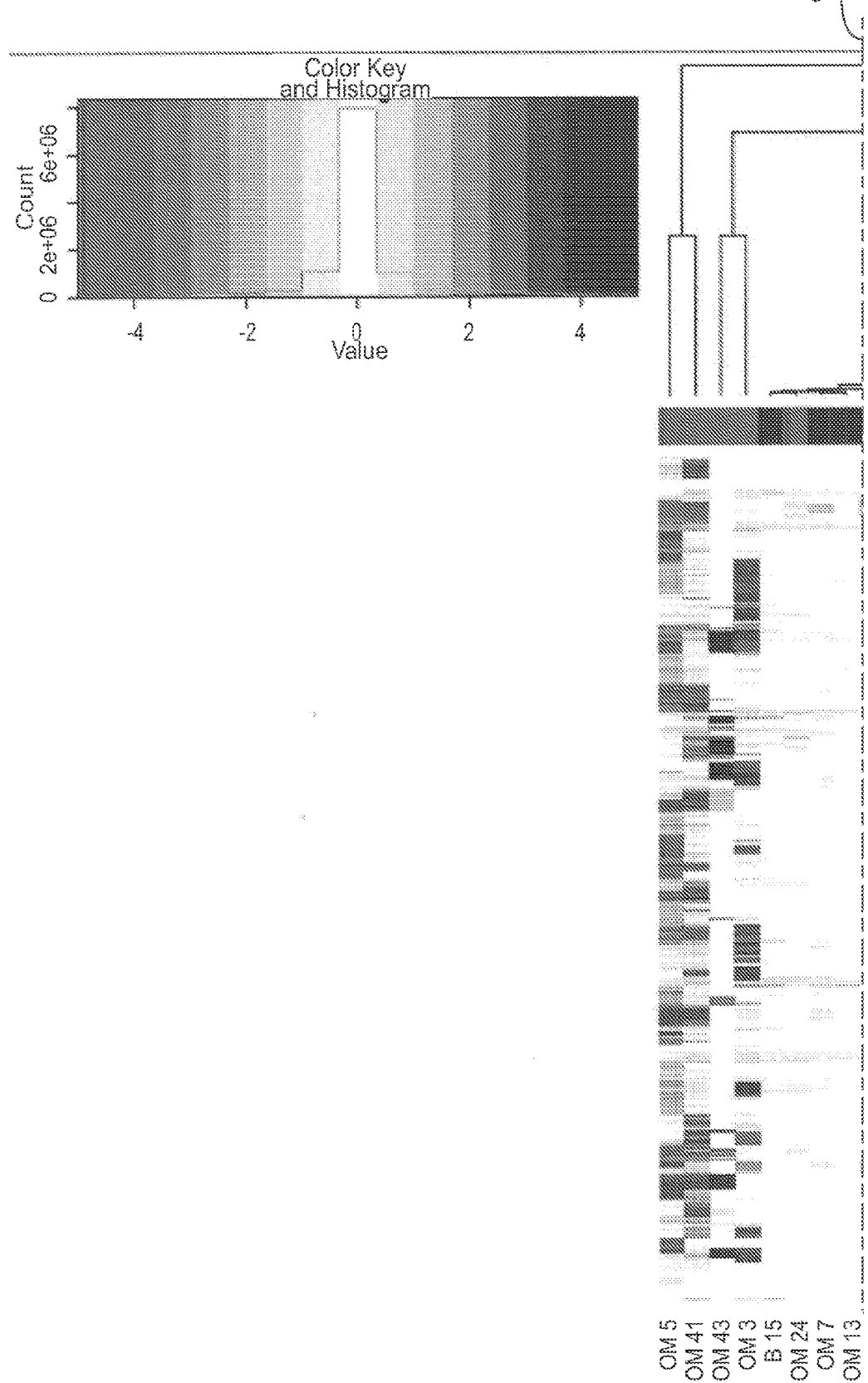
Figures 2, 6:
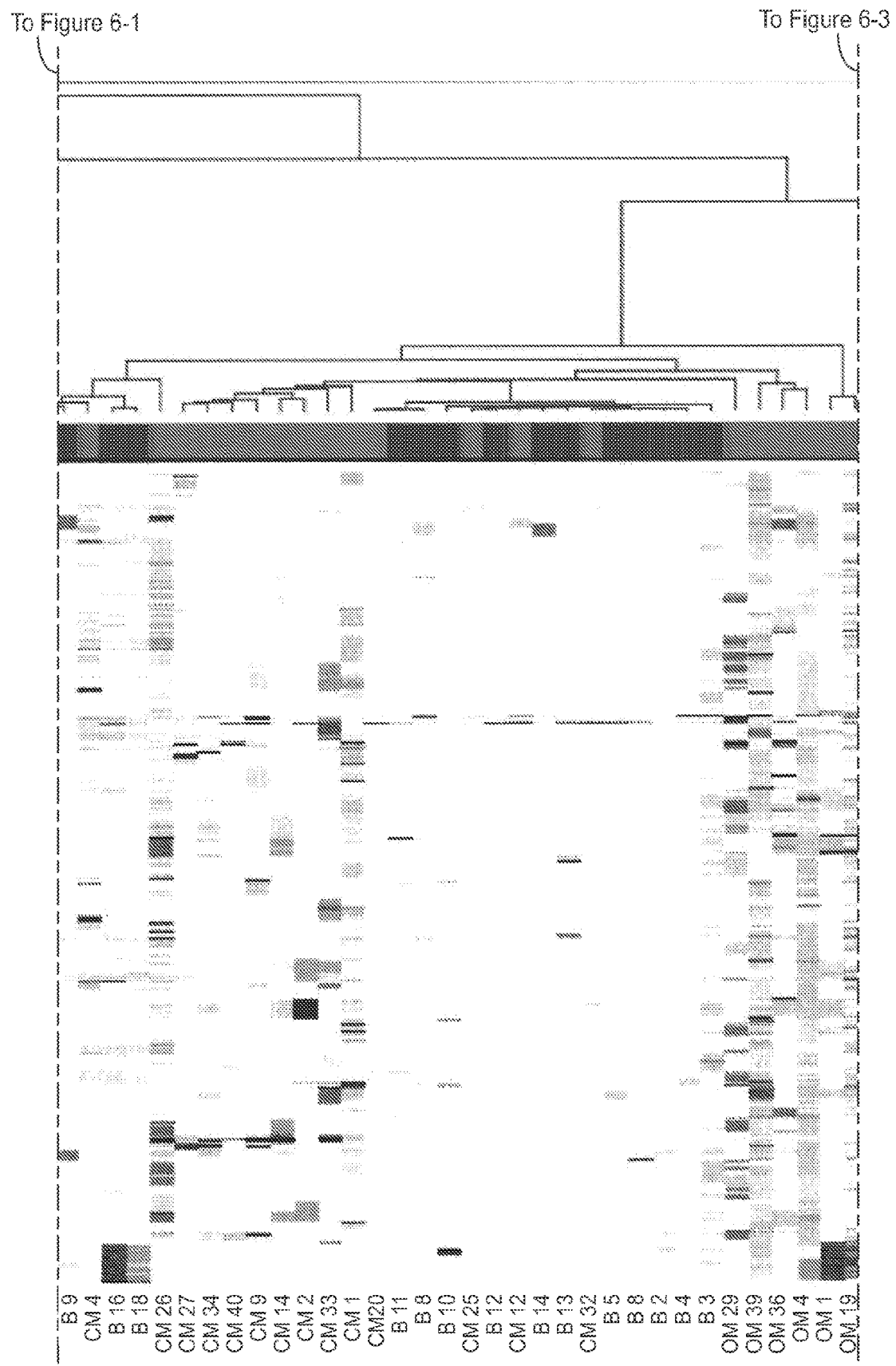
Figures 3, 6:
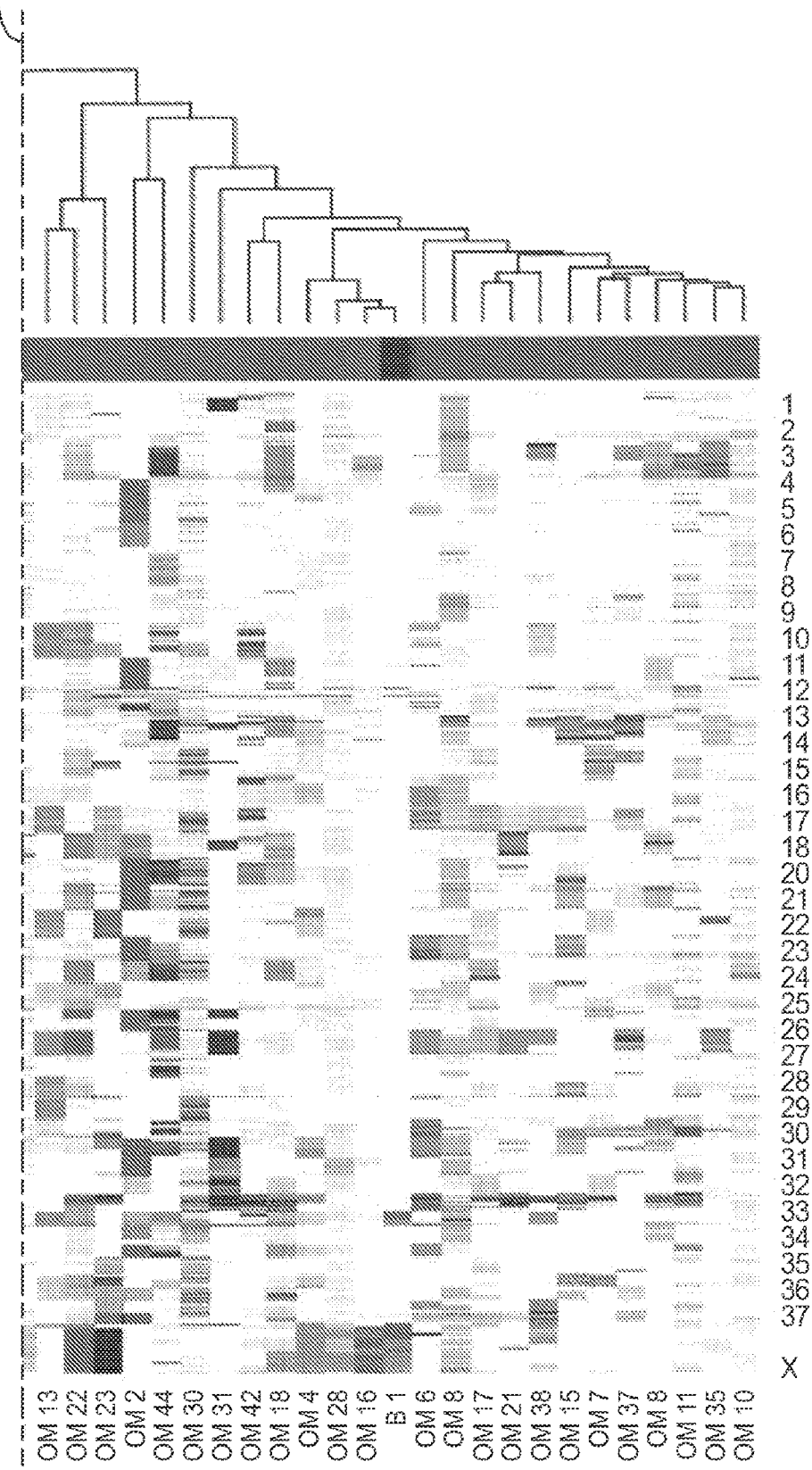

FIG. 6. Clustering analysis of 31 cases of primary canine oral melanoma, five cases of primary canine cutaneous melanoma, and 15 primary canine melanocytomas based on genome-wide oaCGH profiles.

Figure 7A:
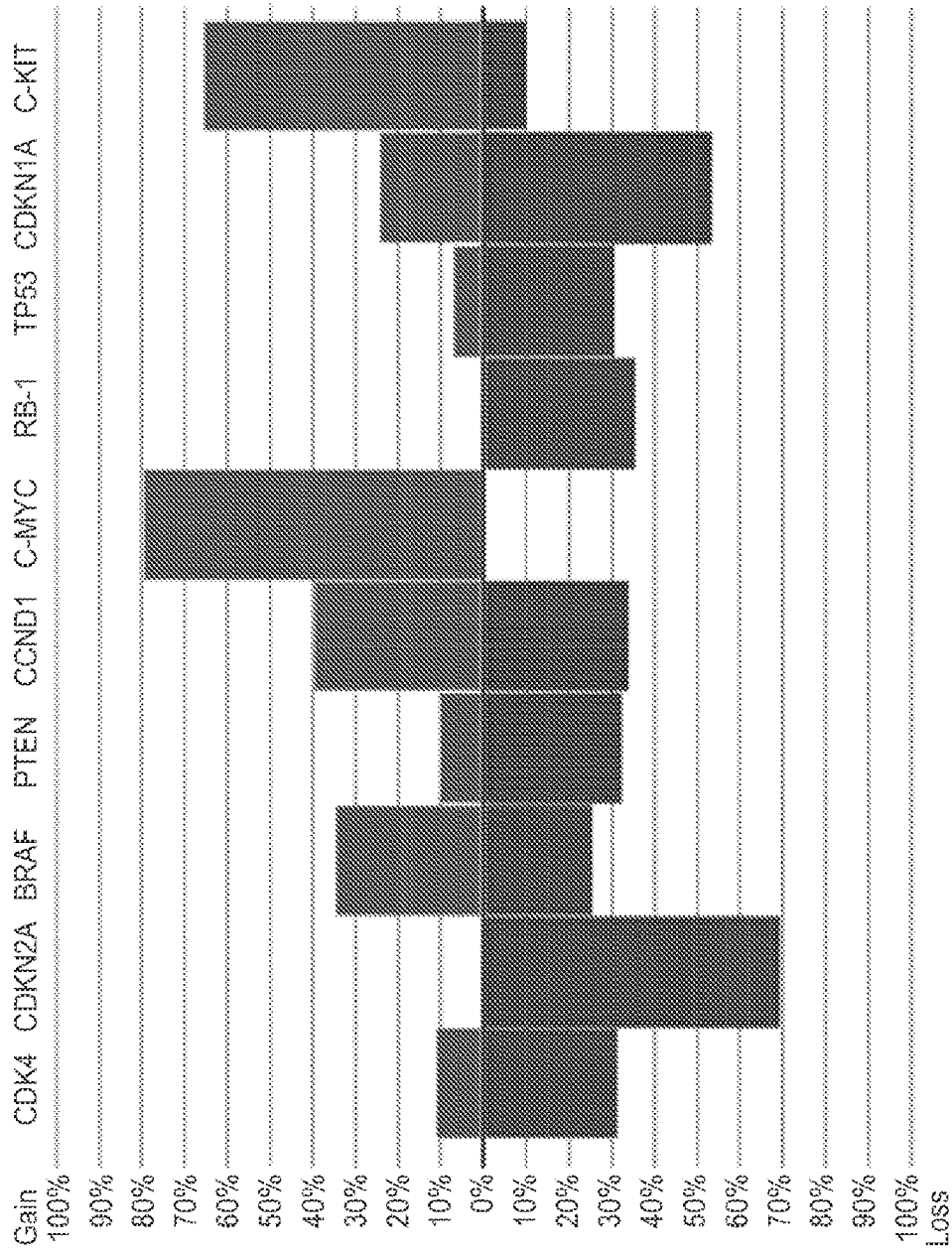
Figure 7B:
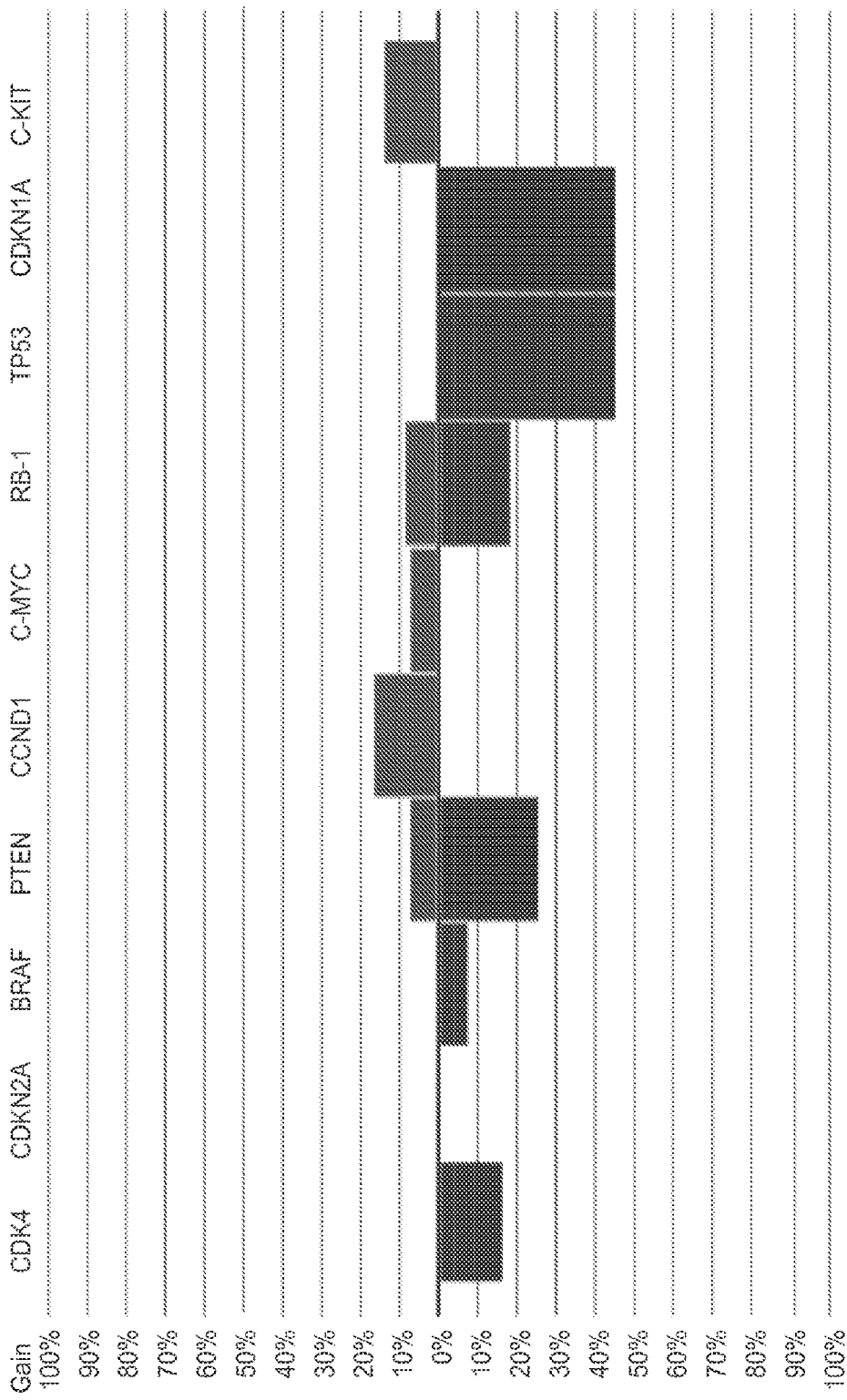

FIG. 7A and FIG. 7B. Penetrance of aberration of 10 specific genomic regions in (7A) primary canine oral melanoma and (7B) canine melanocytoma.

Figures 1, 8:
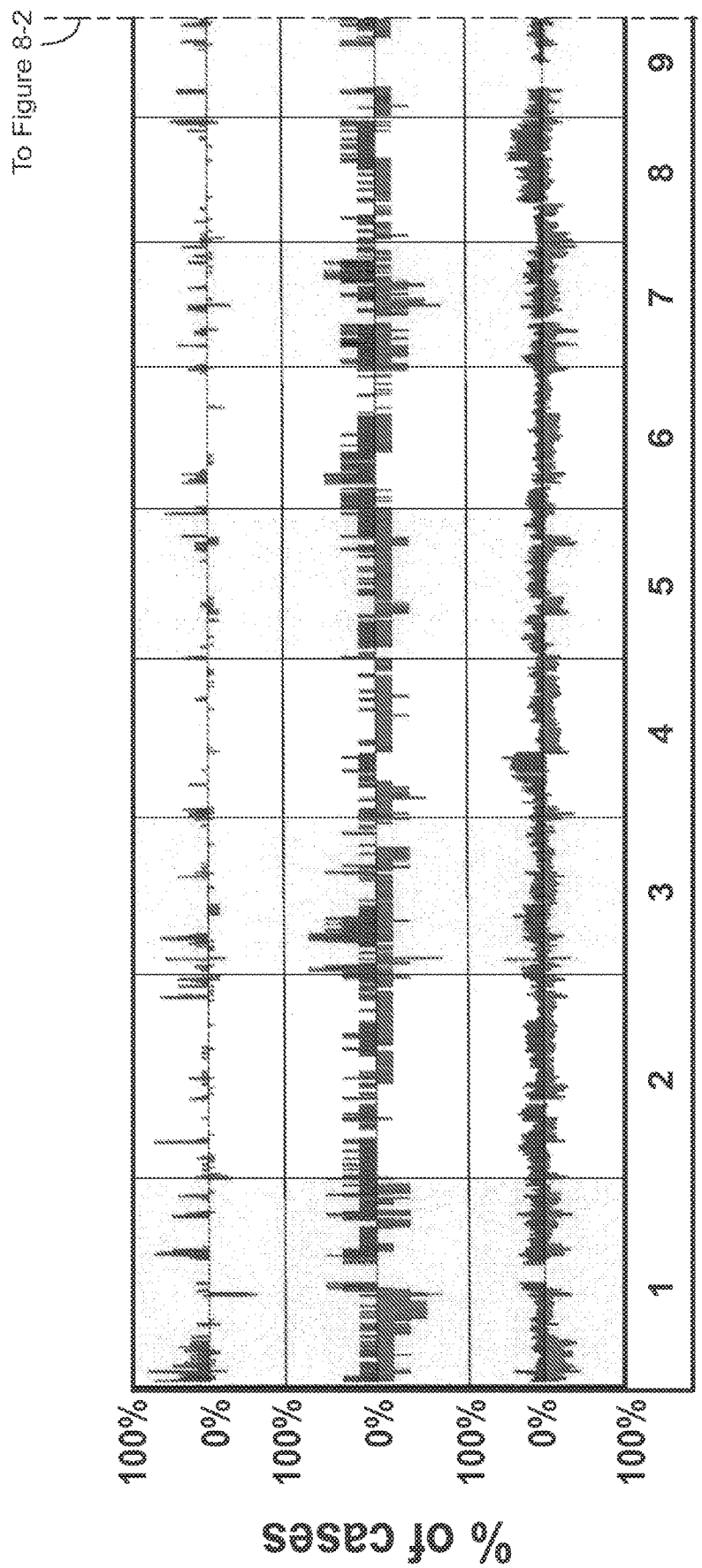
Figures 2, 8:
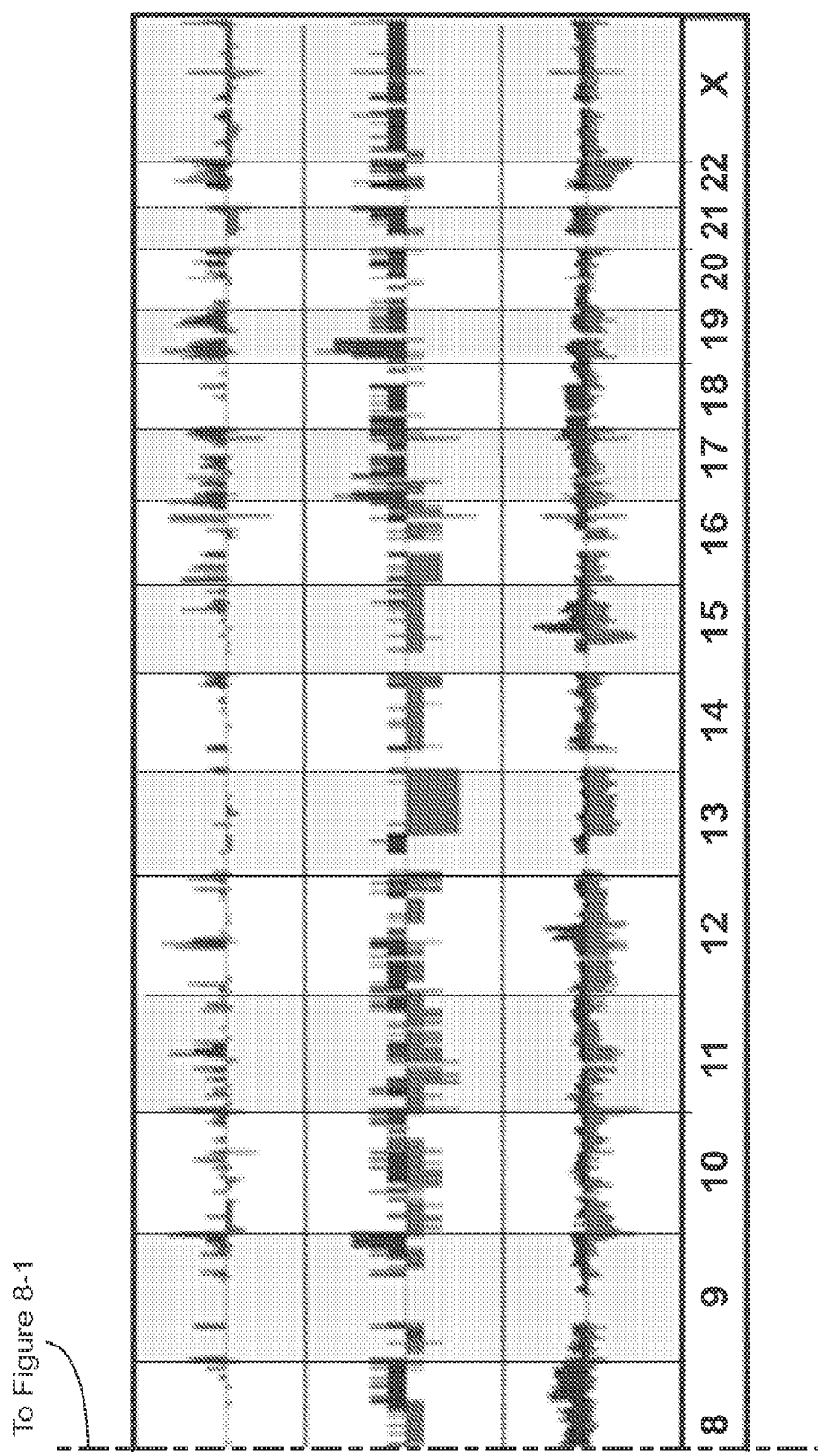

FIG. 8. Canine oral melanoma (OM), cutaneous melanoma (CM), and benign melanocytoma (B) oaCGH profile data recoded as human.

Figures 1, 9:
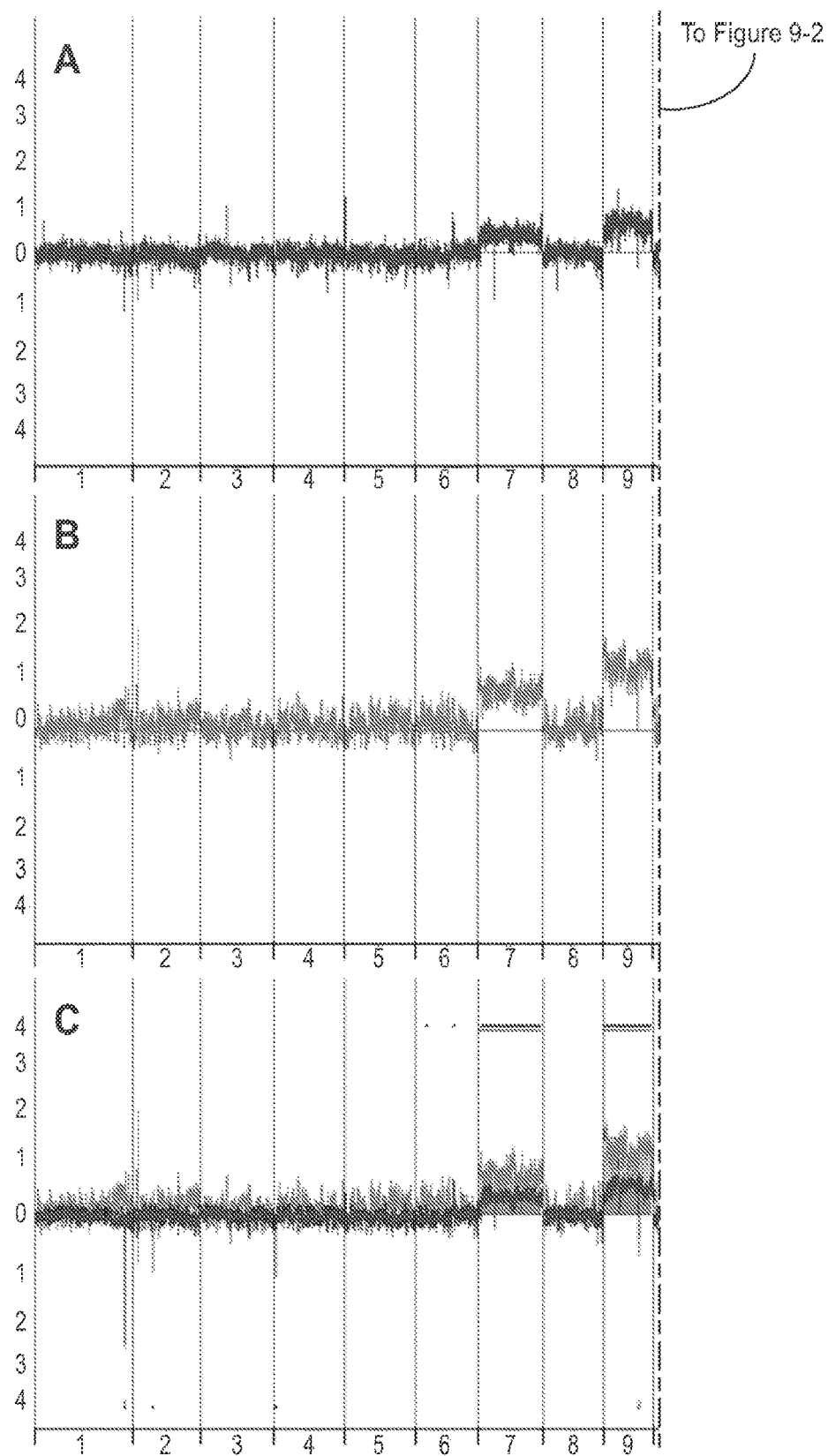
Figures 2, 9:
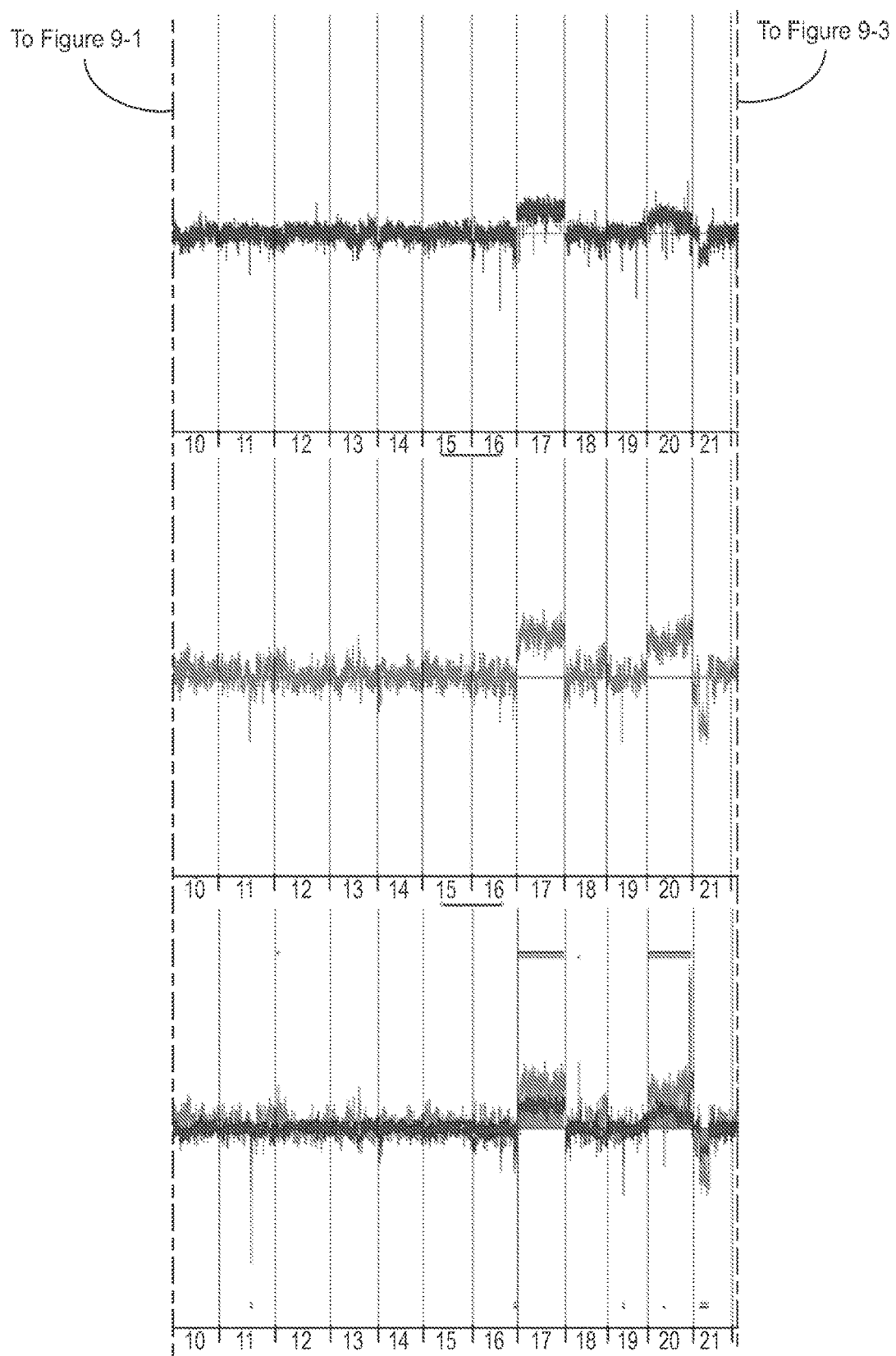
Figures 3, 9:
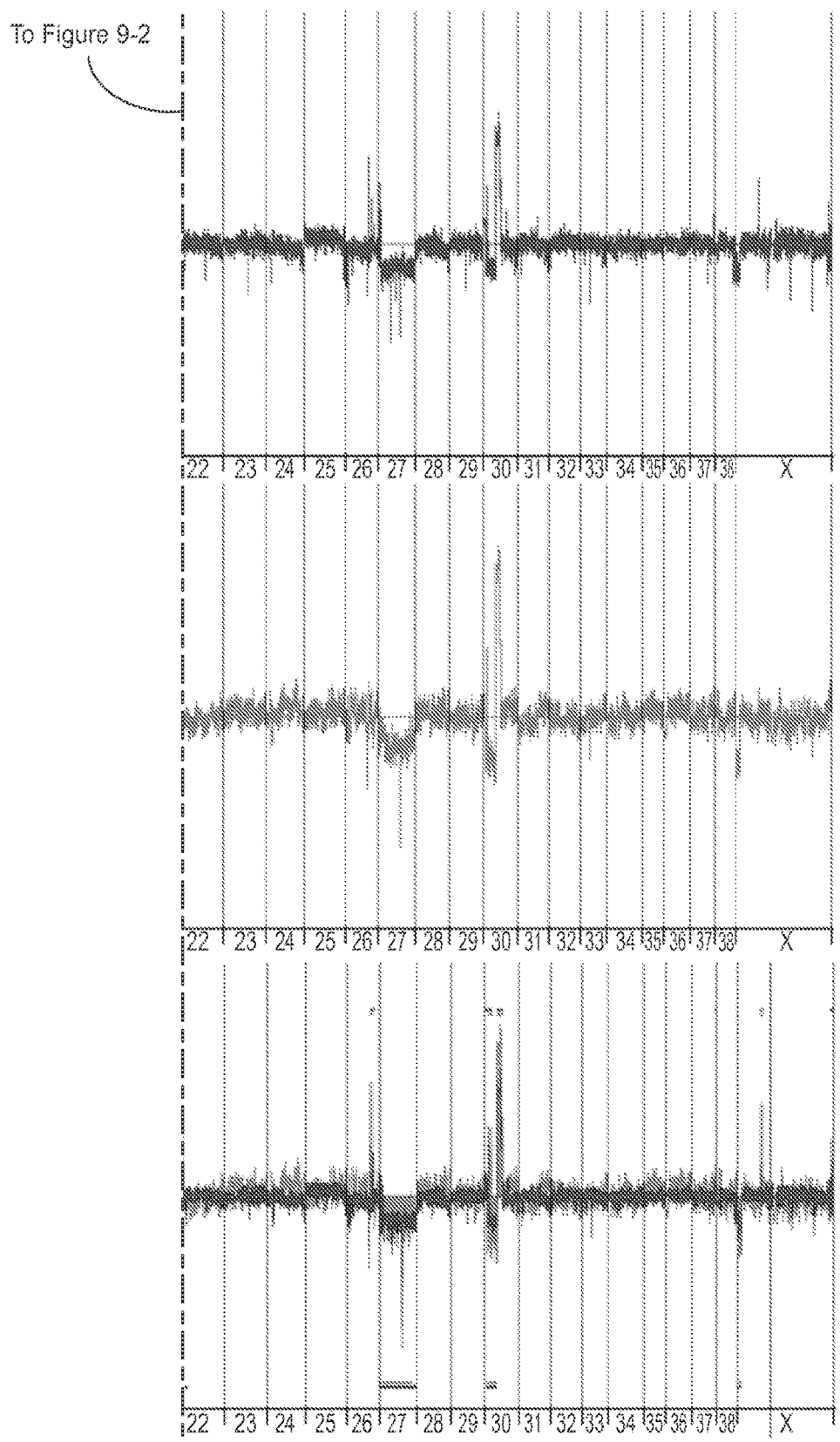

FIG. 9. Comparison of fresh frozen and formalin fixed paraffin embedded tissues from the same tumor biopsy by oaCGH.

5. DETAILED DESCRIPTION OF THE DISCLOSURE

Chromosome 10 Regions

CFA10:5—the region in canfam2 is centered on a peak minimal region that extends from approximately 4,600,000 bases to approximately 5,500,000 bases or Broad CanFam3.1/canfam3 chr10:1617000-2513700 and contains, but is not limited to, for example the following loci (locations in parentheses from canfam3 and Ensembl #); KIFSA (Kinesin heavy chain isoform 5A, chr10:1637146-1663483—(ENSCAFT00000000388) or chr10:1648844-1669273—(ENSCAFT00000046518)0; PIP4K2C (phosphatidylinositol-5-phosphate 4-kinase, type II, gamma; chr10:1669939-1682029—(ENSCAFT00000000391)0; LOC100687947, ARHGEF25 (Rho guanine nucleotide exchange factor (GEF) 25; chr10:1687463-1695313—(ENSCAFT00000000393)); SLC26A10 (solute carrier family 26, member 10; chr10:1688394-1796947—(ENSCAFT00000000396) or chr10:1696659-1701957—(ENSCAFT00000000398); LOC607508, B4GALNT1 (beta-1,4-N-acetyl-galactosaminyl transferase 1; chr10:1704169-1741787—(ENSCAFT00000000401)); OS9 (chr10:1756969-1788786—(ENSCAFT00000000412) or chr10:1757112-1787135—(ENSCAFT00000000411)); AGAP2 (ArfGAP with GTPase domain, ankyrin repeat and PH domain 2; AGAP2 at chr10:1792666-1807610—(ENSCAFT00000047785) or chr10:1792666-1941692—(ENSCAFT00000000434); TSPAN31 (tetraspanin 31; not in UCSC canfam3); CDK4 (cyclin-dependent kinase 4; chr10:1813184-1815126—(ENSCAFT00000000440), LOC481132, LOC481133, METTL1 (methyltransferase like 1; chr10:1831408-1833859—(ENSCAFT00000000448)); LOC100688454, TSFM (Ts translation elongation factor, mitochondrial; NC_006592.3 (1841991 . . . 1854952; AVIL (advillin; chr10:1855579-1872303—(ENSCAFT00000000466)); CTDSP2 (CTD (carboxy-terminal domain, RNA polymerase II, polypeptide A) small phosphatase 2; chr10:1878905-1898297—(ENSCAFT00000000474)); and LOC100685525, LOC100687853, XRCC6BP1 (XRCC6 binding protein 1; chr10:1828395-1994625—(ENSCAFT00000049505) or chr10:1981502-1995052—(ENSCAFT00000000475)) in addition to cfa-mir-26-a2. In some cases of malignant melanoma the extent of the full segment that is subject to copy number increase may extend from the centromere to at least canfam2 19 Mb on CFA 10 or canfam3 chr10:16011600.

CFA10:14—the region in canfam2 is centered on a peak minimal region that extends from approximately 13,871,000 bases to approximately 14,100,000 bases or canfam3 chr10:10887000-11116000 and contains, but is not limited to, for example the following loci; LOC481154, MDM2 (MDM2 oncogene, E3 ubiquitin protein ligase; chr10:10936607-10962527—(NM_001003103); chr10:10936609-10971551—(ENSCAFT00000000663)) and LOC100685525. In some cases of malignant melanoma the extent of the full segment that is subject to copy number increase may extend the full length of canFam2 CFA 10 from at least 10 Mb to at least 19 Mb on CFA 10 or canFam3 chr10:7,000,000-16,000,000.

CFA10:20—the region in canfam2 is centered on a peak minimal region that extends from canfam2 approximately 20,355,000 bases to approximately 20,708,500 bases or canfam3 chr10:17366629-17720225 and extends either side out to, in some cases include the region spanning at least canfam2 15 Mb through 40 Mb or canfam3 chr10:12,000,000-37,000,000 and beyond.

Chromosome 30 Regions

CFA30:9—the region in canfam2 is centered on a peak minimal region that extends from approximately 8,300,000 bases to approximately 9,000,000 bases or canfam3 chr30: 5,300,000-6,000,000, and contains, but is not limited to, for example the following loci; TMCOSA (transmembrane and coiled-coil domains 5A; chr30:5333067-5352759—(ENSCAFT00000045738) or chr30:5333130-5340330—(ENSCAFT00000013688), SPRED1 (sprouty-related, EVH1 domain containing 1; chr30:5594473-5710814—(ENSCAFT00000013709)); LOC478254, and extends either side in some cases to include the region from the CFA30 centromere through to canfam 2 19 Mb or chr30:16,000,000.

CFA30:19—the region in canfam2 is centered on a peak minimal region and extends from approximately 18,500,000 bases to 21,000,000 bases or canfam3 chr30:15,500,000-18,000,000, and contains, but is not limited to, for example the following loci; GALK2 (galactokinase 2; chr30:15371667-15497506—(ENSCAFT00000023652)); LOC100687990, ATP8B4 (ATPase, class I, type 8B, member 4; chr30: 15885969-16103140—(ENSCAFT00000046088) or chr30: 15887677-16049072—(ENSCAFT00000023794);
SLC27A2 (solute carrier family 27 (fatty acid transporter), member 2; chr30:16155158-16197949—(ENSCAFT00000023903)), HDC (histidine decarboxylase; chr30:16201299-16223203—(ENSCAFT00000023936)),
GABPB1 (GA binding protein transcription factor, beta subunit 1; chr30:16238116-16267014—(ENSCAFT00000023990)), USP8 (ubiquitin specific peptidase 8; chr30:16358958-16407557—(ENSCAFT00000024054)), USP50 (ubiquitin specific peptidase 50; chr30:16409376-16453807—(ENSCAFT00000024071)), TRPM7 (transient receptor potential cation channel, subfamily M, member 7; chr30: 16465475-16579868—(ENSCAFT00000024268)),
LOC478301, LOC100688724, AP4E1 (adaptor-related protein complex 4, epsilon 1 subunit; chr30:16734253-16800722—(ENSCAFT00000024322)), TNFAIP8L3 (tumor necrosis factor, alpha-induced protein 8-like 3; chr30: 16822972-16823538—(ENSCAFT00000024328)),
CYP19A1 (cytochrome P450, family 19, subfamily A, polypeptide 1; chr30:16957224-16988347—(NM_001008715); chr30:16957215-16988392—(ENSCAFT00000024355)),
GLDN (gliomedin; chr30:17082385-17141845—(ENSCAFT00000043803) or chr30:17082398-17141845—(ENSCAFT00000024375)), DMXL2 (Dmx-like 2; chr30: 17157285-17308602—(ENSCAFT00000024538) or chr30: 17157285-17276277—(ENSCAFT00000024526)), SCG3 (secretogranin III; chr30:17374100-17406166—(ENSCAFT00000024572)), LYSMD2 (LysM, putative peptidoglycan-binding, domain containing 2; chr30:17409843-17424235—(ENSCAFT00000024586)), TMOD1 (tropomodulin 1; chr11:54853205-54912709—(ENSCAFT00000003834)), TMOD3 (tropomodulin 3 (ubiquitous); chr30:17543229-17595323—(ENSCAFT00000024709), LEO1 (Leo1, Paf1/RNA polymerase II complex component, homolog (*S. cerevisiae*); chr30: 17609902-17651295—(ENSCAFT00000043288) or chr30: 17614631-17650877—(ENSCAFT00000024767)),
MAPK6 (mitogen-activated protein kinase 6; chr30: 17721690-17768478—(ENSCAFT00000024780) or chr30: 17721690-17736072—(ENSCAFT00000037788),
LOC100685546, GNB5 (guanine nucleotide binding protein (G protein), beta 5; chr30:17832358-17876491—(ENSCAFT00000046605) or chr30:17838577-17881018—(ENSCAFT00000024816)), MYOSC (myosin VC; chr30: 17887781-17972687—(ENSCAFT00000050187) or chr30: 17889709-17972510—(ENSCAFT00000024852),
MYO5A (myosin VA (heavy chain 12, myoxin); chr30: 17996562-18116623—(ENSCAFT00000025057) or chr30: 17996562-18116499—(ENSCAFT00000048838). In some cases the regions extends from approximately canfam2 12,500,000 bp (canfam3 chr30:9,500,000) through to the CFA 30 telomere.

Method of Detection:

The copy number status of the regions assessed may be measured by, but is not limited to, fluorescence in situ hybridization (FISH), polymerase chain reaction (PCR), comparative genomic hybridization (CGH), or next generation sequencing (NGS). The biological sample must be a biopsy of the mass and may be a fresh sample, a fresh-frozen sample of the suspected mass, a sample in a preservative such as, for example, RNAlater, or a sample that has been processed for pathologic assessment. For example the tissue specimen may have been soaked in one of several options to fix the tissues for histologic evaluation, such as, but not limited to, conventional histologic fixatives including, 10% neutral buffered formalin, B5, zinc-formalin. The sample may also have been soaked in formalin free fixatives such as, but not limited to, for example, 70% ethanol FineFIX, RCL-2 and HOPE.

The invention also provides a method of selecting treatment for a dog with melanoma. The detection and quantification of the copy number status at regions of CFA 10 and CFA 30 would indicate the presence of a malignant melanoma and thus may be used to direct therapy accordingly. If the dog has melanoma, the therapy may be, for example, surgical resection of the mass with wide margins, the extent of which is determined by the size and precise location of the mass, surgical resection followed by radiation therapy and/or melanoma vaccine and/or treatment with one or more chemotherapeutic agents.

In addition, the invention provides a kit for detecting a malignant melanoma in a dog comprising:
(a) reagents selected from the group consisting of: a nucleic acid probe capable of specifically detecting the regions of CFA 10 and CFA 30,
(b) instructions for use in measuring a copy number of CFA 10 and/or CFA 30 in a biological sample from a dog wherein if the copy number of CFA 10 and/or CFA 30 presents with alternating regions of DNA copy number gain then loss (for CFA 10), and/or loss then gain (for CFA 30) compared to that using a specimen from a normal control.

5.1. Definitions

The While the following terms are believed to be well understood by one of ordinary skill in the art, the following definitions are set forth to facilitate explanation of the presently disclosed subject matter.

"Malignant oral melanoma" refers to malignant neoplasms of melanocytes, which are pigment cells present normally in the epidermis. Melanocytes are located most densely amongst the basal layers of the epidermis but can be found throughout the body in both epidermal and mucosal tissue layers, including the oral cavity. The invention is particularly well suited for those neoplasms that form in the mucosa of the oral cavity of a dog and neighboring tissues.

"Copy number" is a measurement of DNA, whether of a single locus, one or more loci, or an entire genome. A "copy number" of two is "wild-type" in a dog (because of diploidy, except for sex chromosomes). A "copy number" of other than two in a dog (except for sex chromosomes) deviates from wild-type. Such deviations include gains, i.e., increases in copy number generally up to 5 copies per cell, deletions, i.e., decreases in copy number i.e either 1 or 0 copies per cell, and amplifications, i.e., increases in copy number generally in excess of 5 copies per cell.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling.

The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

"Probe," in the context of the present disclosure, is an oligonucleotide or polynucleotide that can selectively hybridize to at least a portion of a target sequence under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications such as PCR, whereas a length of about 50 to about $1 \times 10^6$ nucleotides can be preferred for chromosomal probes and a length of about 5,000 to about 800,000 nucleotides or more preferably about 75,000 to about 200,000 for BAC probes.

The invention encompasses fragments of nucleic acids that can serve (1) as probes for detecting segments of domestic dog (*Canis familairis*, CFA) genome referred to as chromosomes 10 or 30 (hereafter referred to as CFA 10 and CFA 30). The dog genome has been sequenced and is available for example, USCS canfam2 at http://genome.ucsc.edu/cgi-bin/hgGateway?db=canFam2 and the NCBI *Canis lupus familiaris* genome database; or ENSEMBL database CanFam3.1 (GCA_000002285.2). See also, Lindblad-Toh et al. 2005 "Genome sequence, comparative analysis and haplotype structure of the domestic dog" *Nature* 438 (7069), 803-819.

The changes in copy number of regions of CFA 10 and/or CFA 30 may be detected by a number of methods well known in the art, e.g., Southern and northern blotting, dot blotting, colony hybridizations, hybridization to an array, comparative genomic hybridization (CGH), etc. or (2) as polymerase chain reaction (PCR) primers to amplify CFA 10 and/or 30. PCR primers can comprise, in addition to CFA 10 and/or 30 nucleic acid sequences, other sequences such as restriction enzyme cleavage sites that facilitate the use of the amplified nucleic acid. PCR is described in the following references: Saiki et al. 1988 *Science* 239 487-491; *PCR Technology*, Erlich, ed., Stockton Press, (1989). As explained below, PCR can be useful to detect abnormally low or high levels of target regions of chromosomes including CFA 10 and 30.

Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, (1989)) and *Current Protocols in Molecular Biology* (F. M. Ausubel et al., eds., John Wiley & Sons, Inc., sections 2.10 and 6.3-6.4 (1995)), the relevant portions of which are incorporated by reference herein. Moderately stringent conditions for filter hybridizations include hybridization in about 50% formamide, 6×SSC at a temperature from about 42 C to 55 C and washing at about 60 C in 0.5×SSC, 0.1% SDS. Highly stringent conditions are defined as hybridization conditions as above, but with washing at approximately 68 C in 0.2×SSC, 0.1% SDS. SSPE (1×SSPE is 0.15 M NaCl, 10 mM $NaH_2PO_4$, and 1.26 mM EDTA, pH 7.4) can be substituted for SSC (1×SSC is 0.15 M NaCl and 15 mM sodium citrate) in the hybridization and wash buffers; washes, optionally at least two washes, are performed for 15 minutes after hybridization is complete.

It should be understood that the wash temperature and wash salt concentration can be adjusted as necessary to achieve a desired degree of stringency by applying the basic principles that govern hybridization reactions and duplex stability, as known to those skilled in the art and described further below (see e.g., Sambrook et al., supra). When nucleic acids of known sequence are hybridized, the hybrid length can be determined by aligning the sequences of the nucleic acids (for example, using GAP) and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (degrees C.)=2(# of A+T bases)+4(# of G+C bases). For hybrids above 18 base pairs in length, Tm (degrees C.)=81.5+16.6 ($\log_{10}$[Na+])+0.41 (% G+C)−(600 N), where N is the number of bases in the hybrid, and [Na+] is the concentration of sodium ions in the hybridization buffer. Each such hybridizing nucleic acid has a length that is at least 15 nucleotides (or at least 18 nucleotides, or at least 20, or at least 25, or at least 30, or at least 40, or at least 50, or at least 100. Sambrook et al., supra.

5.2. Polynucleotide Amplification and Determination

In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits of the invention may use any nucleic acid amplification or detection methods known to one skilled in the art, such as those described in U.S. Pat. No. 5,525,462 (Takarada et al.); U.S. Pat. No. 6,114,117 (Hepp et al.); U.S. Pat. No. 6,127,120 (Graham et al.); U.S. Pat. No. 6,344,317 (Urnovitz); U.S. Pat. No. 6,448,001 (Oku); U.S. Pat. No. 6,528,632 (Catanzariti et al.); and PCT Pub. No. WO 2005/111209 (Nakajima et al.); all of which are incorporated herein by reference in their entirety.

Commonly used methods known in the art for the quantification of mRNA expression in a sample include northern blotting and in situ hybridization (Parker and Barnes, *Methods Mol. Biol.* 106:247-83, 1999), RNAse protection assays (Hod, *Biotechniques* 13:852-54, 1992), PCR-based methods, such as reverse transcription PCR(RT-PCR) (Weis et al., *TIG* 8:263-64, 1992), and array-based methods (Schena et al., *Science* 270:467-70, 1995). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE), bead-based technologies, single molecule fluorescence in situ hybridization (smFISH) studies, and gene expression analysis by massively parallel signature sequencing. Velculescu et al. 1995 *Science* 270 484-487; Streefkerk et al., 1976, *Pro Biol Fluid Proc Coll* 24 811-814; Soini U.S. Pat. No. 5,028,545; smFISH, Lyubimova et al. 2013 *Nat Protocol* 8(9) 1743-1758.

In some embodiments, the nucleic acids are amplified by PCR amplification using methodologies known to one skilled in the art. One skilled in the art will recognize, however, that amplification can be accomplished by any known method, such as ligase chain reaction (LCR), Qβ-replicase amplification, rolling circle amplification, transcription amplification, self-sustained sequence replication, nucleic acid sequence-based amplification (NASBA), each of which provides sufficient amplification. Branched-DNA technology may also be used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, *Adv. Clin. Chem.* 33:201-235).

The PCR process is well known in the art and is thus not described in detail herein. For a review of PCR methods and protocols, see, e.g., Innis et al., eds., *PCR Protocols, A Guide to Methods and Application*, Academic Press, Inc., San Diego, Calif. 1990; U.S. Pat. No. 4,683,202 (Mullis); which are incorporated herein by reference in their entirety. PCR reagents and protocols are also available from commercial vendors, such as Roche Molecular Systems (Pleasanton, Calif.). PCR may be carried out as an automated process with a thermostable enzyme. In this process, the temperature of the reaction mixture is cycled through a denaturing region, a primer annealing region, and an extension reaction region automatically. Machines specifically adapted for this purpose are commercially available.

5.3. High Throughput, Single Molecule Sequencing, and Direct Detection Technologies Suitable next generation sequencing technologies are widely available. Examples include the 454 Life Sciences platform (Roche, Branford, Conn.) (Margulies et al. 2005 *Nature*, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., 2006, *Genome Res.* 16, 383-393; U.S. Pat. Nos. 6,306,597 and 7,598,035 (Macevicz); U.S. Pat. No. 7,232,656 (Balasubramanian et al.)); or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453 (Barany et al.); or the Helicos True Single Molecule DNA sequencing technology (Harris et al., 2008 *Science*, 320, 106-109; U.S. Pat. Nos. 7,037,687 and 7,645,596 (Williams et al.); U.S. Pat. No. 7,169,560 (Lapidus et al.); U.S. Pat. No. 7,769,400 (Harris)), the single molecule, real-time (SMRT™) technology of Pacific Biosciences, and sequencing (Soni and Meller, 2007, *Clin. Chem.* 53, 1996-2001) which are incorporated herein by reference in their entirety. These systems allow the sequencing of many nucleic acid molecules isolated from a specimen at high orders of multiplexing in a parallel fashion (Dear, 2003, *Brief Funct. Genomic Proteomic*, 1(4), 397-416 and McCaughan and Dear, 2010, *J. Pathol.*, 220, 297-306). Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, *Nat. Prot.* 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., 2003, *J. Biotech.* 102, 117-124). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing or detection, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each other for energy transfer to occur successfully. Bailey et al. recently reported a highly sensitive (15 pg methylated DNA) method using quantum dots to detect methylation status using fluorescence resonance energy transfer (MS-qFRET) (Bailey et al. 2009, *Genome Res.* 19(8), 1455-1461, which is incorporated herein by reference in its entirety).

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., Braslaysky et al., PNAS 100(7): 3960-3964 (2003); U.S. Pat. No. 7,297,518 (Quake et al.) which are incorporated herein by reference in their entirety). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer-released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

The technology may be practiced with digital PCR. Digital PCR was developed by Kalinina and colleagues (Kalinina et al., 1997, *Nucleic Acids Res.* 25; 1999-2004) and further developed by Vogelstein and Kinzler (1999, *Proc. Natl. Acad. Sci. U.S.A.* 96; 9236-9241). The application of digital PCR is described by Cantor et al. (PCT Pub. Nos. WO 2005/023091A2 (Cantor et al.); WO 2007/092473 A2, (Quake et al.)), which are hereby incorporated by reference in their entirety. Digital PCR takes advantage of nucleic acid (DNA, cDNA or RNA) amplification on a single molecule level, and offers a highly sensitive method for quantifying low copy number nucleic acid. Fluidigm® Corporation, BioRad's Digital PCR and Raindance technologies all offer systems for the digital analysis of nucleic acids. See, Karlin-Neumann G et al. (2012). Probing copy number variations using Bio-Rads QX100™ Droplet Digital™ PCR system. Bio-Rad Bulletin 6277; Diderot et al., *Clinical Chemistry* February 2013 clinchem. 2012.193409.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in PCT Pub. No. WO 2009/091934 (Cantor).

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected.

A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

Next generation sequencing techniques may be applied to measure expression levels or count numbers of transcripts using RNA-seq or whole transcriptome shotgun sequencing. See, e.g., Mortazavi et al. 2008 *Nat Meth* 5(7) 621-627 or Wang et al. 2009 *Nat Rev Genet* 10(1) 57-63.

Nucleic acids in the invention may be counted using methods known in the art. In one embodiment, NanoString's n Counter system may be used. Geiss et al. 2008 *Nat Biotech* 26(3) 317-325; U.S. Pat. No. 7,473,767 (Dimitrov). Alternatively, Fluidigm's Dynamic Array system may be used. Byrne et al. 2009 *PLoS ONE* 4 e7118; Helzer et al. 2009 *Can Res* 69 7860-7866. For reviews, see also Zhao et al. 2011 *Sci China Chem* 54(8) 1185-1201 and Ozsolak and Milos 2011 *Nat Rev Genet* 12 87-98.

The invention encompasses any method known in the art for enhancing the sensitivity of the detectable signal in such assays, including, but not limited to, the use of cyclic probe technology (Bakkaoui et al., 1996, *BioTechniques* 20: 240-8, which is incorporated herein by reference in its entirety); and the use of branched probes (Urdea et al., 1993, *Clin. Chem.* 39, 725-6; which is incorporated herein by reference in its entirety). The hybridization complexes are detected according to well-known techniques in the art.

Reverse transcribed or amplified nucleic acids may be modified nucleic acids. Modified nucleic acids can include nucleotide analogs, and in certain embodiments include a detectable label and/or a capture agent. Examples of detectable labels include, without limitation, fluorophores, radioisotopes, colorimetric agents, light emitting agents, chemiluminescent agents, light scattering agents, enzymes and the like. Examples of capture agents include, without limitation, an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments.

The invention described herein may be used in conjunction with other molecular techniques for detection of cancer such as US Pat Pub 2013/0171637 (Giafis et al.) the contents of which are hereby incorporated by reference in its entirety.

5.4. Statistical Methods

The data may be ranked for its ability to distinguish biomarkers in both the 1 versus all (i.e., disease versus normal) and the all-pairwise (i.e., normal versus specific disease) cases. One statistic used for the ranking is the area under the receiver operator characteristic (ROC) curve (a plot of sensitivity versus (1-specificity)). Although biomarkers are evaluated for reliability across datasets, the independent sample sets are not combined for the purposes of the ROC ranking. As a result, multiple independent analyses are performed and multiple independent rankings are obtained for each biomarker's ability to distinguish groups of interest.

It is to be understood that other genes and/or diagnostic criteria may be used in this invention. For example, animal characteristics, standard blood workups, the results of imaging tests, and/or histological evaluation may optionally be combined with biomarkers disclosed herein.

Such analysis methods may be used to form a predictive model, and then use that model to classify test data. For example, one convenient and particularly effective method of classification employs multivariate statistical analysis modeling, first to form a model (a "predictive mathematical model") using data ("modeling data") from samples of known class (e.g., from subjects known to have, or not have, a particular class, subclass or grade of lung cancer), and second to classify an unknown sample (e.g., "test data"), according to lung cancer status.

Pattern recognition (PR) methods have been used widely to characterize many different types of problems ranging for example over linguistics, fingerprinting, chemistry and psychology. In the context of the methods described herein, pattern recognition is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots that can be interpreted by the human eye. The other approach is termed "supervised" whereby a training set of samples with known class or outcome is used to produce a mathematical model and is then evaluated with independent validation data sets.

Unsupervised PR methods are used to analyze data without reference to any other independent knowledge. Examples of unsupervised pattern recognition methods include principal component analysis (PCA), hierarchical cluster analysis (HCA), and non-linear mapping (NLM).

Alternatively, and in order to develop automatic classification methods, it has proved efficient to use a "supervised" approach to data analysis. Here, a "training set" of biomarker expression data is used to construct a statistical model that predicts correctly the "class" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each class, for example, each class of lung cancer in terms of its biomarker expression profile. It is also possible to obtain confidence limits on any predictions, for example, a level of probability to be placed on the goodness of fit (see, for example, Sharaf; Illman; Kowalski, eds. (1986). Chemometrics. New York: Wiley). The robustness of the predictive models can also be checked using cross-validation, by leaving out selected samples from the analysis.

Examples of supervised pattern recognition methods include the following nearest centroid methods (Dabney 2005 *Bioinformatics* 21(22):4148-4154 and Tibshirani et al. 2002 *Proc. Natl. Acad. Sci. USA* 99(10):6576-6572); soft independent modeling of class analysis (SIMCA) (see, for example, Wold, (1977) Chemometrics: theory and application 52: 243-282.); partial least squares analysis (PLS) (see, for example, Wold (1966) Multivariate analysis 1: 391-420; Joreskog (1982) Causality, structure, prediction 1: 263-270); linear discriminant analysis (LDA) (see, for example, Nillson (1965). Learning machines. New York.); K-nearest neighbor analysis (KNN) (see, for example, Brown and Martin 1996 *J Chem Info Computer Sci* 36(3):572-584); artificial neural networks (ANN) (see, for example, Wasserman (1993). Advanced methods in neural computing. John Wiley & Sons, Inc; O'Hare & Jennings (Eds.). (1996). Foundations of distributed artificial intelligence (Vol. 9). Wiley); probabilistic neural networks (PNNs) (see, for example, Bishop & Nasrabadi (2006). Pattern recognition and machine learning (Vol. 1, p. 740). New York: Springer; Specht, (1990). Probabilistic neural networks. Neural networks, 3(1), 109-118); rule induction (RI) (see, for example, Quinlan (1986) Machine learning, 1(1), 81-106); and, Bayesian methods (see, for example, Bretthorst (1990). An introduction to parameter estimation using Bayesian probability theory. In Maximum entropy and Bayesian methods (pp. 53-79). Springer Netherlands; Bretthorst, G. L. (1988). Bayesian spectrum analysis and parameter estimation (Vol. 48). New York: Springer-Verlag); unsupervised hierarchical clustering (see for example Herrero 2001 Bioinformatics 17(2) 126-136). In one embodiment, the classifier is the centroid based method described in Mullins et al. 2007 Clin Chem 53(7):1273-9, which is herein incorporated by reference in its entirety for its teachings regarding disease classification.

It is often useful to pre-process data, for example, by addressing missing data, translation, scaling, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may be replaced or "filled" with, for example, the mean value of a column ("mean fill"); a random value ("random fill"); or a value based on a principal component analysis ("principal component fill"). Each of these different approaches will have a different effect on subsequent PR analysis.

"Translation" of the descriptor coordinate axes can be useful. Examples of such translation include normalization and mean centering. "Normalization" may be used to remove sample-to-sample variation. Many normalization approaches are possible, and they can often be applied at any of several points in the analysis. "Mean centering" may be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt (StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centred and unit variance scaled. This technique is a very useful because each descriptor is then weighted equally and large and small values are treated with equal emphasis. This can be important for analytes present at very low, but still detectable, levels.

Several supervised methods of scaling data are also known. Some of these can provide a measure of the ability of a parameter (e.g., a descriptor) to discriminate between classes, and can be used to improve classification by stretching a separation. For example, in "variance weighting," the variance weight of a single parameter (e.g., a descriptor) is calculated as the ratio of the inter-class variances to the sum of the intra-class variances. A large value means that this variable is discriminating between the classes. For example, if the samples are known to fall into two classes (e.g., a training set), it is possible to examine the mean and variance of each descriptor. If a descriptor has very different mean values and a small variance, then it will be good at separating the classes. "Feature weighting" is a more general description of variance weighting, where not only the mean and standard deviation of each descriptor is calculated, but other well-known weighting factors, such as the Fisher weight, are used.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The process of comparing a measured value and a reference value can be carried out in any convenient manner appropriate to the type of measured value and reference value for the discriminative gene at issue. "Measuring" can be performed using quantitative or qualitative measurement techniques, and the mode of comparing a measured value and a reference value can vary depending on the measurement technology employed. For example, when a qualitative colorimetric assay is used to measure expression levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values. In other examples, measured values are qualitative. As with qualitative measurements, the comparison can be made by inspecting the numerical data, or by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker protein. Alternately, a separate device (e.g., a digital computer) may be used to compare the measured value(s) and the reference value(s). Automated devices for comparison may include stored reference values for the biomarker protein(s) being measured, or they may compare the measured value(s) with reference values that are derived from contemporaneously measured reference samples (e.g., samples from control subjects).

As will be apparent to those of skill in the art, when replicate measurements are taken, the measured value that is compared with the reference value is a value that takes into account the replicate measurements. The replicate measurements may be taken into account by using either the mean or median of the measured values as the "measured value."

The invention also includes methods of identifying animals for particular treatments or selecting animals for which a particular treatment would be desirable or contraindicated.

The methods above may be performed by a reference laboratory, a veterinary hospital pathology laboratory, a university veterinary laboratory, a veterinarian's office or a veterinarian. The methods above may further comprise an algorithm and/or statistical analysis.

5.5. Samples

The sample may be a biopsy specimen of the suspected mass. For detection of the copy number status by FISH, cells from the mass are used to provide templates for the FISH probes. For PCR and DNA sequence based assays, the required template DNA may be obtained from the cells of the suspected mass.

5.6. Compositions and Kits

The invention provides compositions and kits for detecting a malignant melanoma in a dog comprising: (a) at least one reagent selected from the group consisting of: a nucleic acid probe capable of specifically detecting target regions of CFA 10 and/or CFA 30; and (b) instructions for use in measuring a copy number of these region of CFA 10 or CFA 30 in a biological sample from a dog wherein if the copy number status of the regions of CFA 10 and CFA 30 differ from that of a normal control.

The instructions comprise determining in a sample of relevant cells obtained from the dog the presence of chromosomal abnormalities, wherein the presence of chromosomal abnormalities involving at least two of the probes indicates that the patient has malignant melanoma. Such kits may further comprise, or consist of, blocking agents or other probes, various labels or labeling agents to facilitate detection of the probes, reagents for hybridization (e.g., buffers), a metaphase spread, and the like.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The article "a" and "an" are used herein to refer to one or more than one (i.e., to at least one) of the grammatical object(s) of the article. By way of example, "an element" means one or more elements.

As used herein, the verb "comprise" as is used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

6.1. Example 1

Cohort:

A cohort of 78 canine cases, presenting as tumor biopsy specimens, was used to obtained genome wide DNA copy number profiles. The cohort comprised 39 cases of histologically confirmed canine malignant oral melanoma, 18 benign melanocytic lesions and 21 oral lesions confirmed as non-melanotic.

Data Acquisition:

DNA was extracted from all tissue biopsies quality controlled using agarose gel electrophoresis and spectrophotometry. DNA isolated from each case in the cohort (test samples) was labeled using the SureTag DNA Labeling Kit (Agilent) to incorporate a fluorophore-conjugated dNTP, as described previously (Thomas et al. 2011). Gender specific reference DNA samples were generated from mixed breed dogs, pooling equimolar quantities of DNA from 10 healthy males and 10 healthy females and labeled similarly but with a different fluorophore-conjugate dNTP. Fluorescently labeled test and reference samples were hybridized to Canine G3 Sureprint 180,000 feature oligonucleotide-array-cCGH (oaCGH) arrays (Agilent, AMADID 025522) for 40 hours at 65° C. and 20 rpm, as described previously (Thomas et al. 2011).

Aberration Calling:

The FASST2 Segmentation Algorithm (a Hidden Markov Model (HMM) based approach), was used to determine copy number calls. Unlike other common HMM methods for copy number estimation, FASST2 does not aim to estimate the copy number state at each probe but uses many states to cover more possibilities, such as mosaic events. These state values are then used to make calls based on a log-ratio threshold. The significance threshold for segmentation was set at $5 \times 10^{-6}$ also requiring a minimum of three probes per segment and a maximum probe spacing of 1,000 bp between adjacent probes before breaking a segment. The log ratio thresholds for single copy gain and single copy loss were set at +0.201 and −0.231, respectively.

Results:

Genome wide DNA copy number profiling data indicated that canine oral melanoma presents with a wide range of DNA copy number aberrations that may be used to aid diagnosis. In particular, dog chromosomes 10 (CFA 10) and 30 (CFA 30) present with a characteristic sigmoidal profile of DNA copy number change (FIG. 1). Data for the individual cases in the cohort were divided into the three groups 'malignant melanoma", (n=39), 'benign melanoma' (n=18) and 'non-melanoma oral lesions' (n=21). These data are presented in FIGS. 2 and 3 and indicate that the alternating directional changes of copy number status involving chromosomes 10 and 30 are restricted to just the malignant melanomas.

FIG. 1.

Whole chromosome penetrance plots of dog chromosome (CFA) 10 and 30 showing distribution of copy number losses (profiles to left) and gains (profiles to right) in DNA samples prepared from tissue biopsy specimens of confirmed cases (n=39) of canine malignant oral melanomas. Chromosome 10 has two regions of recurrent DNA copy gain, centered at 5 Mb and 14 Mb (circled on the left) and then a recurrent region of DNA copy loss, centered at 20 Mb (circled on the right). Chromosome 30 has a recurrent region of DNA copy number loss, centered at 9 Mb (circled on the right) and then a region of DNA copy number gain, centered at 19 Mb (circled on the left). All genome coordinates are based on values reported in canfam2 version of the canine assembly as of April 2014.

FIG. 2.

DNA copy number status of dog chromosome 10 spanning the region denoted in canfam2 as 4 Mb-25 Mb. The upper part of the figure shows the ideogram of the full length of CFA 10. Below this, each horizontal line indicates the copy number status along the length of the region for an individual case in the expanded region of ~4 to ~25 Mb of CFA 10. The Dark gray/light gray horizontal bars across the regions indicate the extent of any DNA copy number loss/gain in each case. Lack of a tinted bar indicates a balanced copy number. These data indicate that combinations of three regions of recurrent DNA copy change on CFA 10, centered at 5 Mb, 14 Mb and 20 Mb (arrowed), were evident in malignant oral melanoma (n=39, bottom profiles), and absent in cases of benign melanoma (n=18, middle profiles) and non-melanoma oral lesions (n=21, top profiles). The non-melanoma oral lesions did present with recurrence of a DNA copy loss of chromosome 10 at the region centered on 20 Mb, and the non-melanoma oral lesion had either DNA copy number gain or loss at the same region on CFA 20. However, neither of these two groups had a simultaneous DNA copy gain of either the region centered at 5 Mb or at 14 Mb.

FIG. 3.

DNA copy number status of dog chromosome 30 spanning the region denoted in canfam2 as 5 Mb to almost 30 Mb. The upper part of the figure shows the ideogram of full length of CFA 30. Below this, each horizontal line indicates the copy number status along the length of the region for an individual case in the expanded region of ~5 to ~30 Mb of CFA 30. Dark gray/light gray horizontal bars across the regions indicate the extent of any DNA copy number loss/gain in each case. Lack of a tinted bar indicates a balanced copy number. These data indicate that combinations of two regions of recurrent DNA copy change, centered at 9 Mb and 19 Mb (arrowed) are evident as DNA copy number loss and gain, respectively, in malignant oral melanoma (n=39, bottom profiles), and that neither aberration was co-detected in cases of benign melanoma (n=18, middle profiles) and non-melanoma oral lesions (n=21, top profile).

Gene Content of the Regions Restricted to Aberrations in Malignant Melanoma:

Each region identified above was evaluated for the presence of coding regions as indicated by the canfam2 build of the canine genome assembly (see http://genome.ucsc.edu/cgi-bin/hgGateway?db=canFam2). Detection and quantification of any of the genes/coding sequence/regulatory elements listed below, or any additional such genes/coding sequence/regulatory elements that are added subsequently to the annotated canine genome assembly, may be used as the basis to provide an indication that the canine neoplasm from which the cells were derived is a malignant melanoma.

6.2. Example 2 Materials and Methods

Canine oral melanomas and benign melanocytomas were obtained as biopsy specimens from patients as part of their routine diagnostic procedure, with informed owner consent. All cases were diagnosed by pathology evaluation of formalin fixed paraffin embedded (FFPE) specimens and any histologic evaluation was recorded from initial diagnosis report. Where the diagnostic Hematoxylin and Eosin (H&E) slide was made available (56/67 cases) the initial diagnosis was independently confirmed by three board certified veterinary pathologists (SM, PL and LB) and evaluated for percent pigmentation, mitotic index, presence of junctional activity, and tissue morphology as previously described (Smedley et al., 2011). Differences in histologic characteristics between melanomas and benign melanocytomas were analyzed for statistical significance with a one-tailed Mann-Whitney U Test.

The cohort for DNA isolation comprised specimens from 67 individuals, 53 were available to the study only as the fixed tissue specimen, 11 were available only as a snap frozen tumor punch biopsies, and three were available as both FFPE and snap frozen tumor tissue. The cases used for DNA isolation were as follows; 44 biopsies of primary oral melanomas (FFPE (n=32) or fresh frozen (n=12)), five biopsies of cutaneous melanomas (FFPE (n=3) and fresh frozen (n=2)) and 18 biopsies of primary cutaneous melanocytoma (all FFPE). All unfixed tumor specimens (punch biopsies) were snap frozen in liquid nitrogen at the time of removal and subsequently stored at −80° C. A direct comparison of copy number profiles from fresh tissue and the corresponding tumor enriched FFPE sample showed no difference in called aberrations indicating that punch biopsies were not substantially infiltrated with non-neoplastic cells (FIG. 9). As such the study used a combination of snap frozen punch biopsies and FFPE derived specimens as the source of tumor DNA. A detailed description of the specimens used in the study are provided in Table 2.

Genomic DNA Extraction

Genomic DNA was extracted from tumor punch biopsies using the Qiagen DNeasey Kit according to the manufacturer's recommendations (Qiagen, Germantown, Md., USA) and assessed for quality and quantity by spectrophotometry. Genomic DNA integrity, assessed by agarose gel electrophoresis, indicated little to no degradation.

Within the cohort of FFPE samples, several contained margins with bordering non-neoplastic tissues that would 'contaminate' the DNA of the tumor cell population. Areas of tissue enriched for tumor and areas of non-neoplastic margin were thus identified and indicated on a representative H&E-stained 5 µm slide independently by two veterinary pathologists (PL and LB). Three adjacent 25 µm sections were then obtained from each FFPE specimen and the normal/margin tissue was macro-dissected away. Genomic DNA was extracted from the remaining neoplastic regions using a Qiagen DNA Removal for FFPE Samples kit, according to manufacturer's recommendations (Qiagen, Germantown, Md., USA), and subsequently assessed for quality and quantity by spectrophotometry. Genomic DNA integrity was assessed by agarose gel electrophoresis, indicating that while all FFPE derived specimens exhibited some degree of degradation, the majority of the DNA was >10 kb.

Fluorescence In Situ Hybridization (FISH) of Archival Specimens.

In this study, FISH was performed using 5 µm FFPE sections of the cases in the cohort to detect and quantify hybridization sites of target genomic regions. Each 5 µm FFPE section was mounted onto a charged glass slide and incubated at 56° C. for 18 hours in a moisture-free slide chamber. Slides were then de-waxed by soaking in fresh xylene for 15 minutes, dehydrated through an ethanol series, and air-dried. Slides were incubated for 1 hour at 37° C. in 60 mg/mL collagenase II (Sigma, Saint Louis, Mo.) in HBSS (Mediatech, Corning, N.Y.) and then for 45 minutes at 37° C. in Tris-Buffer Saline (Boston BioProducts, Boston, Mass.) containing 15000 unit/mL of Bovine Testicular Hyaluronidase (Sigma, Saint Louis, Mo.). Slides were rinsed with ultrapure water for 3 min between treatments. Sections were then treated with an Abbott Paraffin Pretreatment Kit II according to the manufacturer's recommendation.

Tissue slices were assessed by FISH to evaluate the copy number of canine bacterial artificial chromosome (BAC) probes designed to represent ten genes, selected to correspond to those identified by previous human studies of melanoma; CDKN2A, CDKN1A, PTEN, B-RAF, TP53, CCND1, c-MYC, c-KIT, CDK4, and RB-1. The BACs were selected from the CHORI-82 (https://bacpac.chori.org/library.php?id=253) library based on their genome position indicated in the USCS canine genome browser (http://genome.uscs.edu). To increase the size of the FISH signal for assessment of archival specimens, a probe pool was developed for each locus, comprising three overlapping BAC clones; a primary clone containing the gene of interest and at least one overlapping BAC clone selected on either side. This approach resulted in probe contigs for each locus with DNA sequence extending the final probe size to approximately 500 Kb. A summary of the BAC clones used is shown in SOM Table 1. To verify that each BAC pool had a unique cytogenetic location in healthy cells, all were first hybridized to metaphase preparations from six clinically healthy dogs, generated by conventional mitogen stimulation of peripheral lymphocytes (Breen et al., 1999), using multicolor single locus probe (SLP) FISH analysis as described previously (Breen et al., 2004).

To establish a baseline of expected mean copy number of each probe when hybridized to non-neoplastic FFPE samples, each of the ten probes was first enumerated in nuclei of a series of 5 µm sections of FFPE specimens of healthy tissue matched controls. A minimum of 50 cells was imaged using a BioView Legato system (BioView, Israel) set to acquire multiplane images of 19 adjacent focal planes at 0.5 µm increments. The mean copy number of each probe in >50 nuclei of 5 µm sections of FFPE biopsy specimens was then obtained using the same process, and normalized to the mean of the corresponding controls. Classification of FISH signals as gains or losses was performed as described previously for human diagnostics (Gaiser et al., 2010) where the mean must be based on no fewer than 50 separate cells and aberrant signals must be found in at least 50% of the cell population analyzed.

Comparative Genomic Hybridization (CGH)

Oligo array-CGH (oa-CGH) was performed by co-hybridization of tumor (test) DNA and a common reference DNA sample, where the latter comprised an equimolar pool of genomic DNA samples from multiple healthy individuals of various breeds. DNA extracted from FFPE samples was slightly degraded, as expected, but this was shown not to have an adverse effect on data quality. DNA was labeled using an Agilent SureTag Labeling Kit (Agilent Technologies, Santa Clara, Calif.) with all test samples labeled with Cyanine-3-dCTP and the common reference sample labeled with Cyanine-5-dCTP. Fluorchrome incorporation and final probe concentrations were determined using routine spectrophotometric parameters with readings taken from a Nanodrop1000. Fluorescently labeled test and reference samples were co-hybridized to Canine G3 180,000 feature CGH arrays (Agilent, AMADID 025522) for 40 hours at 65° C. and 20 rpm, as described previously (Angstadt et al., 2011; Thomas et al., 2014). Arrays were scanned at 3 µm using a high-resolution microarray scanner (Agilent, Model G2505C) and data extracted using Feature Extraction (v10.9) software. Scan data were assessed for quality by the 'Quality Metrics' report in Agilent's Feature extraction software (v10.5) (Agilent Technologies).

Copy number data were analyzed with NEXUS Copy Number v7.0 software (Biodiscovery Inc., CA, USA). The raw copy number data for each probe provided from Feature Extraction were centered using diploid regions. NEXUS generated copy number aberrations using a FASST2 segmentation algorithm with a significance threshold of $5.05^{-6}$. Aberrations were defined as a minimum of three consecutive probes with log 2 tumor: reference value of >1.14 (high gain), 1.13 to 0.2 (gain), −0.23 to −1.1 (loss), <−1.1 (big loss). Recurrent copy number aberrations within each subtype were determined within NEXUS using an involvement threshold of 50%. Significance of these regions was then determined in NEXUS using the GISTIC algorithm (to identify regions with a statistically high frequency of copy number aberrations over background) with a G-score cut off of G>1.0 and a significance of Q<0.05. Copy number aberration (CNA) frequency comparisons amongst sample groups were performed in NEXUS using Fisher's exact test with differential threshold of >50% and significance p<0.05. Significance of each probe between the two groups was calculated in NEXUS using a Mann-Whitney Test for median comparison.

Humanization of Canine CGH Data

Canine oaCGH data were recoded into 'virtual' human genome format to facilitate direct visual comparison of cytogenetic profiles of human and canine melanoma, as described previously (Thomas et al., 2011). Briefly, the genome coordinates of each of the 180,000 60-mer canine oligonucelotides were imported into the Liftover Batch Coordinate Conversion Tool (http://genome.ucsc.edu/cgi-bin/hgLiftOver), using default settings to establish the orthologous nucleotide sequence coordinates within the human genome sequence assembly (February 2009, GRCh37/hg19). Using these recoded coordinates, the tumor:reference signal intensity data for each array were reprocessed to output the oaCGH profile according to these 'virtual' human chromosome locations.

Clustering of oaCGH Profiles

Hierarchical clustering was performed to evaluate how genome-wide CGH profiles differentiate between the two groups. Hierarchical clustering using Ward's method for linkage was performed on the genome-wide log 2 ratio data for each sample. Analysis was performed using the R statistical software, version 2.13.0 (R Development Core Team, Vienna, Austria) using the gplots package.

Statistical Analysis of oaCGH and Histology Profiles

Correlation analysis was performed between oaCGH clusters and the corresponding histological characteristics to determine if DNA copy number aberrations were significantly associated with pathological cellular morphologies. Initial analysis was based on pathological diagnosis alone. To test molecular association, two clusters were established based on oaCGH copy number profiles as performed above. These two groups were then assessed for statistical differences between histological characteristics. A Wilcoxon rank-sum test was performed for pigmentation and log mitotic values and a Fisher's exact test was performed for association analysis with group status and nuclear atypia.

6.3. Results

Clinical Assessment

A total of 49 canine melanomas and 18 benign melanocytomas were profiled by oaCGH during this study. Melanomas presented from two locations: the oral cavity (n=44) and unspecified haired skin (n=5). Benign melanocytomas presented primarily from haired skin (n=13) with rare presentation from the oral cavity (n=5). Breed was not a consideration in case selection and so there were 29 breeds of dog included in this study, with the most frequent being dogs of mixed breed (n=14), accounting for 21% of cases. Overall melanomas presented with a more aggressive histologic presentation including a significantly higher mitotic index (p=3.81085E-06), lower percent pigmentation (p=0.000116571), and higher percent nuclear atypia (p=1.83334E-10). A detailed summary of the histopathologic findings of each case is presented in Table 2.

Detection of CNA by oaCGH

Individuals represented within the oral (mucosal) melanoma cohort presented with highly complex genome-wide oaCGH profiles (FIG. 4). In most cases, the oaCGH profiles showed regions of the genome where the $\log_2$ ratios of test:reference signal indicated either a unidirectional gain or loss of one copy of a locus within the majority of cells of the tumor, or a high level of cellular heterogeneity within the tumor cell population. This was clarified by FISH analysis of copy number within individual cells, which corroborated single copy aberrations (described below). Highly recurrent CNAs (>50% penetrance across the cohort) were assessed in detail (Table 3). For the cohort of oral melanomas the most frequent DNA copy number gain was a 600 Kb region of dog chromosome (CFA) 30 located at CFA30:19,102,383-19,660,901 (q=4.25E-10), along with whole chromosome gains of CFA 13, 17, 20, 29, and 36. The most frequent DNA copy number losses involved the full lengths of CFA 22 and 27, as well as 15 Kb and 122.5 Kb segments located at CFA10: 20,583,579-20,598,892 (q=6.26E-05), and CFA26:30,241,704-30,306,343 (q=1.34E-08), respectively.

Several regions of the genome had oaCGH profiles suggestive of structural changes, denoted by a copy number gain followed immediately by a loss, most notably on CFA10 and CFA30, both of which were found to be statistically significant using the GISTIC algorithm (Table 4). The chromosome break point region on CFA 30, evident in 60% of the oral melanomas analyzed, spans 5 Mb of sequence located between 14 Mb and 19 Mb (FIG. 2). The log 2 values within this region of CFA30 were suggestive of a heterozygous loss followed by an immediate gain, with 97% of affected cases suggestive of a copy number of ≥4.

Cutaneous melanomas, although small in number (n=5), also presented with highly aberrant oaCGH profiles (FIG. 4). The largest and most common aberration was a gain of CFA 20 that spanned 46.2 Mb of the chromosome CFA20:10,929,869-57,175,686, present in four of the five cases. The most frequent copy number losses were a 131 kb region of CFA6:48,260,040-49,569,575, a 385 Kb region of CFA18:21,439,849-21,824,376 and the full length of chromosome 22. Due to the small number of cases none of these aberrations were statistically significant using the GISTIC algorithm (Table 4).

While individuals represented within the benign/cutaneous melanocytoma cohort (n=18) presented with relatively stable oaCGH profiles, some recurrent aberrations were evident (FIG. 4). The most common aberration was gain of a 87 Kb region of CFA27 CFA27: 9,965,501-10,052,495 (q=3.40E-13). Other common aberrations were gains on CFA9:20,973,038-21,556,711 (q=4.89E-09), CFA10:48,818,794-48,878,597 (q=3.95E-05), and CFA11:55,214,228-55,245,594 (q=4.99E-08). Melanocytomas had one significant recurrent copy number loss, a 200 Kb region at CFA8: 76,368,492-76,582,392 (q=7.78E-04).

Comparison of Melanomas to Melanocytomas

A number of CNAs were either detected in only one subtype, or were shared between two of the three subtypes (Table 5). Cutaneous melanomas and melanocytomas shared several common recurrent aberrations that were rare or absent in oral melanomas, most significantly a 17.5 Mb region of gain at CFA20:39,655,694-57,175,686, found approximately 45% in melanocytomas and 80% in cutaneous melanomas (in CM q<0.01). Another notable similarity between these two groups was the presence of a 9 Mb copy number gain between 35 Mb and 44 Mb on chromosome 30 (FIG. 5). There were no aberrations shared between cutaneous and oral melanomas at the 50% differential level. However, when the stringency was dropped to 40% several regions were found in common, including a 140 Kb loss of CFA3:65,280,294-65,432,693 and a 260 Kb gain of CFA13: 8,127,632-8,394,801 (data not shown). Aberrations unique to one subtype were also evident. Deletion of a 385 Kb segment of CFA18 at CFA18:21,439,849-21,824,376 was highly recurrent only in cutaneous melanomas and a complex copy number profile along a 13 Mb region of CFA30 CFA30:8,290,472-21,411,530 was observed only in oral melanomas.

Hierarchical Clustering of All Melanocytic Lesions

Hierarchical clustering of segmented oaCGH profiles separated samples into three well-defined groups (FIG. 3). The first and third group contained only malignant samples while the second group contained an equal mix of benign (n=17) and malignant samples (n=21). The clustering of 21 malignant samples with the benign samples is partially explained by the reduced level of aberrations within those particular malignant lesions. Within this larger group, the malignant samples and benign samples also appear to cluster separately.

Clusters were further evaluated by consideration of their histological characteristics, to identify correlation of cellular morphology with genome-wide CGH profiles. The malignant samples that clustered with benign samples (n=21) showed significantly higher pigmentation (p=0.018), lower mitotic index (p=0.023), and a lower, but not statistically significant, nuclear atypia (p=0.222) than the group of malignant melanomas that clustered together (n=28). These data demonstrate that molecular aberrations in canine malignant melanomas correlate with the cellular phenotype and histology, suggesting the potential utility of molecular markers to differentiate between histologically ambiguous lesions.

Detection of CNA by FISH Analysis of FFPE Sections

All targeted loci (n=10) evaluated by FISH analysis showed aberrant copy number in oral melanomas. The most frequent unidirectional changes were a gain of c-MYC (80% of cases) and loss of CDKN2A (68% of cases) and RB1 (35% of cases). The other seven loci evaluated showed bidirectional changes (FIG. 7a). As expected, based on the whole genome oaCGH data, benign lesions showed lower percentages of targeted locus aberrations (FIG. 7b). The most common of the targeted CNAs evident in the benign lesions were loss of TP53 and CDKN2A. It is important to note that these aberrations were observed only as a heterozygous loss, indicating the retention of one allele for production of downstream product (if unmutated). Interestingly, neither tumor types showed significant copy number amplification of regions encompassing BRAF or CCND1, both of which are highly aberrant in human UV-induced cutaneous melanomas. The population of canine oral melanomas showed a combination of both copy number gain and loss for these gene regions, suggesting overall chromosome instability, but not targeted gene amplification.

Comparison of Canine to Human Melanocytic Lesions

Humanization of the canine oaCGH data allowed for direct comparison of the canine data collected in this study to the CNA status of human melanomas accessible from previous studies. When aligned with genome wide oaCGH profiles of different subtypes of human melanoma, striking similarities were present between canine oral melanoma, and both human mucosal melanoma and human acral melanoma (FIG. 8). Human mucosal and acral melanomas have been shown to present with more complex genome-wide oaCGH profiles than cutaneous melanomas (Curtin et al., 2005; Furney et al., 2012; Thomas et al., 2014), paralleling the data for canine melanomas in the current study. Many CNAs were shared between human and dog, including a characteristic complex oaCGH profile involving the evolutionarily conserve chromosome segments represented by human chromosome chr15:38,701,609-49,824,200 and canine chromosome CFA30:8,290,472-21,411,530. Notably, this distinct aberration was not detected in canine cutaneous melanomas, or in human common cutaneous melanomas. Human mucosal and acral melanomas showed additional smaller shared aberrations (Table 8).

6.4. Discussion

Aberrations within Melanomas and Melanocytomas: Tumorigenesis Implications

As with human melanomas, canine melanomas present with cytogenetically distinct profiles based on malignancy and the anatomic location in which they arise. The most striking evidence of this is the presence of a characteristic aberration of CFA30 in oral melanomas, which is absent in cutaneous lesions. Melanocytomas, which are primarily cutaneous, had noticeably fewer aberrations than both subtypes of melanoma. However, approximately 40% of these were shared with cutaneous melanoma, including the recurrent copy number gain of CFA20:39,655,694-57,175,686, evident in cutaneous but not oral lesions (Table 4). These features may represent hallmarks of an epithelial growth pattern and targeted investigation into this region may elucidate tumor initiation specific to this tissue location. There are also significant clinical implications of the molecular differentiation of the two locations. The separation of these two diseases provides insight into the initiation and development of the different subtypes of melanomas and could lead to the development of specific treatment regimens based on the site of primary tumor growth.

The most recurrent aberration specific to the oral melanoma cohort was the distinctive complex copy number profile on CFA30, present in 60% of cases and indicative of a structural rearrangement. Due to the high incidence of this particular complex CNA it is probable the rearrangement on CFA30 is also key to the development of canine oral melanoma, or progression towards a malignant phenotype. This aberration may be of potential for use as a signature to differentiate between lesions that are likely to progress, requiring additional treatments, and those that are likely to remain benign. Further study into the cause and biological effect of the breakage may also provide further insight into why oral melanomas are behaviorally more aggressive than other melanocytic subtypes. The 5 Mb region of genome sequence surrounding the breakage (CFA30:15 Mb-20 Mb) is within a gene desert, surrounded by gene rich areas. This is reminiscent of unstable chromosome regions in the human genome, such as the breakpoint cluster region (BCR) at 22q11.23.

Within the complex region of CNA on CFA30 are nine annotated genes, six of which were subject to increase in copy number and three to decrease in copy number (Table 5). One gene with a copy number loss was SPRED1, a suppressor of Ras/MAP-K activation. Since deletion of SPRED1 can positively regulate the activation of the RAS/MAP-K pathway, this aberration in canine melanoma suggests a possible mechanism of tumorigenesis. The involvement of the MAP-K pathway is also supported by the presence of the gene TRPM7, located within the region of copy number gain on CFA30. Increase in gene dosage may be associated with increased expression, and overexpression of TRPM7 has been shown to be involved in both melanoma development (Guo et al., 2012) and the regulation of the MAP-K pathway (Meng et al., 2013). Additionally, targeted FISH analysis of canine oral melanomas indicated copy number gain of both C-KIT, which initiates the RAS/MAP-K pathway, and C-MYC, which is downstream of the MAP-K phosphorylation cascade. Both C-MYC and C-KIT showed copy number gain in canine oral melanomas (80% and 65% of cases respectively). This further supports the involvement of the MAP-kinase signaling pathway in the development of canine oral melanomas.

Aberrations detected in both malignant forms of canine melanoma, but not in melanocytomas, suggest that these specific mutations are essential for the development of malignant and aggressive neoplasms. This was further confirmed by the high degree of correlation between patterns of genome-wide CNAs and cellular histology. Malignant melanomas presenting with less complex oaCGH profiles (similar to those of benign lesions) had significantly different cellular morphologies to those with complex copy number profiles. This confirms the molecular basis of cellular phenotype and suggests that specific CNAs present within these particular malignant lesions give rise to a more malignant phenotype. Regions of shared CNA within the malignant populations contain numerous genes (Table 6). Based on the cellular function of each protein, the dysregulation of these genes may offer molecular insight into the development of malignant characteristics, including complex genome-wide CNAs, dedifferentiated cell morphologies, and presentation of histologically ambiguous features. For example, the most frequent aberration observed in both cutaneous and oral melanomas was a copy number loss of the segment CFA3: 62,368,641-62,381,281. Within this region is the coding sequence for TACC3, which acts as a stabilizer of mitotic spindles during mitosis and has been proposed to play a role in cell differentiation.

All ten loci evaluated by FISH analysis showed aberrant copy number in canine oral melanomas. Seven of the loci evaluated showed a combination of gains and losses, suggesting more random genomic instability at these regions than targeted functional pathway alterations. This suggestion is supported by the fact that no homozygous losses and few high amplification events were detected involving any of these seven loci. Three genes showed only unidirectional CNA among the cohort, C-MYC, RBb1, and CDKN2A, suggesting these are not merely random CNAs due to end stage mitotic instability, but targeted alterations advantageous to tumor development. The dysregulation of mRNA expression in these genes has been previously established (Bianco et al., 2003; Koenig et al., 2002; Ritt et al., 1998). The identification of the presence of these CNAs now offers a mechanism with which tumor cells regulate gene expression leading to tumorigenesis of canine oral melanoma.

Comparison of Canine to Human Melanocytic Lesions

Oral mucosal melanomas in humans are rare and poorly understood, representing only 2% of all melanomas (Chang et al., 1998). Due to the small number of cases, limited large-scale genomic research has been performed and so details of the genetics of development of mucosal melanomas and the majority of genetic drivers remain unknown. Through clinical observations of similar anatomical location and behavior, it has been proposed that the mucosal subtype of human melanoma would be analogous to oral canine melanomas, which would support the use of the dog as a model system to study the development of these rare tumors. Curtain and colleagues first assembled cytogenetic hallmarks of human acral and mucosal melanoma through BAC-array CGH in 2005 (Curtin et al., 2005). Using those published data as a reference, we were able to directly compare CNAs reported in these forms of human melanoma with those identified in canine cases in the present study. The comparison revealed mucosal melanomas in both species to have a much more complex genome-wide copy number profile. This is suggestive of decreased genome stability and increased susceptibility to karyotype rearrangements, corroborated by recent whole-genome sequence data (Furney et al., 2012; Thomas et al., 2014). In general, the CNAs most common to canine melanoma were shared with those detected in human mucosal melanomas. Further, the canine CNAs were different to those evident in UV-induced human cutaneous melanomas, which also differ from human mucosal melanomas. The most remarkable similarity between canine melanomas and their human orthologous was a conserved and complex copy number profile along the length of CFA30/HSA15. The characteristic copy number signature on HSA15 has been reported only in mucosal and acral melanomas. We propose that this characteristic feature is associated with a key evolutionarily conserved mechanism of pathogenesis in the development and/or progression of mucosal melanomas. It was also noted that no individual within the canine data set showed the characteristic BRAF amplification or associated CCND1 amplification commonly detected in UV-induced cutaneous melanomas in humans. Other notable conserved mutations are seen as a gain on CFA 13 (cf HSA chr4:70,508,745-70,808,489), loss of CFA 4 and 11 (cf HSA chr5:50,515,301-76,556,132), and gain of CFA 10 and 26 (cf HSA chr12:48,133,151-52,785,962). These data indicate the underlying pathway of development in all mucosal melanomas, regardless of species, may be different to that of cutaneous UV-induced melanomas. They also encourage more detailed and statistically powerful studies of the etiology and treatment of mucosal melanomas.

In agreement with other recent proposals (Gillard et al., 2014; Simpson et al., 2014), our data further supports the role of the dog model as a valuable aide in the study of disease pathogenesis of non-UV induced mucosal melanomas. Previous comparative studies of melanoma have relied solely on histology and targeted sequencing, highlighting the dissimilarity of canine melanoma and human common cutaneous melanoma, and limited homology with mucosal melanomas. The genome-wide molecular cytogenetic analysis in this study revealed remarkable similarities shared between human and dog mucosal melanomas. These data suggest that pathways specific to melanogenesis of mucosal surfaces may be elucidated by a comparative oncology approach, with integrated consideration of omics data from both species.

Table 2. Histological description of primary tumors from formalin fixed paraffin embedded (FFPE) and fresh frozen samples.

Table 3. Genome wide DNA copy number aberrations with at least 50% penetrance for three subtypes of canine melanocytic lesions, oral melanoma (OM), benign melanocytoma (B), and cutaneous melanoma (CM).

Table 4. Significant genome wide DNA copy number aberrations using GISTIC for three subtypes of canine melanocytic lesions, oral melanoma (OM), benign melanocytoma (B), and cutaneous melanoma (CM). In each case regions with significant copy number gain are presented before regions with significant copy number loss. The G-score considers the amplitude of the aberration as well as the frequency of its occurrence across samples. False Discovery Rate q-values are then calculated for the aberrant regions Table 5. Differential chromosome regions with CN aberrations between primary canine oral melanoma (OM), primary canine cutaneous melanoma (CM), and canine benign melanocytoma (B).

Table 6. Proposed genes involved in canine oral melanoma pathogenesis.

Table 7. Aberrations with at least 60% penetrance for three subtypes of canine melanocytic, oral melanoma (OM), cutaneous melanoma (CM), and melanocytoma (B) lesions after recoding as human (HSA).

Table 8. Homologous copy number aberrations, gain (G) or loss (L), between canine (CFA) melanocytic lesions, malignant melanoma (Mel) and benign melanocytomas (Ben) and two human (HSA) melanoma subtypes, mucosal melanoma (mucosal) and acral melanoma (acral).

Table 9. Targeted regions for FISH analysis with the corresponding BAC clones and locations chosen from the Chori-82 (CH-82) canine genome library.

FIG. 4. aCGH analysis of primary canine oral melanoma (OM), primary canine cutaneous melanoma (CM) and canine cutaneous melanocytoma (B).

Penetrance plots of recurrent CNAs, at 26 kb intervals, identified within 67 canine melanocytic lesions. Genomic locations are plotted along the x-axis, and the y-axis indicates the percentage of the three subtypes with copy number gain (shown above the midline) or loss (shown below the midline) of the corresponding intervals along each chromosome. In oral melanomas (OM, n=44) the most frequent gain was located on CFA chr30: 18,527,413-18,592,465, along with whole chromosome gains of CFA 13, 17, 20, 29, and 36. The most frequent losses were found on CFA chr10: 20,583,579-20,598, 892, chr26: 30,241,704-30,306,343, chr30: 10,620,776-10,658,526 and all of CFA 2, 22, and 27. In cutaneous melanomas (CM, n=5) the largest and most common aberration was a gain of CFA chr20:10,929,869-57,175,686. In melanocytomas (B, n=18) the most frequent aberration was a gain of a small region of CFA chr27:9,965,501-10,052,495, as well as less frequent gains on CFA chr9:20,973,038-21,556,711, chr10:48,818,794-48,878,597, and chr11:55,214,228-55,245,594.

FIG. 5. Penetrance plots of DNA copy number aberrations along the length of CFA chromosome 30 in oral melanomas (OM), cutaneous melanomas (CM) and melanocytomas (B). Oral melanomas showed a distinct pattern of copy number loss (spanning 3-18 Mb) partially overlapping a region of copy number gain (spanning 12-25 Mb), indicative of a variable chromosome breakage event. This breakage region, centered at 15 Mb-18 Mb was not present in either cutaneous melanomas or benign melanocytomas. 50% (n=9) of melanocytomas showed a gain of two small regions at the distal end of chromosome 30 (35-37 Mb and 40-42 Mb), also seen in 20% (n=1) of cutaneous melanomas.

FIG. 6. Clustering analysis of 31 cases of primary canine oral melanoma, five cases of primary canine cutaneous melanoma, and 15 primary canine melanocytomas based on genome-wide oaCGH profiles. Segmented oaCGH profiles were subjected to hierarchical clustering. Individual cases are plotted along the x-axis, with chromosomes plotted along the y-axis. Cases were grouped and a linage tree of relatedness schematic is drawn above. Dark gray, light gray and white represent CN gain, loss, and neutrality. The CN log 2 ratio is represented in the intensity of the coloration gradient as per the inset. Bars above each sample indicate malignant (light gray) or benign (dark gray) cases. In general, cases with more complex copy number profiles clustered together. There were 21 malignant melanomas, each with few copy number aberrations, which clustered into the same bin as all but one of the benign lesions. Further analysis showed these 21 cases showed histological characteristics significantly different from melanomas that clustered together. The one benign lesion that crusted with a group of malignant lesions had two whole chromosome gains, CFA 31 and X.

FIGS. 7A and 7B. Penetrance of aberration of 10 specific genomic regions in (7A) primary canine oral melanoma and (7B) canine melanocytoma. Gains and losses are plotted above or below the x-axis respectively. The length of the bar represents the percentage of the sampled population that showed a particular aberration (y-axis). Full locus identity and location are provided in Table 9. Canine oral melanomas showed higher percentage of cases with targeted genomic aberrations than benign melanocytomas, validating the oaCGH data. It also revealed targeted regions with unidirectional changes, suggesting their involvement in downstream pathway dysregulation and tumorigenesis.

FIG. 8. Canine oral melanoma (OM), cutaneous melanoma (CM), and benign melanocytoma (B) oaCGH profile data recoded as human. Canine oral melanomas (n=44), cutaneous melanomas (n=5), and cutaneous melanoctyomas (n=18) were recoded and output with human genome coordinates. This allowed for comparison to known aCGH profiles compiled for human melanoma subtypes. Hallmarks of human mucosal melanoma are copy number amplification of 1q31, 4q12, 12q14, 11q13, 8q, and 6p as well as copy number loss of 3q, 4q, 8p, 10, 11p, and 21q (Curtain et al, 2005). Similar aberrations were found within the canine oral melanoma population. Most notably, the breakage area on CFA 30 matches a similar pattern of loss followed by gain seen on HSA chromosome 15, the orthologous region on the human genome.

FIG. 9. Comparison of fresh frozen and formalin fixed paraffin embedded tissues from the same tumor biopsy by oaCGH. To demonstrate that both fresh frozen and fixed biopsy specimens of could be in used in the same study, DNA from several sample pairs was assessed. In this example oaCGH profiles are shown from data obtained using DNA isolated from A) a frozen piece of tissue and B) 3×25 µm sections of the corresponding FFPE specimen, after macrodissection to enrich for tumor cells. Analysis was completed in Agilent Genomic Workbench with CNAs called using the ADM6 algorithm. Chromosomes are presented along the x-axis with log 2 ratio of copy number changes presented along the y-axis centered at y=0. (C) Shows an overlay of the two oaCGH profiles in A (dark gray) and B (light gray). The dark gray and light gray bars above and below the combined profiles indicate the size of called aberrations in the fresh and fixed tissue profiles, respectively. These data demonstrate that while the amplitude of called events was slightly higher in the marcodissected FFPE specimen, both fresh and fixed tissue presented with the same ADM2 called aberrations.

7. REFERENCES

Angstadt, A. Y., Motsinger-Reif, A., Thomas, R., Kisseberth, W. C., Guillermo Couto, C., Duval, D. L., Nielsen, D. M., Modiano, J. F., and Breen, M. (2011). Characterization of canine osteosarcoma by array comparative genomic hybridization and RT-qPCR: Signatures of genomic imbalance in canine osteosarcoma parallel the human counterpart. Genes, Chromosomes and Cancer 50, 859-874.

Bastian, B. C., Olshen, A. B., LeBoit, P. E., and Pinkel, D. (2003). Classifying Melanocytic Tumors Based on DNA Copy Number Changes. The American Journal of Pathology 163, 1765-1770.

Bauer, J., and Bastian, B. C. (2006). Distinguishing melanocytic nevi from melanoma by DNA copy number changes: comparative genomic hybridization as a research and diagnostic tool. Dermatologic Therapy 19, 40-49.

Bergman, P. (2007). Canine Oral Melanoma. Clinical Techniques in Small Animal Practice 22, 55-60.

Bianco, S. R., Sun, J., Fosmire, S. P., Hance, K., Padilla, M. L., Ritt, M. G., Getzy, D. M., Duke, R. C., Withrow, S. J., Lana, S., et al. (2003). Enhancing antimelanoma immune responses through apoptosis. Cancer Gene Therapy 10, 726-736.

Blokx, W. A. M., van Dijk, M. C. R. F., and Ruiter, D. J. (2010). Molecular cytogenetics of cutaneous melanocytic lesions â "diagnostic, prognostic and therapeutic aspects. Histopathology 56, 121-132.

Breen, M. (2009). Update on Genomics in Veterinary Oncology. Topics in Companion Animal Medicine 24, 113-121.

Breen, M., Bullerdiek, J., and Langford, C. F. (1999). The DAPI banded karyotype of the domestic dog (Canis familiaris) generated using chromosome-specific paint probes. Chromosome Research 7, 575.

Breen, M., Hitte, C., Lorentzen, T. D., Thomas, R., Cadieu, E., Sabacan, L., Scott, A., Evanno, G., Parker, H. G., Kirkness, E. F., et al. (2004). An intergrated 4249 marker FISH/RH map of the canine genome. BMC Genomics 5, 65.

Chang, A. E., Karnell, L. H., and Menck, H. R. (1998). The National Cancer Data Base report on cutaneous and noncutaneous melanoma. Cancer 83, 1664-1678.

Curtin, J. A., Fridlyand, J., Kageshita, T., Patel, H. N., Busam, K. J., Kutzner, H., Cho, K., Aiba, S., Bröcker, E., LeBoit, P. E., et aL (2005). Distinct Sets of Genetic Alterations in Melanoma New England Journal of Medicine 353, 2135-2147.

Furney, S. J., Turajlic, S., Fenwick, K., Lambros, M. B., MacKay, A., Ricken, G., Mitsopoulos, C., Kozarewa, I., Hakas, J., Zvelebil, M., et aL (2012). Genomic Characterisation of Acral Melanoma Cell Lines. Pigment Cell & Melanoma Research, no-no.

Gaiser, T., Kutzner, H., Palmedo, G., Siegelin, M. D., Wiesner, T., Bruckner, T., Hartschuh, W., Enk, A. H., and Becker, M. R. (2010). Classifying ambiguous melanocytic lesions with FISH and correlation with clinical long-term follow up. Modern Pathology 23, 413-419.

Gillard, M., Cadieu, E., De Brito, C., Abadie, J., Vergier, B., Devauchelle, P., Degorce, F., Dréano, S., Primot, A., Dorso, L., et al. (2014). Naturally occurring melanomas in dogs as models for non-UV pathways of human melanomas. Pigment Cell & Melanoma Research 27, 90.

Guo, H., Carlson, J. A., and Slominski, A. (2012). Role of TRPM in melanocytes and melanoma. Experimental Dermatology 21, 650-654.

Koenig, A., Bianco, S. R., Fosmire, S., Wojcieszyn, J., and Modiano, J. F. (2002). Expression and Significance of p53, Rb, p21/waf-1, p16/ink-4a, and PTEN Tumor Suppressors in Canine Melanoma. Veterinary Pathology 39, 458-472.

Kudnig, S. T., Ehrhart, N., and Withrow, S. J. (2003). Survival Analysis of Oral Melanomas in Dogs. Veterinary Cancer Society Proceedings 23.

Meng, X., Cai, C., Wu, J., Cai, S., Ye, C., Chen, H., Yang, Z., Zeng, H., Shen, Q., and Zou, F. (2013). TRPM7 mediates breast cancer cell migration and invasion through the MAPK pathway. Cancer Letters 333, 96-102.

Newman, S. J., Jankovsky, J. M., Rohrbach, B. W., and LeBlanc, A. K. (2011). C-kit Expression in Canine Mucosal Melanomas. Veterinary Pathology 49, 760-765.

Overly, B., Goldschmidt, M. H., and Schofer, F. (2001). Canine Oral Melanoma: A Retrospective Study. Veterinary Cancer Society Proceedings 21.

Ramos-Vara, J. A., Beissenherz, M. E., Miller, M. A., Johnson, G. C., Pace, L. W., Fard, A., and Kottler, S. J. (2000). Retrospective Study of 338 Canine Oral Melanomas with Clinical, Histologic, and Immunohistochemical Review of 129 Cases. Veterinary Pathology 37, 597-608.

Ritt, M. G., Wojcieszyn, J., and Modiano, J. F. (1998). Functional Loss of p21/Waf-1 in a Case of Benign Canine Multicentric Melanoma. Veterinary Pathology 35, 94-101.

Simpson, R. M., Bastian, B. C., Michael, H. T., Webster, J. D., Prasad, M. L., Conway, C. M., Prieto, V. M., Gary, J. M., Goldschmidt, M. H., Esplin, D. G., et al. (2014). Sporadic naturally occurring melanoma in dogs as a preclinical model for human melanoma. Pigment Cell & Melanoma Research 27, 37-47.

Smedley, R. C., Spangler, W. L., Esplin, D. G., Kitchell, B. E., Bergman, P. J., Ho, H. Y., Bergin, I. L., and Kiupel, M. (2011). Prognostic Markers for Canine Melanocytic Neoplasms: A Comparative Review of the Literature and Goals for Future Investigation. Veterinary Pathology 48, 54-72.

Smith, S. H., Goldschmidt, M. H., and McManus, P. M. (2002). A Comparative Review of Melanocytic Neoplasms. Veterinary Pathology 39, 651-678.

Spangler, W. L., and Kass, P. H. (2006). The Histologic and Epidemiologic Bases for Prognostic Considerations in Canine Melanocytic Neoplasia. Veterinary Pathology 43, 136-149.

Thomas, R., Borst, L., Rotroff, D., Motsinger-Reif, A., Lindblad-Toh, K., Modiano, J. F., and Breen, M. (2014). Genomic profiling reveals extensive heterogeneity in somatic DNA copy number aberrations of canine hemangiosarcoma. Chromosome Research in press.

Thomas, R., Seiser, E. L., Motsinger-Reif, A., Borst, L., Valli, V. E., Kelley, K., Suter, S. E., Argyle, D., Burgess, K., Bell, J., et al. (2011). Refining tumor-associated aneuploidy through 'genomic recoding' of recurrent DNA copy number aberrations in 150 canine non-Hodgkin lymphomas. Leukemia and Lymphoma 52, 1321-1335.

Villamil, J. A., Henry, C. J., Bryan, J. N., Ellersieck, M., Schultz, L., Tyler, J. W., and Hahn, A. W. (2011). Identification of the most common cutaneous neoplasms in dogs and evaluation of breed and age distributions for selected neoplams. JAVMA 239, 960-965.

Withrow, S. J., D. M. Vail, and R. Page (2013). Small Animal Clinial Oncology, 5 edn (Elsevier). Xie, T., G, D. A., Lamb, J. R., Martin, E., Wang, K., Tejpar, S., Delorenzi, M., Bosman, F. T., Roth, A. D., Yan, P., et al. (2012). A comprehensive characterization of genome-wide copy number aberrations in colorectal cancer reveals novel oncogenes and patterns of alterations. PloS one 7, e42001.

TABLE 2

| Tissue descriptions | | | | | | | | | |
|---|---|---|---|---|---|---|---|---|---|
| FFPE Oral Melanomas | | | | | Mit. | | Nuc. | Junct | Tissue |
| Case | Primary Site | Breed | Age | Sex | Index | Pigm. | Atypia | Act. | Subtype |
| OM 1 | Oral - Mandible w/g&t | Golden Retriever | 11 Y | F | 41 | <5% | high | yes | mixed |
| OM 2 | Oral - Caudal oral cavity | English Shepard Dog | 9 Y | M | 13 | <5% | high | yes | polygonal |
| OM 3 | Oral - Gum | Airedale Terrier | 11 Y | F | 8 | 40% | low | no | mixed |
| OM 4 | Oral - Maxilla | Scottish Terrier | 10 Y | F | 39 | 0% | high | no | spindeloid |
| OM 5 | Oral | Golden Retriever | 9 Y | F | 48 | 10% | high | N/J/A | spindeloid |
| OM 6 | Oral | Mixed | 10 Y | M | 50 | 5% | high | no | polygonal |
| OM 7 | Oral | Schipperke | 14 Y | M | 44 | 0% | med | N/J/A | spindeloid |
| OM 8 | Oral | Rottweiler | 6 Y | M | 34 | 50% | high | N/J/A | polygonal |
| OM 9 | Oral | Beagle | 12 Y | F | 4 | 50% | high | yes | polygonal |
| OM 10 | Oral | Cocker Spaniel | n/a | M | 140 | 0% | high | yes | polygonal |
| OM 11 | Oral | not identified | 16 Y | M | 8 | 0% | high | no | spindeloid |
| OM 12 | Oral | Australian Shepherd | 8 Y | M | 2 | 50% | low | yes | mixed |
| OM 13 | Oral | Labrador Retriever | 10 Y | M | 42 | 5% | high | yes | polygonal |
| OM 14 | Oral | Yorkshire Terrier | 11 Y | F | 26 | 50% | med | yes | polygonal |
| OM 15 | Oral | Labrador Retriever | 9 Y | M | 48 | 0% | med | yes | polygonal |
| OM 16 | Oral | Golden Retriever | 9 Y | F | too pigmented | 100% | low | N/J/A | spindeloid |
| OM 17 | Oral | Mixed | 13 Y | M | 170 | 0% | high | no | mixed |
| OM 18 | Oral | Mixed | n/a | F | 85 | 5% | low | mixed | spindeloid |
| OM 19 | Oral | Labrador Retriever | 13 Y | M | 3 | 10% | high | mixed | ulcerated mix |
| OM 20 | Oral - Lip | Jack Russel Terrier | 10 Y | F | 11 | 5% | low | N/J/A | polygonal |
| OM 21 | Oral | Not Identified | 15 Y | F | 34 | 0% | low | N/J/A | mixed |
| OM 22 | Oral | Lhasa Apso | 15 Y | F | 9 | <5% | low | yes | ulcerated polygonal |
| OM 23 | Oral | Mixed | 14 Y | M | 14 | 0% | high | yes | mixed |
| OM 24 | Oral | Labrador Retriever | 8 Y | M | too pigmented | 95% | low | yes | mixed |
| OM 25 | Oral | Cocker Spaniel | 13 Y | M | 12 | 50% | low | no | polygonal |
| OM 26 | Oral | Mixed | 10 Y | F | 5 | 20% | high | yes | necrotic spindeloid |
| OM 27 | Oral | English Springer Spaniel | n/a | F | 6 | 0% | high | no | spindeloid |
| OM 28 | Oral | Not Identified | 13 Y | F | 33 | <5% | mid | no | polygonal |
| OM 29 | Oral | Pekinese | 14 Y | M | 12 | 0% | high | yes | polygonal |
| OM 30 | Oral | Flat Coated Retriever | 10 Y | M | 50 | 0% | high | N/J/A | mixed |
| OM 31 | Oral | Gordon Setter | 11 Y | M | 18 | 5% | high | no | mixed |
| OM 32 | Oral | Yorkshire Terrier | 9 Y | M | 7 | 10% | low | no | spindeloid |

| Cases | Primary Site | Breed | Age | Sex | Mitotic Index | Pigm. | Nuc. Atypia | Junct. Act. | Tissue Subtype |
|---|---|---|---|---|---|---|---|---|---|
| Fresh Oral Melanomas | | | | | | | | | |
| OM 33 | Oral | Mixed | n/a | M | 67 | >50% | high | yes | mixed |
| OM 34 | Oral | Mini Schnauzer | n/a | F | 0 | >50% | low | no | polygonal |
| OM 35 | Oral | Belgian Malamute | n/a | F | 3 | <5% | high | N/J/A | spindeloid |
| OM 36 | Oral | Mixed | n/a | M | 15 | >50% | high | yes | mixed |
| OM 37 | Oral | Poodle | n/a | M | 19 | <5% | high | N/J/A | polygonal |

TABLE 2-continued

Tissue descriptions

| | | | | | | | | | | |
|---|---|---|---|---|---|---|---|---|---|---|
| OM 38 | Oral | Mini Schnauzer | 10 | Y | F | 26 | 70% | med | yes | spindeloid |
| OM 39 | Oral | Labrador Retriever | 14 | Y | F | n/a | 0% | n/a | n/a | n/a |
| OM 40 | Oral | Mixed | 14 | Y | F | 0 | 50% | no | N/J/A | polygonal |
| OM 41 | Oral | German Shorthaired Pointer | 10 | Y | F | 5 | 50% | high | N/J/A | polygonal |
| OM 42 | Oral | Cocker Spaniel | 10 | Y | M | n/a | 0% | high | N/J/A | polygonal |
| OM 43 | Oral | Poodle | 12 | Y | F | 40 | 0% | med | N/J/A | mixed |
| OM 44 | Oral | English Setter | 11 | Y | F | 15 | 0% | high | yes | polygonal |
| FFPE Melanocytomas | | | | | | | | | | |
| B 1 | Oral | Miniature Schnauzer | 7 | Y | M | too pigmented | 80% | no | N/J/A | too pigmented |
| B 2 | Skin | Goldern Retriever | 5 | Y | M | 0 | 80% | no | N/J/A | spindeloid |
| B 3 | Skin | not identified | 8 | Y | F | 0 | 25% | no | no | mixed |
| B 4 | Skin | Poodle | 10 | Y | F | 2 | 50% | low | no | polygonal |
| B 5 | Skin | Boxer | 13 | Y | M | 2 | 20% | low | mix | mixed |
| B 6 | Skin | Jack Russel Terrier | 12 | Y | M | 2 | 20% | low | N/J/A | spindeloid |
| B 7 | Skin | Mixed | 13 | Y | M | 2 | 80% | no | yes | polygonal |
| B 8 | Skin | Miniature Schnauzer | 8 | Y | M | 2 | 20% | low | N/J/A | spindeloid |
| B 9 | Skin | Not Identified | 7 | Y | F | 4 | 60% | no | yes | spindeloid |
| B 10 | Oral | Mixed | 7 | Y | M | 3 | 80% | low | yes | spindeloid |
| B 11 | Skin | Lhasa Apso | 14 | Y | F | 5 | 20% | no | no | spindeloid |
| B 12 | Skin | Mixed | 6 | Y | M | too pigmented | 80% | no | yes | spindeloid |
| B 13 | Skin | Portuguese Water Dog | 6 | Y | F | too pigmented | 100% | no | N/J/A | spindeloid |
| B 14 | Skin | Pug | 5 | Y | M | too pigmented | 100% | low | N/J/A | spindeloid |
| B 15 | Skin | Miniature Schnauzer | 8 | Y | M | too pigmented | 90% | no | yes | too pigmented |
| B 16 | Oral | Mixed | 10 | Y | M | too pigmented | 90% | low | yes | too pigmented |
| B 17 | Oral | Mixed | 6 | Y | M | 3 | 0% | low | no | mixed |
| B 18 | Oral | Gordon Setter | 11 | Y | M | 5 | 50% | high | no | ulcerated |
| Cutaneous Melanomas Fresh and FFPE | | | | | | | | | | |
| CM 1 | Skin - ear tip | Doberman Pincher | 11 | Y | M | 4 | 50% | low | yes | spindeloid |
| CM 2 | Skin - Foot pad | German Shepherd | 9 | Y | F | 5 | 70% | high | N/J/A | spindeloid |
| CM 3 | Skin | Golden Retiever | 14 | Y | M | 8 | 0% | high | N/J/A | spindeloid |
| CM 4 | Skin | Mixed | 12 | Y | F | 50 | 0% | high | yes | spindeloid |
| CM 5 | Skin | Basset Hound | 8 | Y | F | 7 | 0% | low | yes | mixed |

N/J/A = no junction available

TABLE 3

Genome wide DNA copy number aberrations with at least 50% penetrance for three subtypes of canine melanocytic lesions, oral melanoma (OM), benign melanocytoma (B), and cutaneous melanoma (CM).

| Region chr: bp start-bp end | Length in bp | Cytoband | Event | Genes | Frequency % |
|---|---|---|---|---|---|
| OM n = 44 | | | | | |
| chr30: 19,102,383-19,660,901 | 558518 | q14.1 | CN Gain | 7 | 61.36 |
| chr30: 19,876,904-19,996,814 | 119910 | q14.1 | CN Gain | 1 | 61.36 |
| chr30: 20,116,984-20,240,659 | 123675 | q14.1 | CN Gain | 2 | 59.09 |
| chr30: 20,387,339-20,525,268 | 137929 | q14.1 | CN Gain | 3 | 59.09 |
| chr10: 20,583,579-20,598,892 | 15313 | q21 | CN Loss | 0 | 56.82 |
| chr26: 30,261,091-30,306,343 | 45252 | q24 | CN Loss | 2 | 75.00 |

TABLE 3-continued

Genome wide DNA copy number aberrations with at least 50% penetrance for three subtypes of canine melanocytic lesions, oral melanoma (OM), benign melanocytoma (B), and cutaneous melanoma (CM).

| Region chr: bp start-bp end | Length in bp | Cytoband | Event | Genes | Frequency % |
|---|---|---|---|---|---|
| CM n = 5 | | | | | |
| chr20: 10,929,869-57,175,686 | 46245817 | q11-17 | CN Gain | 359 | 80.00 |
| chr18: 21,439,849-21,824,376 | 384527 | q21 | CN Loss | 1 | 80.00 |
| chr23: 23,552,949-23,718,671 | 165722 | q21.1 | CN Loss | 0 | 80.00 |
| chr6: 48,260,040-49,569,575 | 1309535 | q23.1 | CN Loss | 0 | 80.00 |
| chr22: 63,472,754-63,531,977 | 59223 | q24 | CN Loss | 2 | 80.00 |
| chr5: 81,157,085-81,422,820 | 265735 | q35 | CN Loss | 0 | 80.00 |
| BM n = 18 | | | | | |
| chr27: 9,965,501-10,052,495 | 86994 | q12 | CN Gain | 5 | 73.33 |
| chr9: 20,973,038-21,556,711 | 583673 | q14 | CN Gain | 9 | 66.67 |
| chr10: 48,818,794-48,878,597 | 59803 | q21 | CN Gain | 1 | 66.67 |
| chr11: 55,214,228-55,245,594 | 31366 | q21 | CN Gain | 7 | 66.67 |
| chrX: 1-143,538 | 143538 | p22.3 | CN Gain | 12 | 60.00 |
| chr27: 5,862,415-6,022,827 | 160412 | q11 | CN Gain | 15 | 60.00 |
| chr7: 44,579,697-44,813,300 | 233603 | q17 | CN Gain | 12 | 60.00 |
| chr20: 60,767,150-61,000,000 | 232850 | q17 | CN Gain | 18 | 60.00 |
| chr6: 41,862,591-42,008,647 | 146056 | q22 | CN Gain | 13 | 60.00 |
| chr9: 53,793,547-53,944,034 | 150487 | q25 | CN Gain | 1 | 60.00 |
| chr18: 49,035,472-49,406,866 | 371394 | q25.1 | CN Gain | 10 | 60.00 |
| chr18: 55,807,318-55,861,598 | 54280 | q25.3 | CN Gain | 10 | 60.00 |
| chr18: 55,899,795-55,986,610 | 86815 | q25.3 | CN Gain | 2 | 60.00 |
| chr5: 59,367,552-59,417,133 | 49581 | q32 | CN Gain | 4 | 60.00 |
| chr5: 67,518,696-67,532,344 | 13648 | q33 | CN Gain | 3 | 60.00 |
| chr5: 81,157,085-81,374,416 | 217331 | q35 | CN Gain | 0 | 60.00 |
| chr1: 117,087,221-117,377,134 | 289913 | q37 | CN Gain | 13 | 60.00 |
| chr6: 48,348,336-48,987,554 | 639218 | q23.1 | CN Loss | 0 | 60.00 |
| chr8: 76,368,492-76,582,392 | 213900 | q33.3 | CN Loss | 9 | 60.00 |

TABLE 4

Significant genome wide DNA copy number aberrations using GISTIC for three subtypes of canine melanocytic lesions, oral melanoma (OM), benign melanocytoma (B), and cutaneous melanoma (CM).

| Region | Extended Region | Type | Q-Bound | G-Score | % of CNV Overlap |
|---|---|---|---|---|---|
| OM Regions with GISTIC Significance | | | | | |
| chr30: 19,396,688-19,516,412 | chr30: 19,085,315-19,660,901 | CN Gain | 4.25E−10 | 58.15 | 0 |
| chr10: 13,879,089-14,012,498 | chr10: 13,831,766-14,545,158 | CN Gain | 4.25E−10 | 41.10 | 0 |
| chr10: 4,760,299-4,831,368 | chr10: 4,646,739-4,831,368 | CN Gain | 9.56E−09 | 20.29 | 0 |
| chr23: 23,587,149-23,718,671 | chr23: 23,552,949-23,759,722 | CN Gain | 2.04E−06 | 16.76 | 0 |
| chr5: 81,189,945-81,349,070 | chr5: 81,189,945-81,406,580 | CN Gain | 3.70E−06 | 16.37 | 0 |
| chr26: 30,241,704-30,261,091 | chr26: 30,235,074-30,306,343 | CN Gain | 2.28E−04 | 13.61 | 0 |
| chr10: 53,156,724-53,472,065 | chr10: 52,387,783-53,749,886 | CN Gain | 0.00107783 | 12.49 | 0 |
| chr14: 10,075,226-10,292,604 | chr14: 8,574,711-10,686,666 | CN Gain | 0.00203921 | 11.99 | 0 |
| chrX: 74,854,890-74,974,869 | chrX: 74,807,177-75,285,514 | CN Gain | 0.00293874 | 11.67 | 0 |
| chr30: 36,243,187-36,304,668 | chr30: 34,265,324-37,004,574 | CN Gain | 0.00558962 | 11.17 | 0 |
| chr9: 21,086,878-21,202,655 | chr9: 21,029,083-21,202,655 | CN Gain | 0.01106026 | 10.52 | 0 |
| chr13: 65,919,719-66,047,830 | chr13: 65,730,802-66,047,830 | CN Gain | 0.01503172 | 10.22 | 0 |
| chr2: 86,827,776-86,968,017 | chr2: 86,827,776-86,968,017 | CN Gain | 0.01624276 | 10.16 | 0 |
| chr31: 7,929,632-8,198,080 | chr31: 5,859,849-13,293,969 | CN Gain | 0.01663631 | 10.13 | 0 |
| chr20: 56,256,652-56,280,086 | chr20: 56,256,652-56,286,566 | CN Gain | 0.01691585 | 10.10 | 0 |
| chr16: 62,203,097-62,515,898 | chr16: 62,203,097-62,515,898 | CN Gain | 0.02525589 | 9.65 | 0 |
| chr38: 3,405,422-3,538,896 | chr38: 3,189,443-4,217,229 | CN Gain | 0.03959025 | 9.17 | 0 |
| chr26: 30,261,091-30,306,343 | chr26: 30,241,704-30,306,343 | CN Loss | 1.34E−08 | 66.80 | 0 |
| chrX: 74,807,177-74,854,890 | chrX: 74,807,177-75,308,693 | CN Loss | 1.34E−08 | 41.91 | 0 |
| chr20: 56,256,652-56,280,086 | chr20: 56,256,652-56,280,086 | CN Loss | 1.34E−08 | 30.47 | 0 |
| chrX: 32,220,251-32,247,960 | chrX: 32,220,251-32,279,028 | CN Loss | 1.34E−08 | 27.09 | 0 |
| chr1: 114,637,937-114,656,865 | chr1: 114,637,937-114,665,364 | CN Loss | 1.34E−08 | 22.13 | 0 |
| chr27: 28,729,469-28,883,372 | chr27: 28,729,469-28,934,553 | CN Loss | 1.34E−08 | 20.46 | 0 |
| chr9: 42,294,685-42,320,234 | chr9: 42,294,685-42,320,234 | CN Loss | 2.77E−08 | 18.74 | 0 |
| chr5: 81,406,580-81,422,820 | chr5: 81,406,580-81,422,820 | CN Loss | 4.95E−08 | 18.26 | 0 |
| chr8: 76,376,971-76,418,529 | chr8: 76,376,971-76,418,529 | CN Loss | 9.40E−07 | 16.42 | 0 |
| chr10: 19,910,771-19,977,267 | chr10: 19,689,248-21,835,975 | CN Loss | 6.26E−05 | 13.87 | 0 |
| chr11: 44,252,111-44,285,901 | chr11: 44,211,059-44,467,159 | CN Loss | 1.07E−04 | 13.50 | 0 |

TABLE 4-continued

Significant genome wide DNA copy number aberrations using GISTIC for three subtypes of canine melanocytic lesions, oral melanoma (OM), benign melanocytoma (B), and cutaneous melanoma (CM).

| Region | Extended Region | Type | Q-Bound | G-Score | % of CNV Overlap |
|---|---|---|---|---|---|
| chr30: 10,620,776-10,640,884 | chr30: 10,245,871-10,747,987 | CN Loss | 2.07E-04 | 12.88 | 0 |
| chr31: 38,197,745-38,214,020 | chr31: 38,197,745-38,952,636 | CN Loss | 2.94E-04 | 12.51 | 0 |
| chr15: 23,472,577-23,517,219 | chr15: 23,472,577-27,817,003 | CN Loss | 3.49E-04 | 11.96 | 0 |
| chr16: 62,203,097-62,515,898 | chr16: 62,203,097-62,515,898 | CN Loss | 3.72E-04 | 11.76 | 0 |
| chr4: 3,015,106-3,070,165 | chr4: 3,015,106-3,113,601 | CN Loss | 3.90E-04 | 11.72 | 0 |
| chr18: 49,213,222-49,233,985 | chr18: 49,035,472-52,294,642 | CN Loss | 4.63E-04 | 11.56 | 0 |
| chr9: 20,488,956-20,590,682 | chr9: 20,474,456-20,633,826 | CN Loss | 0.00126535 | 10.62 | 0 |
| chr22: 23,845,574-24,002,337 | chr22: 14,537,344-38,654,160 | CN Loss | 0.00177263 | 10.30 | 0 |
| chr23: 23,563,470-23,718,671 | chr23: 23,563,470-23,759,722 | CN Loss | 0.00190609 | 10.24 | 0 |
| chr2: 86,827,776-86,968,017 | chr2: 86,827,776-86,968,017 | CN Loss | 0.00213317 | 10.15 | 0 |
| chr28: 43,262,646-43,385,184 | chr28: 42,633,500-44,164,395 | CN Loss | 0.00419263 | 9.59 | 0 |
| chrX: 85,524,761-85,581,869 | chrX: 85,524,761-85,581,869 | CN Loss | 0.00425608 | 9.56 | 0 |
| chr6: 41,862,591-41,926,348 | chr6: 41,862,591-43,080,399 | CN Loss | 0.00476427 | 9.47 | 0 |
| chr27: 40,740,881-40,754,138 | chr27: 40,740,881-40,754,138 | CN Loss | 0.01007504 | 8.55 | 0 |
| chr14: 46,598,461-46,678,089 | chr14: 46,584,383-46,678,089 | CN Loss | 0.01063497 | 8.48 | 0 |
| chr26: 4,131,462-4,206,619 | chr26: 3,473,009-7,813,608 | CN Loss | 0.01065659 | 8.46 | 0 |
| chr30: 26,188,574-26,199,784 | chr30: 25,874,552-26,560,890 | CN Loss | 0.01130433 | 8.35 | 0 |
| chr26: 40,924,095-40,968,469 | chr26: 40,904,816-40,994,620 | CN Loss | 0.0138418 | 8.07 | 0 |
| chr3: 65,296,031-65,396,261 | chr3: 65,232,960-65,432,693 | CN Loss | 0.01628326 | 7.89 | 0 |
| chr16: 4,213,825-4,239,959 | chr16: 4,213,825-4,258,636 | CN Loss | 0.01680828 | 7.84 | 0 |
| chr24: 49,984,397-50,090,042 | chr24: 49,900,755-50,241,858 | CN Loss | 0.01730606 | 7.80 | 0 |
| chr12: 75,148,337-75,267,772 | chr12: 75,130,246-75,302,377 | CN Loss | 0.01794901 | 7.76 | 0 |
| chr13: 5,458,646-5,505,233 | chr13: 5,458,646-5,505,233 | CN Loss | 0.02156167 | 7.52 | 0 |
| chr7: 4,481,626-4,583,154 | chr7: 4,144,974-4,583,154 | CN Loss | 0.02337253 | 7.43 | 0 |
| chr21: 33,751,639-33,837,189 | chr21: 33,703,628-33,837,189 | CN Loss | 0.02392112 | 7.39 | 0 |
| chr27: 5,828,184-6,011,259 | chr27: 5,029,882-6,022,827 | CN Loss | 0.04019147 | 6.85 | 0 |
| chr23: 23,787,810-23,842,143 | chr23: 23,759,722-23,856,187 | CN Loss | 0.04076074 | 6.84 | 0 |
| CM Regions with GISTIC Significance | | | | | |
| chr14: 58,094,987-58,849,668 | chr14: 46,802,954-63,000,000 | CN Gain | 0.01270454 | 4.78 | 0 |
| B Regions with GISTIC Significance | | | | | |
| chr27: 9,995,735-10,052,495 | chr27: 5,659,976-10,052,495 | CN Gain | 3.40E-13 | 8.65 | 0 |
| chrX: 74,854,890-74,866,879 | chrX: 74,825,586-75,297,878 | CN Gain | 3.40E-11 | 7.52 | 0 |
| chr18: 49,052,924-49,392,277 | chr18: 48,509,665-53,200,246 | CN Gain | 8.98E-11 | 7.18 | 0 |
| chr12: 5,623,620-5,667,555 | chr12: 5,608,152-6,861,836 | CN Gain | 6.91E-10 | 6.82 | 0 |
| chr23: 23,552,949-23,759,722 | chr23: 23,552,949-23,759,722 | CN Gain | 7.85E-10 | 6.76 | 0 |
| chr4: 39,053,116-39,170,521 | chr4: 39,042,223-39,194,034 | CN Gain | 7.85E-10 | 6.76 | 0 |
| chr5: 81,157,085-81,349,070 | chr5: 81,126,189-81,406,580 | CN Gain | 4.89E-09 | 6.39 | 0 |
| chrX: 0-143,538 | chrX: 0-143,538 | CN Gain | 4.89E-09 | 6.38 | 0 |
| chr9: 21,408,895-21,530,272 | chr9: 21,408,895-21,903,081 | CN Gain | 4.89E-09 | 6.37 | 0 |
| chr20: 43,468,559-43,575,482 | chr20: 43,468,559-49,771,075 | CN Gain | 4.89E-09 | 6.37 | 0 |
| chr14: 46,506,654-46,584,383 | chr14: 46,499,831-46,584,383 | CN Gain | 1.99E-08 | 6.10 | 0 |
| chr11: 55,214,228-55,245,594 | chr11: 55,204,045-55,321,496 | CN Gain | 4.99E-08 | 5.93 | 0 |
| chr6: 42,849,001-43,096,405 | chr6: 40,051,056-43,209,457 | CN Gain | 8.36E-08 | 5.83 | 0 |
| chr20: 60,767,150-61,000,000 | chr20: 56,358,468-61,000,000 | CN Gain | 4.22E-07 | 5.59 | 0 |
| chr37: 27,943,137-28,056,416 | chr37: 27,943,137-28,056,416 | CN Gain | 4.22E-07 | 5.51 | 0 |
| chr21: 24,569,743-24,698,749 | chr21: 24,569,743-24,698,749 | CN Gain | 9.96E-07 | 5.35 | 0 |
| chr7: 44,698,054-44,807,027 | chr7: 44,414,914-44,822,142 | CN Gain | 1.03E-06 | 5.33 | 0 |
| chr13: 40,394,483-40,777,502 | chr13: 40,373,884-40,967,200 | CN Gain | 8.97E-06 | 4.85 | 0 |
| chr1: 117,087,221-117,212,244 | chr1: 108,245,814-117,540,015 | CN Gain | 1.79E-05 | 4.68 | 0 |
| chr2: 82,590,966-82,665,656 | chr2: 81,151,300-84,212,283 | CN Gain | 2.54E-05 | 4.59 | 0 |
| chr2: 82,590,966-82,665,656 | chr2: 81,151,300-84,212,283 | CN Gain | 2.54E-05 | 4.59 | 0 |
| chr5: 22,776,305-22,816,038 | chr5: 11,096,260-22,923,069 | CN Gain | 3.94E-05 | 4.49 | 0 |
| chr10: 48,818,794-48,878,597 | chr10: 48,629,439-48,878,597 | CN Gain | 3.94E-05 | 4.48 | 0 |
| chr26: 27,113,254-27,134,319 | chr26: 27,062,988-27,134,319 | CN Gain | 4.20E-05 | 4.46 | 0 |
| chr24: 49,984,397-50,000,000 | chr24: 44,368,974-50,000,000 | CN Gain | 5.31E-05 | 4.40 | 0 |
| chr38: 25,155,765-25,303,468 | chr38: 25,078,372-26,000,000 | CN Gain | 5.98E-05 | 4.35 | 0 |
| chr8: 75,373,210-75,898,491 | chr8: 75,020,904-76,011,252 | CN Gain | 6.76E-05 | 4.29 | 0 |
| chr6: 19,774,410-19,798,691 | chr6: 19,774,410-19,798,691 | CN Gain | 8.64E-05 | 4.22 | 0 |
| chr9: 25,565,335-25,623,323 | chr9: 25,565,335-27,688,929 | CN Gain | 1.10E-04 | 4.15 | 0 |
| chr15: 4,348,577-4,531,244 | chr15: 4,325,685-4,531,244 | CN Gain | 1.88E-04 | 3.95 | 0 |
| chrX: 124,588,526-124,786,472 | chrX: 124,588,526-125,969,635 | CN Gain | 2.11E-04 | 3.93 | 0 |
| chr28: 43,491,902-43,596,808 | chr28: 41,370,311-44,000,000 | CN Gain | 2.11E-04 | 3.92 | 0 |
| chr9: 5,390,342-5,538,635 | chr9: 3,092,279-7,244,778 | CN Gain | 2.41E-04 | 3.88 | 0 |
| chr30: 36,613,375-36,765,421 | chr30: 36,613,375-37,004,574 | CN Gain | 2.68E-04 | 3.84 | 0 |
| chr34: 14,572,347-14,770,478 | chr34: 14,572,347-14,892,142 | CN Gain | 3.70E-04 | 3.73 | 0 |
| chr33: 29,504,739-29,553,814 | chr33: 29,452,267-34,000,000 | CN Gain | 3.96E-04 | 3.71 | 0 |
| chr18: 28,415,627-28,671,965 | chr18: 28,415,627-28,890,920 | CN Gain | 5.13E-04 | 3.64 | 0 |
| chr5: 34,619,831-34,709,337 | chr5: 33,442,777-36,845,062 | CN Gain | 5.57E-04 | 3.62 | 0 |
| chr26: 30,364,315-30,399,133 | chr26: 30,344,525-30,634,182 | CN Gain | 9.92E-04 | 3.45 | 0 |
| chr9: 45,217,496-45,500,017 | chr9: 45,054,425-60,003,763 | CN Gain | 9.92E-04 | 3.44 | 0 |

TABLE 4-continued

Significant genome wide DNA copy number aberrations using GISTIC for three subtypes of canine melanocytic lesions, oral melanoma (OM), benign melanocytoma (B), and cutaneous melanoma (CM).

| Region | Extended Region | Type | Q-Bound | G-Score | % of CNV Overlap |
|---|---|---|---|---|---|
| chr10: 23,187,573-23,306,445 | chr10: 20,598,892-23,334,650 | CN Gain | 0.00113505 | 3.40 | 0 |
| chr7: 3,723,393-3,918,808 | chr7: 3,006,080-5,095,917 | CN Gain | 0.00184027 | 3.22 | 0 |
| chr21: 43,460,055-43,535,921 | chr21: 43,460,055-43,747,598 | CN Gain | 0.00294658 | 3.06 | 0 |
| chrX: 41,834,336-41,912,597 | chrX: 41,834,336-42,379,293 | CN Gain | 0.00320759 | 3.03 | 0 |
| chr16: 12,113,382-12,144,999 | chr16: 12,113,382-12,204,649 | CN Gain | 0.0032828 | 3.03 | 0 |
| chr20: 40,230,971-40,780,518 | chr20: 40,208,746-40,780,518 | CN Gain | 0.0041088 | 2.96 | 0 |
| chr38: 3,697,794-3,752,667 | chr38: 3,016,721-3,752,667 | CN Gain | 0.0042585 | 2.95 | 0 |
| chr3: 76,831,901-76,967,393 | chr3: 76,831,901-76,994,058 | CN Gain | 0.00435091 | 2.94 | 0 |
| chr35: 6,483,064-6,637,134 | chr35: 3,071,242-6,637,134 | CN Gain | 0.00529068 | 2.88 | 0 |
| chr31: 40,377,799-40,554,261 | chr31: 38,908,007-42,000,000 | CN Gain | 0.00623578 | 2.83 | 0 |
| chr5: 59,113,319-59,488,835 | chr5: 59,082,995-67,699,985 | CN Gain | 0.00659926 | 2.81 | 0 |
| chr10: 4,510,998-4,831,368 | chr10: 3,004,950-4,923,812 | CN Gain | 0.00705634 | 2.78 | 0 |
| chr8: 6,607,735-6,694,814 | chr8: 4,558,537-6,694,814 | CN Gain | 0.00769219 | 2.75 | 0 |
| chr1: 3,839,223-4,167,983 | chr1: 3,662,504-4,182,287 | CN Gain | 0.01184963 | 2.60 | 0 |
| chr26: 13,412,428-13,538,765 | chr26: 3,518,142-20,573,625 | CN Gain | 0.01262203 | 2.57 | 0 |
| chr4: 91,000,000-91,398,109 | chr4: 91,000,000-91,398,109 | CN Gain | 0.01262203 | 2.57 | 0 |
| chr25: 53,312,633-54,000,000 | chr25: 53,312,633-54,000,000 | CN Gain | 0.01346224 | 2.56 | 0 |
| chr4: 62,114,752-62,159,956 | chr4: 61,830,636-62,168,311 | CN Gain | 0.01473081 | 2.52 | 0 |
| chr1: 119,496,512-120,447,489 | chr1: 119,459,266-125,000,000 | CN Gain | 0.01648036 | 2.48 | 0 |
| chr17: 3,702,574-3,825,817 | chr17: 3,052,892-9,579,356 | CN Gain | 0.01648036 | 2.48 | 0 |
| chr14: 7,937,663-8,121,364 | chr14: 7,434,627-8,553,791 | CN Gain | 0.0184279 | 2.44 | 0 |
| chr27: 41,211,822-41,300,574 | chr27: 41,071,656-48,000,000 | CN Gain | 0.01995682 | 2.41 | 0 |
| chr12: 4,554,654-4,607,625 | chr12: 3,031,642-4,607,625 | CN Gain | 0.02115983 | 2.39 | 0 |
| chr30: 40,808,066-40,861,842 | chr30: 40,320,384-41,839,853 | CN Gain | 0.02192708 | 2.38 | 0 |
| chr16: 3,100,910-3,476,369 | chr16: 3,100,910-4,213,825 | CN Gain | 0.02267356 | 2.37 | 0 |
| chr20: 7,525,125-7,605,556 | chr20: 3,024,722-7,605,556 | CN Gain | 0.02338029 | 2.36 | 0 |
| chr16: 17,971,591-18,121,626 | chr16: 17,347,364-18,227,857 | CN Gain | 0.02492774 | 2.32 | 0 |
| chr19: 32,550,976-32,746,669 | chr19: 32,225,673-32,806,005 | CN Gain | 0.02720893 | 2.30 | 0 |
| chr6: 34,178,794-34,314,993 | chr6: 34,178,794-34,449,912 | CN Gain | 0.02869225 | 2.28 | 0 |
| chr3: 63,363,880-63,750,829 | chr3: 59,402,935-65,504,828 | CN Gain | 0.04345763 | 2.14 | 0 |
| chr3: 94,000,000-94,171,927 | chr3: 94,000,000-94,171,927 | CN Gain | 0.04345763 | 2.13 | 0 |
| chr10: 31,563,018-31,893,061 | chr10: 31,563,018-32,036,160 | CN Gain | 0.04461882 | 2.13 | 0 |
| chr7: 82,799,910-83,000,000 | chr7: 82,744,812-83,000,000 | CN Gain | 0.04605908 | 2.12 | 0 |
| chr4: 31,908,866-32,379,618 | chr4: 30,373,234-32,851,368 | CN Gain | 0.04605908 | 2.11 | 0 |
| chrX: 74,825,586-74,854,890 | chrX: 58,521,100-120,549,593 | CN Loss | 3.28E-12 | 19.36 | 0 |
| chr26: 30,241,704-30,274,559 | chr26: 30,241,704-30,306,343 | CN Loss | 4.29E-06 | 11.27 | 0 |
| chr15: 23,192,685-23,592,383 | chr15: 20,997,597-23,592,383 | CN Loss | 4.25E-05 | 10.51 | 0 |
| chr37: 29,489,809-29,641,481 | chr37: 29,489,809-29,641,481 | CN Loss | 8.29E-05 | 10.35 | 0 |
| chr8: 76,368,492-76,418,529 | chr8: 76,365,171-76,582,392 | CN Loss | 7.77E-04 | 8.56 | 0 |
| chr27: 40,740,881-40,754,138 | chr27: 40,740,881-41,071,656 | CN Loss | 8.03E-04 | 8.31 | 0 |
| chr5: 81,406,580-81,422,820 | chr5: 81,406,580-81,452,184 | CN Loss | 0.00188539 | 7.21 | 0 |

TABLE 5

Differential chromosome regions with CN aberrations between primary canine oral melanoma (OM), primary canine cutaneous melanoma (CM), and canine benign melanocytoma (B).

| Region | Cyto-band | Event | Length | Freq. in <B> (%) | Freq. in <CM> (%) | Diff. | Probe-level p-value | p-value | q-bound | Gene |
|---|---|---|---|---|---|---|---|---|---|---|
| CM v B | | | | | | | | | | |
| chr12: 29,013,503-29,538,529 | q21.2 | CN Gain | 525026 | 0.0 | 60.0 | -60.0 | 0.00E+00 | 5.65E-03 | 0.616 | 1 |
| chr14: 56,723,556-59,852,681 | q22-q23 | CN Gain | 3129125 | 0.0 | 60.0 | -60.0 | 0.00E+00 | 5.65E-03 | 0.616 | 14 |
| chr14: 61,787,770-62,563,454 | q23 | CN Gain | 775684 | 0.0 | 60.0 | -60.0 | 0.00E+00 | 5.65E-03 | 0.616 | 6 |
| chr20: 34,924,975-35,532,615 | q15.1 | CN Gain | 607640 | 0.0 | 60.0 | -60.0 | 0.00E+00 | 5.65E-03 | 0.616 | 11 |
| chr20: 39,131,105-39,615,802 | q15.3 | CN Gain | 484697 | 0.0 | 60.0 | -60.0 | 0.00E+00 | 5.65E-03 | 0.616 | 5 |
| chr20: 42,838,556-43,439,311 | q15.3 | CN Gain | 600755 | 0.0 | 60.0 | -60.0 | 0.00E+00 | 5.65E-03 | 0.616 | 24 |
| chr7: 80,902,509-81,139,225 | q26 | CN Gain | 236716 | 0.0 | 60.0 | -60.0 | 1.11E-16 | 5.65E-03 | 0.616 | 3 |
| chr14: 5,608,750-5,833,997 | q21 | CN Gain | 225247 | 0.0 | 60.0 | -60.0 | 1.11E-16 | 5.65E-03 | 0.616 | 6 |

TABLE 5-continued

Differential chromosome regions with CN aberrations between primary canine oral melanoma (OM), primary canine cutaneous melanoma (CM), and canine benign melanocytoma (B).

| Region | Cyto-band | Event | Length | Freq. in <B> (%) | Freq. in <CM> (%) | Diff. | Probe-level p-value | p-value | q-bound | Gene |
|---|---|---|---|---|---|---|---|---|---|---|
| chr20: 48,629,806-49,134,219 | q15.3 | CN Gain | 504413 | 16.7 | 80.0 | −63.3 | 2.22E−16 | 1.73E−02 | 0.616 | 12 |
| chr7: 81,327,702-81,535,195 | q26 | CN Gain | 207493 | 0.0 | 60.0 | −60.0 | 3.44E−15 | 5.65E−03 | 0.616 | 2 |
| chr20: 54,160,798-54,593,373 | q16-q17 | CN Gain | 432575 | 0.0 | 60.0 | −60.0 | 4.03E−13 | 5.65E−03 | 0.616 | 27 |
| chr20: 50,826,543-51,074,680 | q16 | CN Gain | 248137 | 16.7 | 80.0 | −63.3 | 2.43E−12 | 1.73E−02 | 0.616 | 6 |
| chr20: 44,950,054-45,273,167 | q15.3 | CN Gain | 323113 | 16.7 | 80.0 | −63.3 | 3.45E−11 | 1.73E−02 | 0.616 | 15 |
| chr20: 9,631,235-9,846,893 | q11 | CN Gain | 215658 | 0.0 | 60.0 | −60.0 | 1.96E−09 | 5.65E−03 | 0.616 | 2 |
| chr20: 51,626,077-51,881,639 | q16 | CN Gain | 255562 | 16.7 | 80.0 | −63.3 | 6.14E−09 | 1.73E−02 | 0.616 | 5 |
| chr20: 22,738,829-22,957,667 | q13 | CN Gain | 218838 | 0.0 | 60.0 | −60.0 | 1.12E−06 | 5.65E−03 | 0.616 | 0 |
| chr20: 8,799,960-8,893,836 | q11 | CN Gain | 93876 | 0.0 | 60.0 | −60.0 | 1.42E−06 | 5.65E−03 | 0.616 | 1 |
| chr20: 40,938,157-41,127,958 | q15.3 | CN Gain | 189801 | 0.0 | 60.0 | −60.0 | 1.50E−06 | 5.65E−03 | 0.616 | 4 |
| chr20: 49,406,077-49,583,266 | q15.3 | CN Gain | 177189 | 16.7 | 80.0 | −63.3 | 6.25E−06 | 1.73E−02 | 0.616 | 11 |
| chr20: 10,929,869-11,055,355 | q11 | CN Gain | 125486 | 9.3 | 80.0 | −74.4 | 1.62E−05 | 7.76E−03 | 0.616 | 2 |
| chr20: 47,033,081-47,166,271 | q15.3 | CN Gain | 133190 | 16.7 | 80.0 | −63.3 | 2.31E−05 | 1.73E−02 | 0.616 | 4 |
| chr20: 10,131,212-10,241,822 | q11 | CN Gain | 110610 | 0.0 | 60.0 | −60.0 | 5.25E−05 | 5.65E−03 | 0.616 | 2 |
| chr20: 56,462,668-56,555,627 | q17 | CN Gain | 92959 | 22.2 | 100.0 | −77.8 | 3.28E−04 | 3.74E−03 | 0.616 | 6 |
| chr14: 5,234,860-5,273,352 | q11.2 | CN Gain | 38492 | 0.0 | 60.0 | −60.0 | 1.17E−03 | 5.65E−03 | 0.616 | 0 |
| chr20: 44,749,523-44,798,551 | q15.3 | CN Gain | 49028 | 7.6 | 80.0 | −74.4 | 1.53E−03 | 1.73E−02 | 0.616 | 1 |
| chr20: 41,727,887-41,772,352 | q15.3 | CN Gain | 44465 | 0.0 | 60.0 | −60.0 | 1.66E−02 | 5.65E−03 | 0.616 | 2 |
| chr20: 53,980,807-54,024,061 | q16 | CN Gain | 43254 | 16.7 | 80.0 | −63.3 | 1.74E−02 | 1.73E−02 | 0.616 | 2 |
| chr9: 20,973,038-21,556,711 | q14 | CN Gain | 583673 | 66.4 | 0.0 | 61.1 | 5.48E−02 | 3.73E−02 | 0.616 | 8 |
| chr17: 59,708,757-59,737,412 | q23 | CN Gain | 28655 | 0.0 | 60.0 | −60.0 | 5.67E−02 | 5.65E−03 | 0.616 | 1 |
| chr20: 52,449,099-52,462,326 | q16 | CN Gain | 13227 | 16.7 | 80.0 | −63.3 | 9.32E−01 | 1.73E−02 | 0.616 | 1 |
| chr6: 57,985,210-61,768,589 | q23.3 | CN Loss | 3783379 | 0.0 | 60.0 | −60.0 | 0.00E+00 | 5.65E−03 | 0.196 | 31 |
| chr6: 63,509,729-70,150,848 | q24.1-q24.3 | CN Loss | 6641119 | 0.0 | 60.0 | −60.0 | 0.00E+00 | 5.65E−03 | 0.196 | 36 |
| chr6: 71,931,091-73,247,675 | q25.1 | CN Loss | 1316584 | 0.0 | 60.0 | −60.0 | 0.00E+00 | 5.65E−03 | 0.196 | 12 |
| chr18: 16,137,042-19,268,908 | q12-q21 | CN Loss | 3131866 | 0.0 | 60.0 | −60.0 | 0.00+00 | 5.65E−03 | 0.196 | 18 |
| chr18: 20,168,647-21,429,875 | q21 | CN Loss | 1261228 | 0.0 | 60.0 | −60.0 | 0.00E+00 | 5.65E−03 | 0.196 | 14 |
| chr18: 30,423,853-31,166,586 | q22.2 | CN Loss | 742733 | 0.0 | 60.0 | −60.0 | 0.00E+00 | 5.65E−03 | 0.196 | 0 |
| chr18: 31,519,265-33,079,982 | q22.3 | CN Loss | 1560717 | 0.0 | 60.0 | −60.0 | 0.00E+00 | 5.65E−03 | 0.196 | 2 |
| chr18: 36,976,108-37,486,136 | q23 | CN Loss | 510028 | 0.0 | 60.0 | −60.0 | 0.00E+00 | 5.65E−03 | 0.196 | 6 |
| chr18: 38,868,924-39,420,478 | q23 | CN Loss | 551554 | 0.0 | 60.0 | −60.0 | 0.00E+00 | 5.65E−03 | 0.196 | 4 |
| chr18: 53,200,246-53,990,114 | q25.1 | CN Loss | 789868 | 0.0 | 60.0 | −60.0 | 0.00E+00 | 5.65E−03 | 0.196 | 25 |
| chr22: 3,056,579-3,707,698 | q11.1 | CN Loss | 651119 | 0.0 | 60.0 | −60.0 | 0.00E+00 | 5.65E−03 | 0.196 | 7 |
| chr22: 3,865,032-4,908,525 | q11.1-q11.2 | CN Loss | 1043493 | 0.0 | 60.0 | −60.0 | 0.00E+00 | 5.65E−03 | 0.196 | 5 |
| chr22: 5,325,133-5,981,205 | q11.2 | CN Loss | 656072 | 0.0 | 60.0 | −60.0 | 0.00E+00 | 5.65E−03 | 0.196 | 7 |
| chr22: 6,406,853-7,556,541 | q11.2 | CN Loss | 1149688 | 0.0 | 60.0 | −60.0 | 0.00E+00 | 5.65E−03 | 0.196 | 8 |

TABLE 5-continued

Differential chromosome regions with CN aberrations between primary canine oral melanoma (OM), primary canine cutaneous melanoma (CM), and canine benign melanocytoma (B).

| Region | Cyto-band | Event | Length | Freq. in <B> (%) | Freq. in <CM> (%) | Diff. | Probe-level p-value | p-value | q-bound | Gene |
|---|---|---|---|---|---|---|---|---|---|---|
| chr22: 7,906,394-12,107,407 | q11.2 | CN Loss | 4201013 | 0.0 | 60.0 | −60.0 | 0.00E+00 | 5.65E−03 | 0.196 | 31 |
| chr22: 12,618,901-18,986,118 | q11.2-q12.3 | CN Loss | 6367217 | 0.0 | 60.0 | −60.0 | 0.00E+00 | 5.65E−03 | 0.196 | 7 |
| chr22: 39,700,274-58,811,660 | q22-q24 | CN Loss | 1.9E+07 | 0.0 | 60.0 | −60.0 | 0.00E+00 | 5.65E−03 | 0.196 | 56 |
| chr22: 59,940,933-63,256,620 | q24 | CN Loss | 3315687 | 0.0 | 60.0 | −60.0 | 0.00E+00 | 5.65E−03 | 0.196 | 18 |
| chr22: 63,472,754-64,369,703 | q24 | CN Loss | 896949 | 0.3 | 61.3 | −80.0 | 0.00E+00 | 5.65E−03 | 0.196 | 21 |
| chr18: 21,439,849-27,874,576 | q21-q22.1 | CN Loss | 6434727 | 0.8 | 61.2 | −74.4 | 0.00E+00 | 1.73E−02 | 0.282 | 11 |
| chr6: 56,621,808-57,009,959 | q23.3 | CN Loss | 388151 | 0.0 | 60.0 | −60.0 | 8.88E−16 | 5.65E−03 | 0.196 | 1 |
| chr18: 45,873,209-46,030,785 | q24 | CN Loss | 157576 | 0.0 | 60.0 | −60.0 | 1.22E−15 | 5.65E−03 | 0.196 | 3 |
| chr18: 44,055,769-44,242,185 | q24 | CN Loss | 186416 | 0.0 | 60.0 | −60.0 | 7.42E−12 | 5.65E−03 | 0.196 | 14 |
| chr6: 73,811,433-73,959,664 | q25.1 | CN Loss | 148231 | 0.0 | 60.0 | −60.0 | 2.26E−10 | 5.65E−03 | 0.196 | 3 |
| chr23: 23,552,949-23,718,671 | q21.1 | CN Loss | 165722 | 16.7 | 80.0 | −63.3 | 1.28E−09 | 1.73E−02 | 0.282 | 0 |
| chr18: 15,091,843-15,315,133 | q12 | CN Loss | 223290 | 0.0 | 60.0 | −60.0 | 3.10E−09 | 5.65E−03 | 0.196 | 2 |
| chr3: 91,078,961-91,201,866 | q35.2 | CN Loss | 122905 | 0.0 | 60.0 | −60.0 | 7.97E−07 | 5.65E−03 | 0.196 | 1 |
| chr22: 19,370,270-19,470,842 | q12.3 | CN Loss | 100572 | 0.0 | 60.0 | −60.0 | 1.25E−05 | 5.65E−03 | 0.196 | 2 |
| chr3: 65,296,031-65,432,693 | q32 | CN Loss | 136662 | 0.0 | 60.0 | −60.0 | 2.97E−05 | 5.65E−03 | 0.196 | 0 |
| chr18: 38,039,895-38,145,764 | q23 | CN Loss | 105869 | 0.0 | 60.0 | −60.0 | 1.01E−04 | 5.65E−03 | 0.196 | 1 |
| chr6: 71,434,654-71,483,100 | q25.1 | CN Loss | 48446 | 0.0 | 60.0 | −60.0 | 1.41E−03 | 5.65E−03 | 0.196 | 2 |
| chr18: 49,368,197-49,383,331 | q25.1 | CN Loss | 15134 | 0.0 | 60.0 | −60.0 | 2.30E−02 | 5.65E−03 | 0.196 | 0 |
| chr18: 58,595,017-58,606,617 | q25.3 | CN Loss | 11600 | 0.0 | 60.0 | −60.0 | 1.32E−01 | 5.65E−03 | 0.196 | 1 |
| chr8: 76,326,077-76,353,946 | q33.3 | CN Loss | 27869 | 13.9 | 80.0 | −68.9 | 1.78E−01 | 1.73E−02 | 0.282 | 1 |
| CM vs OM | | | | | | | | | | |
| chr20: 56,362,306-57,041,431 | q17 | CN Gain | 679125 | 82.7 | 16.1 | 61.8 | 0.00E+00 | 1.00E−02 | 1.000 | 25 |
| chr30: 19,102,383-19,660,901 | q14.1 | CN Gain | 558518 | 0.0 | 61.4 | −61.4 | 0.00E+00 | 1.38E−02 | 1.000 | 7 |
| chr20: 48,049,703-48,520,235 | q15.3 | CN Gain | 470532 | 80.0 | 17.7 | 61.8 | 1.11E−16 | 1.00E−02 | 1.000 | 29 |
| chr20: 48,534,617-48,936,628 | q15.3 | CN Gain | 402011 | 80.0 | 17.1 | 61.8 | 3.71E−13 | 1.00E−02 | 1.000 | 9 |
| chr20: 40,444,954-40,780,518 | q15.3 | CN Gain | 335564 | 80.0 | 17.9 | 61.8 | 5.57E−13 | 1.00E−02 | 1.000 | 16 |
| chr20: 49,853,240-50,112,676 | q16 | CN Gain | 259436 | 80.0 | 14.3 | 61.8 | 1.20E−11 | 1.00E−02 | 1.000 | 11 |
| chr20: 52,824,996-52,996,836 | q16 | CN Gain | 171840 | 80.0 | 16.8 | 61.8 | 1.40E−10 | 1.00E−02 | 1.000 | 14 |
| chr30: 19,876,904-19,996,814 | q14.1 | CN Gain | 119910 | 0.0 | 61.4 | −61.4 | 1.08E−08 | 1.38E−02 | 1.000 | 1 |
| chr20: 47,033,081-47,224,687 | q15.3 | CN Gain | 191606 | 80.0 | 18.2 | 61.8 | 2.10E−08 | 1.00E−02 | 1.000 | 8 |
| chr20: 49,276,174-49,343,247 | q15.3 | CN Gain | 67073 | 80.0 | 18.2 | 61.8 | 5.50E−07 | 1.00E−02 | 1.000 | 6 |
| chr20: 44,812,069-44,993,595 | q15.3 | CN Gain | 181526 | 80.0 | 16.0 | 61.8 | 1.43E−06 | 1.00E−02 | 1.000 | 5 |
| chr20: 47,733,306-47,878,953 | q15.3 | CN Gain | 145647 | 80.0 | 16.8 | 61.8 | 1.30E−05 | 1.00E−02 | 1.000 | 9 |
| chr20: 47,289,293-47,424,027 | q15.3 | CN Gain | 134734 | 80.0 | 15.7 | 61.8 | 1.58E−05 | 1.00E−02 | 1.000 | 3 |
| chr20: 39,692,824-39,761,640 | q15.3 | CN Gain | 68816 | 80.0 | 15.3 | 64.1 | 2.66E−05 | 6.82E−03 | 1.000 | 2 |
| chr20: 10,929,869-11,021,062 | q11 | CN Gain | 91193 | 80.0 | 16.1 | 61.8 | 6.69E−04 | 1.00E−02 | 1.000 | 1 |

TABLE 5-continued

Differential chromosome regions with CN aberrations between primary canine oral melanoma (OM), primary canine cutaneous melanoma (CM), and canine benign melanocytoma (B).

| Region | Cyto-band | Event | Length | Freq. in <B> (%) | Freq. in <CM> (%) | Diff. | Probe-level p-value | p-value | q-bound | Gene |
|---|---|---|---|---|---|---|---|---|---|---|
| chr20: 52,401,235-52,462,326 | q16 | CN Gain | 61091 | 80.0 | 18.2 | 61.8 | 1.99E−03 | 1.00E−02 | 1.000 | 8 |
| chr20: 40,295,833-40,353,458 | q15.3 | CN Gain | 57625 | 80.0 | 18.2 | 61.8 | 2.09E−03 | 1.00E−02 | 1.000 | 5 |
| chr20: 53,009,988-53,113,442 | q16 | CN Gain | 103454 | 80.0 | 18.2 | 61.8 | 7.21E−03 | 1.00E−02 | 1.000 | 4 |
| chr20: 51,626,077-51,671,841 | q16 | CN Gain | 45764 | 80.0 | 18.2 | 61.8 | 3.73E−02 | 1.00E−02 | 1.000 | 4 |
| chr20: 55,265,830-55,300,554 | q17 | CN Gain | 34724 | 80.0 | 16.5 | 61.8 | 5.74E−02 | 1.00E−02 | 1.000 | 2 |
| chr20: 51,430,498-51,436,664 | q16 | CN Gain | 6166 | 80.0 | 18.2 | 61.8 | 8.62E−02 | 1.00E−02 | 1.000 | 2 |
| chr20: 43,439,311-43,456,298 | q15.3 | CN Gain | 16987 | 80.0 | 15.9 | 64.1 | 1.01E−01 | 6.82E−03 | 1.000 | 1 |
| chr20: 55,466,763-55,484,948 | q17 | CN Gain | 18185 | 80.0 | 18.2 | 61.8 | 1.01E−01 | 1.00E−02 | 1.000 | 1 |
| chr20: 45,084,782-45,097,744 | q15.3 | CN Gain | 12962 | 80.0 | 18.2 | 61.8 | 9.09E−01 | 1.00E−02 | 1.000 | 1 |
| chr18: 58,785,242-58,847,127 | q25.3 | CN Loss | 61885 | 60.0 | 0.0 | 60.0 | 2.67E−04 | 5.43E−04 | 1.000 | 1 |
| chr18: 21,439,849-21,824,376 | q21 | CN Loss | 384527 | 80.0 | 16.5 | 61.8 | 3.13E−03 | 1.00E−02 | 1.000 | 1 |
| OM vs B | | | | | | | | | | |
| chr30: 19,085,315-19,792,342 | q14.1 | CN Gain | 707027 | 60.5 | 5.6 | 51.3 | 0.00E+00 | 1.58E−04 | 0.038 | 9 |
| chr30: 19,812,516-21,427,202 | q14.1 | CN Gain | 1614686 | 56.2 | 2.7 | 50.0 | 0.00E+00 | 1.58E−04 | 0.038 | 20 |
| chr30: 18,445,429-18,848,546 | q14.1 | CN Gain | 403117 | 54.1 | 0.0 | 50.0 | 0.00E+00 | 7.81E−05 | 0.030 | 4 |
| chr18: 49,052,924-49,406,866 | q25.1 | CN Gain | 353942 | 13.4 | 68.4 | −60.9 | 7.92E−06 | 1.81E−04 | 0.043 | 9 |
| chr27: 9,965,501-10,052,495 | q12 | CN Gain | 86994 | 17.4 | 72.2 | −56.3 | 6.10E−03 | 8.92E−05 | 0.032 | 4 |
| chr30: 21,556,538-21,606,960 | q14.1-q14.2 | CN Gain | 50422 | 50.0 | 0.0 | 50.0 | 3.18E−02 | 7.81E−05 | 0.030 | 0 |
| chr27: 5,904,167-6,011,259 | q11 | CN Gain | 107092 | 18.2 | 72.2 | −54.0 | 5.80E−02 | 8.92E−05 | 0.032 | 3 |
| chr30: 21,471,751-21,486,205 | q14.1 | CN Gain | 14454 | 50.0 | 0.0 | 50.0 | 1.82E−01 | 7.81E−05 | 0.030 | 0 |
| chr18: 49,517,445-49,534,276 | q25.1 | CN Gain | 16831 | 9.1 | 61.1 | −52.0 | 3.66E−01 | 4.92E−05 | 0.024 | 1 |
| chr30: 8,498,046-9,636,740 | q12 | CN Loss | 1138694 | 52.2 | 0.0 | 50.0 | 1.20E−05 | 7.81E−05 | 0.023 | 4 |
| chr30: 10,193,135-10,720,246 | q13 | CN Loss | 527111 | 52.4 | 0.0 | 50.0 | 1.31E−03 | 7.81E−05 | 0.023 | 14 |
| chr30: 12,726,759-13,250,634 | q13 | CN Loss | 523875 | 51.2 | 0.0 | 50.0 | 1.38E−03 | 7.81E−05 | 0.023 | 11 |
| chr18: 49,147,788-49,270,987 | q25.1 | CN Loss | 123199 | 52.5 | 0.0 | 50.0 | 5.23E−02 | 7.81E−05 | 0.023 | 4 |
| chr30: 12,380,210-12,488,823 | q13 | CN Loss | 108613 | 51.1 | 0.0 | 50.0 | 1.09E−01 | 7.81E−05 | 0.023 | 2 |
| chr10: 19,910,771-20,010,497 | q21 | CN Loss | 99726 | 51.5 | 0.0 | 50.0 | 2.93E−01 | 7.81E−05 | 0.023 | 7 |
| chr30: 10,079,573-10,124,393 | q13 | CN Loss | 44820 | 50.0 | 0.0 | 50.0 | 3.37E−01 | 7.81E−05 | 0.023 | 1 |
| chr10: 20,891,421-21,034,598 | q21 | CN Loss | 143177 | 50.0 | 0.0 | 50.0 | 3.73E−01 | 7.81E−05 | 0.023 | 0 |
| chr30: 11,975,124-12,063,650 | q13 | CN Loss | 88526 | 50.0 | 0.0 | 50.0 | 6.30E−01 | 7.81E−05 | 0.023 | 2 |

TABLE 6

Proposed genes involved in canine oral melanoma pathogenesis.

|  | Cell Function |
|---|---|
| CFA 30 Gain | |
| SLC27A2 | Lipid biosynthesis and fatty acid degradation. |
| HDC | Converts L-histidine to histamine, associated with HDC include mast cell neoplasm. |
| GABPB1 | Transcription factor. |
| USP8 | Required for the cell to enter the S phase of the cell cycle. Also functions as a positive regulator in the Hedgehog signaling pathway in development and downstream signaling of activated FGFR. |
| TRPM7 | Kinase activity is essential for the ion channel function. |
| SPPL2A | Member of the GXGD family of aspartic proteases. |
| CFA 30 Loss | |
| SPRED1 | Tyrosine kinase substrate that inhibits growth-factor-mediated activation of MAP kinase through C-KIT receptor signaling pathway. |
| RASGRP1 | Diacylglycerol (DAG)-regulated nucleotide exchange factor specifically activating RAS through the exchange of bound GDP for GTP, which activates the Erk/MAP kinase cascade. |
| FAM98B | Component of the tRNA-splicing ligase complex |
| CFA 3 loss | |
| FGFR3 | Tyrosine-protein kinase that plays an essential role in the regulation of cell proliferation, differentiation and apoptosis |
| TACC3 | Motor spindle protein that may play a role in stabilization of the mitotic spindle. This protein may also play a role in growth a differentiation of certain cancer cells. |
| TMEM129 | Multi-pass membrane protein (Potential) |
| SLBP | Stabilizes mature histone mRNA and could be involved in cell-cycle regulation of histone gene expression. |
| FAM53A | May play an important role in neural development. |

TABLE 7

Aberrations with at least 60% penetrance for three subtypes of canine melanocytic, oral melanoma (OM), cutaneous melanoma (CM), and melanocytoma (B) lesions after recoding as human (HSA).

| Region chr: bp start-bp end | Length in bp | Cyto-band | Event | Genes | Freq. % | Q-Bound | % of CNV |
|---|---|---|---|---|---|---|---|
| OM n = 44 | | | | | | | |
| chr4: 70,508,745-70,648,668 | 139923 | q13.3 | CN Gain | 2 | 52.3 | 0 | 0.00 |
| chr9: 139,959,550-140,076,719 | 117169 | q34.3 | CN Loss | 10 | 52.3 | 0 | 2.42 |
| chr11: 1,794,537-2,127,344 | 332807 | p15.5 | CN Loss | 11 | 56.8 | 0 | 1.33 |
| chr12: 69,140,376-69,310,630 | 170254 | q15 | CN Gain | 4 | 50.0 | 0 | 0.56 |
| chr15: 38,701,609-38,952,741 | 251132 | q14 | CN Loss | 2 | 56.8 | 0 | 0.00 |
| chr15: 40,071,513-40,108,709 | 37196 | q14-q15.1 | CN Loss | 2 | 50.0 | 0 | 0.00 |
| chr15: 40,677,763-40,752,657 | 74894 | q15.1 | CN Loss | 4 | 54.5 | 0 | 100.00 |
| chr15: 43,269,351-43,435,842 | 166491 | q15.2 | CN Loss | 2 | 50.0 | 0 | 0.00 |
| chr15: 49,739,758-49,752,772 | 13014 | q21.2 | CN Gain | 3 | 56.8 | 0 | 0.00 |
| chr15: 49,880,023-49,947,711 | 67688 | q21.2 | CN Gain | 3 | 56.8 | 0 | 0.00 |
| chr15: 50,413,935-51,086,810 | 672875 | q21.2 | CN Gain | 14 | 56.8 | 0 | 0.00 |
| chr15: 51,419,334-51,553,648 | 134314 | q21.2 | CN Gain | 8 | 56.8 | 0 | 0.00 |
| chr15: 51,680,450-51,843,291 | 162841 | q21.2 | CN Gain | 2 | 54.5 | 0 | 0.00 |
| chr15: 52,127,372-52,146,078 | 18706 | q21.2 | CN Gain | 1 | 56.8 | 0 | 0.00 |

TABLE 7-continued

Aberrations with at least 60% penetrance for three subtypes of canine melanocytic, oral melanoma (OM), cutaneous melanoma (CM), and melanocytoma (B) lesions after recoding as human (HSA).

| Region chr: bp start-bp end | Length in bp | Cyto-band | Event | Genes | Freq. % | Q-Bound | % of CNV |
|---|---|---|---|---|---|---|---|
| chr15: 52,619,742-52,673,926 | 54184 | q21.2 | CN Gain | 1 | 54.5 | 0 | 0.00 |
| chr15: 52,819,229-52,865,102 | 45873 | q21.2 | CN Gain | 2 | 52.3 | 0 | 0.00 |
| chr16: 72,782,701-72,793,246 | 10545 | q22.2 | CN Loss | 1 | 50.0 | 0 | 0.00 |
| chr22: 49,365,468-50,206,932 | 841464 | q13.32-q13.33 | CN Loss | 4 | 54.5 | 0.016 | 2.90 |
| CM n = 5 | | | | | | | |
| chr1: 104,846,149-106,466,025 | 1619876 | p21.1 | CN Loss | 1 | 80.0 | 1 | 8.36 |
| chr3: 10,330,119-10,478,665 | 148546 | p25.3 | CN Gain | 5 | 80.0 | 1 | 0.00 |
| chr3: 23,033,528-23,227,218 | 193690 | p24.3 | CN Loss | 0 | 80.0 | 1 | 0.00 |
| chr3: 46,895,009-47,059,073 | 164064 | p21.31 | CN Gain | 6 | 80.0 | 1 | 0.00 |
| chr3: 48,138,725-48,550,356 | 411631 | p21.31 | CN Gain | 15 | 80.0 | 1 | 0.00 |
| chr3: 48,668,514-48,719,793 | 51279 | p21.31 | CN Gain | 4 | 80.0 | 1 | 0.00 |
| chr3: 49,646,565-50,156,399 | 509834 | p21.31 | CN Gain | 19 | 80.0 | 1 | 3.16 |
| chr3: 51,722,814-52,597,921 | 875107 | p21.2-p21.1 | CN Gain | 42 | 80.0 | 1 | 0.00 |
| chr3: 53,166,746-53,305,143 | 138397 | p21.1 | CN Gain | 2 | 80.0 | 1 | 0.00 |
| chr7: 78,150,647-78,549,045 | 398398 | q21.11 | CN Loss | 1 | 80.0 | 1 | 0.00 |
| chr16: 72,450,875-72,793,246 | 342371 | q22.2 | CN Loss | 3 | 80.0 | 1 | 0.00 |
| chr17: 4,602,476-4,749,428 | 146952 | p13.2 | CN Gain | 12 | 80.0 | 1 | 0.00 |
| chr19: 6,723,282-6,941,309 | 218027 | p13.3-p13.2 | CN Gain | 5 | 100.0 | 1 | 36.31 |
| chr19: 7,915,050-11,316,157 | 3401107 | p13.2 | CN Gain | 122 | 80.0 | 1 | 4.62 |
| chr19: 12,913,005-14,816,413 | 1903408 | p13.2-p13.12 | CN Gain | 62 | 80.0 | 1 | 2.32 |
| chr19: 15,152,417-20,370,056 | 5217639 | p13.12-p12 | CN Gain | 221 | 80.0 | 1 | 6.50 |
| BM n = 18 | | | | | | | |
| chr1: 0-924,995 | 924995 | p36.33 | CN Gain | 38 | 64.3 | 0 | 98.86 |
| chr1: 12,246,974-12,500,843 | 253869 | p36.22 | CN Gain | 3 | 71.4 | 0 | 0.00 |
| chr1: 155,927,443-156,237,440 | 309997 | q22 | CN Gain | 14 | 64.3 | 0 | 0.34 |
| chr2: 43,382,146-43,452,004 | 69858 | p21 | CN Gain | 1 | 64.3 | 0 | 0.00 |
| chr9: 137,181,234-137,370,987 | 189753 | q34.2 | CN Gain | 2 | 64.3 | 0 | 0.00 |
| chr11: 1,776,852-2,256,415 | 479563 | p15.5 | CN Gain | 21 | 64.3 | 0 | 0.92 |
| chr11: 63,966,032-64,056,915 | 90883 | q13.1 | CN Gain | 12 | 64.3 | 0 | 0.00 |
| chr12: 52,391,144-52,523,021 | 131877 | q13.13 | CN Gain | 4 | 71.4 | 0 | 0.52 |
| chr16: 67,963,523-68,031,710 | 68187 | q22.1 | CN Gain | 7 | 64.3 | 0 | 0.00 |
| chr16: 72,468,995-72,730,668 | 261673 | q22.2 | CN Gain | 2 | 64.3 | 0 | 0.00 |
| chr16: 88,794,946-88,939,297 | 144351 | q24.3 | CN Gain | 8 | 64.3 | 0 | 41.99 |

TABLE 8

Homologous copy number aberrations, gain (G) or loss (L), between canine (CFA) melanocytic lesions, malignant melanoma (Mel) and benign melanocytomas (Ben) and two human (HSA) melanoma subtypes, mucosal melanoma (mucosal) and acral melanoma (acral).

| Genes | Region in HSA | G/L in Mucosal | G/L in Acral | Region in CFA | G/L in Mel | G/L in Ben |
|---|---|---|---|---|---|---|
| CDK4 | 12q14 (12-57.74 Mb) | G | G | 15-53 Mb | L | N |
| CDKN2A | 9p21 (9-21.96 Mb) | L | L | 11-44.06 Mb | L | N |
| PTEN | 10q32.3 (10-87.86 Mb) | L | L | 26-40.0 Mb | L | L |
| MYC | 8q24.21 (8-127.73 Mb) | G | G | 13-27.28 Mb | G | N |
| KIT | 4q12 (4-75.57 Mb) | G | N | 13-49.50 Mb | G | N |
| TP53 | 17p13.1 (17-7.66 Mb) | N | N | 5-35.0 Mb | L/G | L |
| CCND1 | 11q13 (11-69.65 Mb) | G | G | 18-51.1 Mb | L | N |
| RB-1 | 13q14.2 (13-48.48 Mb) | N | N | 22-6.0 Mb | L | N |
| CDKN1A | 6p21.2 (6-36.68 Mb) | G | G | 12-8.6 Mb | L | N |
| B-RAF | 7q34 (7-140.92 Mb) | G | G | 16-11.49 Mb | L | N |

TABLE 9

| Target region | key locus | CH-82 clone | start | stop | overlap |
|---|---|---|---|---|---|
| 26: 44253176-44256016 Mb | PTEN | 314G09 | 40729598 | 40911630 | 67612 |
| | | 512G14 | 40844018 | 41078623 | |
| | | 047M14 | 41052124 | 41230433 | 26499 |
| | | | | TOTAL | 500835 |
| 5: 35557006-35560756 Mb | TP53 | 199E04 | 35331852 | 35520376 | 69967 |
| | | 221P11 | 35450409 | 35651123 | |
| | | 185K03 | 35592600 | 35820597 | 58523 |
| | | | | TOTAL | 488745 |
| 13: 50040750-50122138 Mb | c-KIT | 039J17 | 49827508 | 50021682 | 30319 |
| | | 524B22 | 49991363 | 50201827 | |
| | | 043D09 | 50186090 | 50371023 | 15737 |
| | | | | TOTAL | 543515 |
| 15: 54244626-54245248 Mb | CDK4 | 403E04 | 53922786 | 54130237 | 55791 |
| | | 227A01 | 54074446 | 54251670 | |
| | | 017B02 | 54223578 | 54387481 | 28092 |
| | | | | TOTAL | 464695 |
| 13: 28,238,008-28,242,545 Mb | c-MYC | 136F15 | 27885453 | 28104973 | 19691 |
| | | 335M01 | 28085282 | 28265714 | |
| | | 209M01 | 28207431 | 28382509 | 58283 |
| | | | | TOTAL | 497056 |
| 11: 44253176-44256016 Mb | CDKN2A | 043A07 | 44061103 | 44283223 | 26922 |
| | | 325C12 | 44256301 | 44428212 | |
| | | 166H01 | 44393313 | 44561750 | 34899 |
| | | | | TOTAL | 500647 |
| 12: 8,751,893-8,755,004 Mb | CDKN1A | 060J11 | 8648955 | 8871237 | 52367 |
| | | 465H20 | 8818870 | 9013484 | |
| | | | | TOTAL | 364529 |
| 22: 6,007,254-6,093,096 Mb | RB-1 | 479C11 | 5765800 | 5982802 | 15774 |
| | | 021N23 | 5967028 | 6133019 | |
| | | 522K16 | 6084801 | 6248558 | 48218 |
| | | | | TOTAL | 482758 |
| 16: 11,187,222-11,275,928 Mb | BRAF | 257E03 | 11163065 | 11374118 | 86857 |
| | | 515N08 | 11287261 | 11464323 | |
| | | | | TOTAL | 301258 |
| 18: 51,527,953-51,535,734 Mb | CCND1 | 024F02 | 51293932 | 51503911 | 25056 |
| | | 088I24 | 51478855 | 51688507 | |
| | | 278J02 | 51651758 | 51813747 | 36749 |
| | | | | TOTAL | 519815 |

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A method for detecting and treating a canine malignant oral melanoma, the method comprising:
   (a) measuring copy numbers of CFA 10:5, CFA 10:14, CFA 10:20, CFA 30:9, and CFA 30:19 in a biological sample from a dog, wherein:
      (i) the biological sample comprises cancer cells isolated from the oral cavity of the dog and/or DNA isolated therefrom; and
      (ii) the copy numbers of CFA 10:5, CFA 10:14, CFA 10:20, CFA 30:9, and CFA 30:19 are measured by aberrations at CFA chr10:1617000-2513700, CFA chr10:10887000-11116000, CFA chr10:17366629-17720225, CFA chr30:5300000-6000000, and CFA chr30:15500000-18000000 from camfam3, respectively;
   (b) detecting increased copy numbers of CFA 10:5, CFA 10:14, and CFA 30:19 and reduced copy numbers of CFA 10:20 and CFA 30:9 compared to a normal control in the biological sample;
   (c) diagnosing the dog with malignant oral melanoma; and (d) treating the malignant oral melanoma in the dog with surgical resection, radiation therapy, an anti-melanoma vaccine, chemotherapy, or any combination thereof.

2. The method of claim 1, wherein the copy numbers of CFA 10:5, CFA 10:14, and CFA 30:19 are >2.0.

3. The method of claim 1, wherein the copy numbers of CFA 10:20 and CFA 30:9 are <2.0.

4. The method of claim 1, wherein both the copy numbers of CFA 10:5, CFA 10:14, and CFA 30:19 are >2.0 and the copy numbers of CFA 10:20 and CFA 30:9 are <2.0.

5. The method of claim 1, wherein the copy numbers are measured by fluorescence in situ hybridization (FISH).

6. The method of claim 1, wherein the copy numbers are measured by polymerase chain reaction (PCR).

7. The method of claim 1, wherein the copy numbers are measured by comparative genomic hybridization (CGH).

8. The method of claim 1, wherein the copy numbers are measured by next generation sequencing.

9. The method of claim 1, wherein the biological sample is a tissue sample.

10. The method of claim 1, wherein the sample is a fresh-frozen sample.

11. The method of claim 1, wherein the sample is a fresh sample.

12. The method of claim 1, wherein the sample is a fixed sample.

13. The method of claim 12, wherein the fixed sample is a formalin-fixed, paraffin-embedded sample.

\* \* \* \* \*